US012780863B2

(12) United States Patent
Gin et al.

(10) Patent No.: US 12,780,863 B2
(45) **Date of Patent: *Nov. 3, 2026**

(54) TRITERPENE SAPONIN ANALOGUES

(71) Applicants: ADJUVANCE TECHNOLOGIES, INC., Lincoln, NE (US); MEMORIAL SLOAN KETTERING CANCER CENTER, New York, NY (US)

(72) Inventors: David Y. Gin, Lincoln, NE (US); Eric Chea, Oakland, CA (US); Alberto Fernandez-Tejada, Logroño (ES); Jeffrey Gardner, New York, NY (US); Jason Lewis, New York, NY (US); Philip Livingston, New York, NY (US); J. Tyler Martin, Roca, NE (US); Lars Nordstroem, New York, NY (US); Naga Vara Kishore Pillarsetty, Jackson Heights, NY (US); Govind Ragupathi, New York, NY (US); Derek Tan, New York, NY (US)

(73) Assignees: ADJUVANCE TECHNOLOGIES, INC., Lincoln, NE (US); MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,207

(22) Filed: Jun. 4, 2024

(65) Prior Publication Data

US 2024/0327443 A1 Oct. 3, 2024

Related U.S. Application Data

(63) Continuation of application No. 18/180,421, filed on Mar. 8, 2023, now Pat. No. 12,037,355, which is a continuation of application No. 17/005,110, filed on Aug. 27, 2020, now abandoned, which is a continuation of application No. 16/827,220, filed on Mar. 23, 2020, now Pat. No. 10,906,926, which is a continuation of application No. 15/774,081, filed as application No. PCT/US2016/060564 on Nov. 4, 2016, now abandoned.

(60) Provisional application No. 62/268,837, filed on Dec. 17, 2015, provisional application No. 62/252,296, filed on Nov. 6, 2015.

(51) Int. Cl.

| | |
|---|---|
| ***A61K 31/7024*** | (2006.01) |
| ***A61K 39/02*** | (2006.01) |
| ***A61K 39/08*** | (2006.01) |
| ***A61K 39/39*** | (2006.01) |
| ***A61P 31/04*** | (2006.01) |
| ***C07H 1/00*** | (2006.01) |
| ***C07H 13/04*** | (2006.01) |
| ***C07H 13/06*** | (2006.01) |
| ***C07H 13/08*** | (2006.01) |
| ***C07J 63/00*** | (2006.01) |
| *A61K 39/00* | (2006.01) |
| *A61K 39/10* | (2006.01) |

(52) U.S. Cl.

CPC .......... *C07H 1/00* (2013.01); *A61K 31/7024* (2013.01); *A61K 39/08* (2013.01); *A61K 39/099* (2013.01); *A61K 39/39* (2013.01); *A61P 31/04* (2018.01); *C07H 13/04* (2013.01); *C07H 13/06* (2013.01); *C07H 13/08* (2013.01); *C07J 63/008* (2013.01); *A61K 2039/10* (2013.01); *A61K 2039/55583* (2013.01)

(58) Field of Classification Search

USPC ........................................................ 514/25

See application file for complete search history.

(56) References Cited

U.S. PATENT DOCUMENTS

| | | | |
|---|---|---|---|
| 3,985,615 | A | 10/1976 | Kubo |
| 4,684,479 | A | 8/1987 | D'Arrigo |
| 5,215,680 | A | 6/1993 | D'Arrigo |
| 5,874,104 | A | 2/1999 | Adler-Moore et al. |
| 5,916,588 | A | 6/1999 | Popescu et al. |
| 5,965,156 | A | 10/1999 | Proffitt et al. |
| 6,008,203 | A | 12/1999 | Magnani et al. |
| 6,043,094 | A | 3/2000 | Martin et al. |
| 6,056,973 | A | 5/2000 | Allen et al. |
| 6,080,725 | A | 6/2000 | Marciani et al. |
| 6,126,966 | A | 10/2000 | Abra et al. |
| 6,262,029 | B1 | 7/2001 | Press et al. |

(Continued)

FOREIGN PATENT DOCUMENTS

| | | | |
|---|---|---|---|
| CL | 2011003113 | A1 | 8/2012 |
| CL | 2012000585 | A1 | 9/2012 |

(Continued)

OTHER PUBLICATIONS

Abbas Vafai, "Antibody-binding sites on truncated forms of varicella-zoster virus gpl(gE) glycoprotein", Vaccine, vol. 12, No. 14 (1994), pp. 1265-1269.

(Continued)

*Primary Examiner* — Traviss C Mcintosh, III

(74) *Attorney, Agent, or Firm* — Paul D. Strain, Esq.; Strain & Strain PLLC

(57) ABSTRACT

The present application relates to triterpene glycoside saponin-derived adjuvants, syntheses thereof, and intermediates thereto. The application also provides pharmaceutical compositions comprising compounds of the present invention and methods of using said compounds or compositions in the treatment of and immunization for infectious diseases.

17 Claims, 8 Drawing Sheets

(56) References Cited

U.S. PATENT DOCUMENTS

| | | | |
|---|---|---|---|
| 6,294,191 B1 | 9/2001 | Meers et al. | |
| 6,316,024 B1 | 11/2001 | Allen et al. | |
| 6,352,716 B1 | 3/2002 | Janoff et al. | |
| 6,406,713 B1 | 6/2002 | Janoff et al. | |
| 6,759,057 B1 | 7/2004 | Weiner et al. | |
| 8,283,456 B2 | 10/2012 | Gin et al. | |
| 8,889,842 B2 | 11/2014 | Gin et al. | |
| 9,718,850 B2 | 8/2017 | Gin et al. | |
| 10,906,926 B2 * | 2/2021 | Gin | C07H 1/00 |
| 11,324,821 B2 * | 5/2022 | Martin | A61K 39/00 |
| 12,037,355 B2 * | 7/2024 | Gin | C07H 13/08 |
| 2003/0095974 A1 | 5/2003 | Garcon et al. | |
| 2004/0208921 A1 | 10/2004 | Ho et al. | |
| 2009/0035360 A1 | 2/2009 | Lemoine | |
| 2009/0047306 A1 | 2/2009 | Nash et al. | |
| 2010/0272745 A1 | 10/2010 | Lemoine et al. | |
| 2010/0322958 A1 | 12/2010 | Bardotti et al. | |
| 2011/0104260 A1 | 5/2011 | Hanon et al. | |
| 2011/0206758 A1 | 8/2011 | Vandepapeliere | |
| 2012/0087976 A1 | 4/2012 | Henderickx et al. | |
| 2012/0164178 A1 | 6/2012 | Ballou, Jr. et al. | |
| 2013/0011421 A1 | 1/2013 | Gin et al. | |
| 2013/0309273 A1 | 11/2013 | Hassett et al. | |
| 2014/0072622 A1 | 3/2014 | Denoel et al. | |
| 2014/0228286 A1 | 8/2014 | Luippold et al. | |
| 2015/0037374 A1 | 2/2015 | Bazmorelli et al. | |
| 2015/0086585 A1 | 3/2015 | Gin et al. | |
| 2017/0014507 A1 | 1/2017 | Bazmorelli et al. | |
| 2017/0065715 A1 | 3/2017 | Vandepapeliere | |
| 2017/0096444 A1 | 4/2017 | Gin et al. | |
| 2018/0008700 A1 | 1/2018 | Heineman et al. | |
| 2018/0327436 A1 | 11/2018 | Gin et al. | |
| 2019/0275135 A1 | 9/2019 | Poolman | |
| 2020/0164065 A1 | 5/2020 | Gardner et al. | |
| 2020/0239509 A1 | 7/2020 | Gin et al. | |
| 2020/0261571 A1 | 8/2020 | Martin et al. | |
| 2020/0276299 A1 | 9/2020 | Fox et al. | |
| 2021/0002316 A1 | 1/2021 | Gin et al. | |
| 2021/0283248 A1 | 9/2021 | Livingston et al. | |
| 2022/0184207 A1 | 6/2022 | Martin et al. | |
| 2022/0409721 A1 | 12/2022 | Martin et al. | |
| 2023/0128815 A1 | 4/2023 | Martin et al. | |
| 2023/0219991 A1 | 7/2023 | Gin et al. | |
| 2023/0357300 A1 | 11/2023 | Chan et al. | |

FOREIGN PATENT DOCUMENTS

| | | |
|---|---|---|
| EP | 0 192 902 A2 | 9/1986 |
| JP | 2011-516566 A | 5/2011 |
| WO | WO 93/05789 A1 | 4/1993 |
| WO | WO 94/02596 A1 | 2/1994 |
| WO | WO 96/33739 A1 | 10/1996 |
| WO | WO 2001/015727 A2 | 3/2001 |
| WO | WO 2006/094756 A2 | 9/2006 |
| WO | WO 2009/080715 A2 | 7/2009 |
| WO | WO 2009/126737 A2 | 10/2009 |
| WO | WO 2010/142685 A1 | 12/2010 |
| WO | WO 2011/027222 A2 | 3/2011 |
| WO | WO 2012/158978 A1 | 11/2012 |
| WO | WO 2015/148648 A1 | 10/2015 |
| WO | WO 2015/184451 A1 | 12/2015 |
| WO | WO 2017/079582 A1 | 5/2017 |
| WO | WO 2017/106836 A1 | 6/2017 |
| WO | WO 2018/114892 A1 | 6/2018 |
| WO | WO 2018/191598 A1 | 10/2018 |
| WO | WO 2018/198085 A1 | 11/2018 |
| WO | WO 2018/200645 A1 | 11/2018 |
| WO | WO 2018/200656 A1 | 11/2018 |
| WO | WO 2019/079160 A1 | 4/2019 |
| WO | WO 2021/091997 A1 | 5/2021 |
| WO | WO 2021/195024 A1 | 9/2021 |
| WO | WO 2021/257884 A1 | 12/2021 |
| WO | WO 2022/221393 A1 | 10/2022 |

OTHER PUBLICATIONS

Abstract of Slingluff et al., Journal for Immuno Therapy of Cancer (Nov. 6, 2014), vol. 2, Suppl. 3, Abstract No. P60. 2 pgs.

Adams et al., "Design and Synthesis of Potent Quillaja Saponin Vaccine Adjuvants", J Am Chem Soc. 1939(2010), vol. 132 (6), pp. 1-16.

Adams, "Synthesis of Saponin Immunoadjuvants", University of Illinois at Urbana—Champaign, Ph.D. Dissertation 2009 [retrieved on Jul. 18, 2018). Retrieved from the Internet: <URL: https://search.proquest.com/docview/304896057>. See Abstract, pp. 45-47.

Alving et al., "Liposomal adjuvants for human vaccines", Expert Opinion on Drug Delivery (2016), vol. 13, No. 6, pp. 807-816Alving et al., "Liposomal adjuvants for human vaccines", Expert Opinion on Drug Delivery (2016), vol. 13, No. 6, pp. 807-816.

Arbeter et al., "Live attenuated varicella vaccine: Immunization of healthy children with the OKA strain", The Journal of Pediatrics, vol. 100, No. 6 (1982), pp. 886-893.

Arvin et al., "Equivalent recognition of a varicella-zoster virus immediate early protein (IE62) and glycoprotein I by cytotoxic T lymphocytes of either CD4+ or CD8+ phenotype", J Immunol, vol. 146 (1991), pp. 257-264.

Arvin et al., "Memory Cytotoxic T Cell Responses to Viral Tegument and Regulatory Proteins Encoded by Open Reading Frames 4, 10, 29, and 62 of Varicella-Zoster Virus", Viral Immunology, vol. 15, No. 3 (2002), pp. 507-516.

Balsevich et al., "Analysis of bisdesmosidic saponins in *Saponaria vaccaria* L. by HPLC-PAD-MS: identification of new quillaic acid and gypsogenin 3-O-Trisaccharides." Phytochemical analysis, vol. 17, No. 6, pp. 414-423 (Oct. 18, 2006) (https://doi.org/10.1002/pca.943).

Bautz, "OGEN: COVID-19 Vaccine Candidate Exhibits Protective Immunity in Mice . . . ", Zacks Small-Cap Research, Apr. 9, 2021 (Apr. 9, 2021) pp. 1-7.

Brichard, "Development of cancer vaccines with the MAGE-3 protein", Cancer Immunity (2005), vol. 5, Suppl. 1, p. 16Brichard, "Development of cancer vaccines with the MAGE-3 protein", Cancer Immunity (2005), vol. 5, Suppl. 1, p. 16.

Carcaboso et al., Potent, long lasting systematic antibody levels and mixed Th1/Th2 immune response after nasal immunization with malaria antigen loaded PLGA microparticles, Vaccine (2004), vol. 22, (11-12), pp. 1423-1432.

Chea etal., "Synthesis and Preclinical Evaluation of QS-21 Variants Leading to Simplified Vaccine Adjuvants and Mechanistic Probes", J Am Chem Soc. vol. 134, No. 32 (2012), 26 pgs.

Cibulski et al., "Novel ISCOMs from Quillaja brasiliensis saponins induce mucosal and systemic antibody production, T-cell responses and improved antigen uptake", Vaccine, vol. 34 (2016), pp. 1162-1171.

Coccia et al., "Cellular and molecular synergy in AS01-adjuvanted vaccines results in an early IFNγ response promoting vaccine immunogenicity", npj Vaccines, vol. 2 (2018), pp. 1-14.

Coplan et al., "Development of a Measure of the Burden of Pain Due to Herpes Zoster and Postherpetic Neuralgia for Prevention Trials: Adaptation of the Brief Pain Inventory", The Journal of Pain, vol. 5, No. 6 (2004), pp. 344-356.

Debrus et al., "Varicella-Zoster Virus Gene 63 Encodes an Immediate-Early Protein That Is Abundantly Expressed during Latency", Journal of Virology, vol. 69, No. 5 (1995), pp. 3240-3245.

Didierlaurent et al., "Adjuvant system AS01: helping to overcome the challenges of modern vaccines", Expert Review of Vaccines (2017), vol. 16, No. 1, pp. 55-63.

Evans et al., "QS-21 promotes an adjuvant effect allowing for reduced antigen dose during HIV-1 envelope subunit immunization in humans", Vaccine (2001), vol. 19, pp. 2080-2091.

Fernandez-Tejada et al., "Development of a minimal saponin vaccine adjuvant based on QS-21", Published in final edited form as: Nat Chem. vol. 6, No. 7 (2014), pp. 635-643.

Fernández-Tejada et al., "Development of Improved Vaccine Adjuvants Based on the Saponin Natural Product QS-21 through Chemical Synthesis", Accounts of Chemical Research (2016), vol. 49, pp. 1741-1756.

(56) References Cited

OTHER PUBLICATIONS

Fernández-Tejada et al., "Semisynthesis of Analogues of the Saponin Immunoadjuvant QS-21", Methods in Molecular Biology (2016), vol. 1494, pp. 45-71.
Fernández-Tejada et al., "Versatile Strategy for the Divergent Synthesis of Linear Oligosaccharide Domain Variants of Quillaja Saponin Vaccine Adjuvants", Chem Commun (2015), vol. 51 (73), pp. 13949-13952.
Fernandez-Tejada et al; "Design, synthesis, and immunologic evaluation of vaccine adjuvant conjugates based on QS-21 and tucaresol" Bioorganic & Medicinal Chemistry, vol. 22, No. 21 (2014), pp. 5917-5923.
Fernandez-Tejada et al; "Development of a Minimal Saponin Vaccine Adjuvant based on QS-21", Supplementary Information, Nature Chemistry, vol. 6 (2014), pp. S1-S135.
Fleck et al., "Saponins from Quillaja saponaria and Quillaja brasiliensis: Particular Chemical Characteristics and Biological Activities", Molecules (2019), vol. 24, No. 171, pp. 1-29.
Fox, "Squalene Emulsions for Parenteral Vaccine and Drug Delivery", Molecules (2009), vol. 14, pp. 3286-3312.
Garcon et al., "Understanding Modern Vaccines: Perspectives in Vaccinology", Vaccine Adjuvants (2011), vol. 1, No. 1, pp. 89-113.
Gilden et al., "Neurologic Complications of the Reactivation of Varicella-Zoster Virus", Engl J Med., vol. 342, No. 9 (2000), pp. 635-645.
Gin et al., "Enhancing Immunogenicity of Cancer Vaccines: QS-21 as an Immune Adjuvant", Curr Drug ther. (2011), vol. 6 (3), pp. 207-212.
Guo et al., "Triterpenoid Saponins From Quillaja Saponaria" Phytochemistry, vol. 48, No. 1, pp. 175-180 (1998).
Harlow and Lane, "Antibodies: A Laboratory Manual", Cold Spring Harbor Laboratory (1988), pp. 726, Biochemical Education, vol. 17, No. 4 (1989).
Haumont et al., "Purification, characterization and immunogenicity of recombinant varicella-zoster virus glycoprotein gE secreted by Chinese hamster ovary cells", Virus Research, vol. 40 (1996), pp. 199-204.
Huang et al., "Specific Lysis of Targets Expressing Varicella-Zoster Virus gpl or gplV by CD4+ Human T-Cell Clones", J. Virol., Vo. 66, No. 5 (1992), pp. 2664-2669.
International Search Report, PCT/US2022/024594, Jul. 20, 2022, 1 pg.
Kashala et al., "Safety, tolerability and immunogenicity of new formulations of the Plasmodium falciparum malaria peptide vaccine SPf66 combined with the immunological adjuvant QS-21", Vaccine (2002), vol. 20, pp. 2263-2277.
Kensil et al., "Separation and characterization of saponins with adjuvant activity from Quillaja saponaria Molina cortex", Journal of Immunology (1991), vol. 146 (2), pp. 431-437.
Kensil, "Saponins as Vaccine Adjuvants", Critical Reviews in Therapeutic Drug Carrier Systems (1996), vol. 13 (1&2), pp. 1-55.
Kensil et al., "QS-21: a water-soluble triterpene glycoside adjuvant", Expert Opinion on Investigational Drugs (1998), vol. 7, No. 9, pp. 1475-1482.
Kim et al., "Comparison of the effect of different immunological adjuvants on the antibody and T-cell response to Immunization with MUC1-KLH and GD3-KLH conjugate cancer vaccines", Vaccine (2000), vol. 18, pp. 597-603.
Livingston et al., "Cancer vaccines targeting carbohydrate antigens", Human Vaccines (May-Jun. 2006), vol. 2 (3), pp. 137-143.
Marin et al., "Prevention of Varicella: Recommendations of the Advisory Committee on Immunization Practices (ACIP)", MMWR Recomm Rep., vol. 56, No. RR-4 (2007); pp. 1-40.
Newman et al., "Saponin adjuvant induction of ovalbumin-specific CD8+ cytotoxic T lymphocyte responses", Journal of Immunology (1992), vol. 148, pp. 2357-2362.
Patra et al., "Alga-Produced Malaria Transmission-Blocking Vaccine Candidate Pfs25 Formulated with a Human Use-Compatible Potent Adjuvant Induces High-Affinity Antibodies That Block Plasmodium falciparum Infection of Mosquitoes", Infection and Immunity (2015), vol. 83, No. 5, pp. 1799-1808.
Ragupathi et al., "Natural and synthetic saponin adjuvant QS-21 for vaccines against cancer", Expert Rev Vaccines (2011), vol. 10 (4), pp. 463-470.
Ragupathi et al., "Preclinical Evaluation of the Synthetic Adjuvant SQS-21 and its Constituent Isomeric Saponins", Vaccine (2010), vol. 28 (26), pp. 4260-4267.
Rodriguez-Diaz et al., "Topical anti-inflammatory activity of quillaic acid from Quillaja saponaria Mol. and some derivatives", Journal of Pharmacy and Pharmacology (2011), vol. 63, pp. 718-724.
Sabella et al., "Immunization with the Immediate-Early Tegument Protein (Open Reading Frame 62) of Varicella-Zoster Virus Protects Guinea Pigs against Virus Challenge", Journal of Virology, vol. 67, No. 12 (1993), pp. 7673-7676.
Sasaki et al., "Induction of systemic and mucosal immune responses to human immunodeficiency virus type 1 by a DNA vaccine formulated with QS-21 saponin adjuvant via intramuscular and intranasal routes", Journal of Virology (Jun. 1998), vol. 72 (6), pp. 4931-4939.
Sawyer et al., "Detection of Varicella-Zoster Virus DNA in Air Samples from Hospital Rooms", J Infect Dis., vol. 169 (1994), pp. 91-94.
Senders et al., "1236. Safety and Immunogenicity of a 20-Valent Pneumococcal Conjugate Vaccine (PCV20) in Healthy Infants in the United States", Open Forum Infectious Diseases (Oct. 2020), vol. 7 (Suppl 1), p. S637.
Sharp et al., "Kinetics and Viral Protein Specificity of the Cytotoxic T Lymphocyte Response in Healthy Adults Immunized with Live Attenuated Varicella Vaccine", JID, vol. 165 (1992), pp. 852-858.
Slingluff et al., "A randomized pilot trial testing the safety and immunologic effects of a MAGE-A3 protein plus AS15 immunostimulant administered into muscle or into dermal/subcutaneous sites", Cancer Immunol Immunother (2016), vol. 65, pp. 25-36.
Soltysik et al., "Structure/function studies of QS-21 adjuvant: assessment of triterpene aldehyde and glucuronic acid roles in adjuvant function", Vaccine (1995), vol. 13 (15), pp. 1403-1410.
Toussi et al., "Immune Adjuvant Effect of Molecularly-defined Toll-Like Receptor Ligands", Vaccines (2014), vol. 2, pp. 323-353.
Van Setten et al., "Glycosyl compositions and structural characteristics of the potential immunoadjuvant active saponins in the Quillaja saponaria Mollina extract Quil A", Rapid Communications in Mass Spectrometry (1995), vol. 9, pp. 660-666.
Walkowicz et al., "Quillaja saponin variants with central glycosidic linkage modifications exhibit distinct conformations and adjuvant activities", Chem. Sci. (2016), vol. 7, pp. 2371-2380.
Wuts et al.; "Chapter 2: Protection for the Hydroxyl Group, Including 1,2- and 1,3-Diols", Greene's Protective Groups in Organic Synthesis, 4th Ed. (Dec. 31, 2006), 351 pgs.
Gin, U.S.PTO Office Action, U.S. Appl. No. 15/774,081, Oct. 16, 2019, 26 pgs.
Gin, U.S. PTO Notice of Allowance, U.S. Appl. No. 15/774,081, Mar. 3, 2020, 9 pgs.
Gin, U.S. PTO Office Action, U.S. Appl. No. 16/827,220, Apr. 28, 2020, 9 pgs.
Gin, U.S. PTO Notice of Allowance, U.S. Appl. No. 16/827,220, Aug. 19, 2020, 7 pgs.
Gin, U.S.PTO Office Action, U.S. Appl. No. 17/005,110, Feb. 11, 2022, 10 pgs.
Gin, U.S. PTO Office Action, U.S. Appl. No. 17/005,110, Oct. 4, 2021, 9 pgs.
Gin, U.S.PTO Office Action, U.S. Appl. No. 18/180,421, Oct. 10, 2023, 20 pgs.
Gin, U.S. PTO Notice of Allowance, U.S. Appl. No. 18/180,421, Mar. 5, 2024, 9 pgs.
Berge et al., "Pharmaceutical Salts", Journal of Pharmaceutical Sciences, vol. 66, No. 1 (1977), pp. 1-19.
Liu et al., "Prednisolone-Glucose Derivative Conjugate: Synthesis, Biodistribution and Pharmacodynamics Evaluation", Arch. Pharm. Chern. Life Sci. (2012), vol. 345, pp. 925-933.

(56) References Cited

OTHER PUBLICATIONS

Scott et al., "Mitsunobu Inversion of a Secondary Alcohol with Diphenylphosphoryl azide. Application to the Enantioselective Multikilogram Synthesis of a HCV Polymerase Inhibitor", Organic Process Research and Development (2011), vol. 15, pp. 1116-1123.
Squarcia et al., "Glycal-mediated syntheses of enantiomerically pure polyhydroxylated γ- and δ-lactams", Tetrahedron Letters (2002), vol. 43, pp. 4653-4655.
Wang, "Natural and Synthetic Saponins as Vaccine Adjuvants", Vaccines, vol. 9, No. 222 (2021), pp. 1-18.
Wojtczak, "Glossary of Medical Education Terms", Medical Teacher, vol. 24 (2002), pp. 1-24.
Wui et al., "Efficient induction of cell-mediated immunity to varicella-zoster virus glycoprotein E co-lyophilized with cationic liposome-based adjuvant in mice", Vaccine (2019), vol. 37, pp. 2131-2141.

* cited by examiner

P values: *<0.05, *<0.0002, and *<0.0001. NS=not significant

Statistics: Unpaired Mann-Whitney test.

Statistics: Unpaired Mann-Whitney test.

2 3 4

5 6 1

7 8

9 10 11

12 13 14 15

16 17

18

23

19

20

21

22

24

25

26 (TQL-1055)

TRITERPENE SAPONIN ANALOGUES

INCORPORATION BY REFERENCE OF RELATED PATENT APPLICATIONS

This application is a Continuation of U.S. application Ser. No. 18/180,421, filed Mar. 8, 2023, which is a Continuation of U.S. application Ser. No. 17/005,110, filed Aug. 27, 2020 (Abandoned), which is a Continuation of U.S. application Ser. No. 16/827,220, filed Mar. 23, 2020 (U.S. Pat. No. 10,906,926 on Feb. 2, 2021), which is a Continuation of U.S. application Ser. No. 15/774,081, filed May 7, 2018 (Abandoned), which is a National Stage of International Application No. PCT/US2016/060564, filed Nov. 4, 2016, which is based upon and claims the benefit of priority under U.S.C. § 119 (e) to U.S. Provisional Application No. 62/268,837, filed Dec. 17, 2015, and to U.S. Provisional Application No. 62/252,296, filed Nov. 6, 2015, the entire contents of all of which are incorporated herein by reference in their entirety.

GOVERNMENT SUPPORT

Some embodiments of the subject matter in this application were made with United States Government support under grant GRANT11540722 awarded by the National Institutes of Health. The United States Government has certain rights in the subject matter of this application.

FIELD OF THE INVENTION

The present application relates to triterpene glycoside saponin-derived adjuvants, syntheses thereof, and intermediates thereto. The application also provides pharmaceutical compositions comprising compounds of the present invention and methods of using said compounds or compositions in the treatment of infectious diseases.

BACKGROUND

Vaccines against infectious diseases continue to improve public health across the world. With increased knowledge of etiologic pathogens and necessary immune responses have come increasingly defined or targeted vaccines. Hepatitis B, DTaP, HPV, pneumococcal and other widely used vaccines require use of the immunological adjuvant alum. However, alum, which was introduced over 80 years ago, is a poor adjuvant restricting the potency of some of these vaccines and requiring higher or more doses of others. A leading candidate as a far more potent adjuvant than alum is the natural saponin adjuvant QS-21, used widely despite 3 major liabilities: dose limiting toxicity, poor stability, and limited availability of quality product.

Saponins are glycosidic compounds that are produced as secondary metabolites of steroids and triterpenes. They are widely distributed among plant species and in some marine invertebrates. The chemical structure of saponins imparts a wide range of pharmacological and biological activities, including some potent and efficacious immunological activity. Semi-purified saponin extracts from the bark of the South American *Quillaja saponaria* Molina tree (*Quillaja saponins*) exhibit remarkable immunoadjuvant activity. Because the *Quillaja saponins* are found as a mixture of at least one hundred structurally related saponin glycosides, their separation and isolation is often difficult if not prohibitive. The most active fraction of these extracts, designated QS-21, has been found to include a mixture of two principal isomeric triterpene glycoside saponins, each incorporating a quillaic acid triterpene core, flanked on either side by complex oligosaccharides and a stereochemically rich glycosylated fatty acyl chain.

The potency of QS-21 and its favorable toxicity profile in dozens of recent and ongoing vaccine clinical trials (melanoma, breast cancer, small cell lung cancer, prostate cancer, HIV-1, malaria) have established it as a promising new adjuvant for immune response potentiation and dose-sparing. However, the tolerated dose of QS-21 in cancer patients does not exceed 100-150 μg, above which significant local and systemic side effects arise. The highest practical tolerable dose in well (non-cancer) adult and child recipients is 25-50 mcg, an immunologically suboptimal dose. As a result, the clinical success of non-cancer vaccines continues to critically depend on the identification of, and access to, novel, potent adjuvants that are more tolerable.

Access to other potent *Quillaja saponins* has been hindered by difficulties in obtaining pure species from Quillaja saponin extracts. Furthermore, the structural identity of many *Quillaja saponins* remains only postulated. The discovery of new *Quillaja saponins* and related analogs with potent adjuvant activity and low toxicity presents a challenge to the fields of chemical synthesis and medicine.

SUMMARY

The present invention encompasses the recognition that the clinical use of QS-21 as an adjuvant is limited due to toxicity at higher doses, and that QS-7, a related Quillaja saponin, is difficult to isolate in pure form. Moreover, synthetic access to QS-21, QS-7, and other triterpene glycoside saponins is hindered by their structural complexity. The present application provides compounds that are analogs of QS-21 and QS-7.

In one aspect, the present application provides compounds of Formula I:

(I)

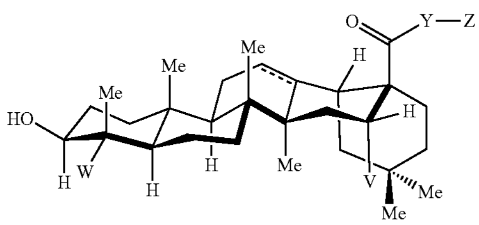

or a pharmaceutically acceptable salt thereof, wherein $\overline{\overline{\phantom{-}}}$ is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

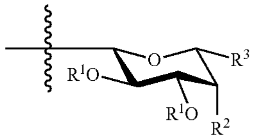

or

-continued

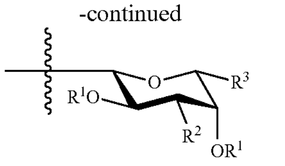

wherein each occurrence of $R^1$ is $R^x$ or a carbohydrate domain having the structure:

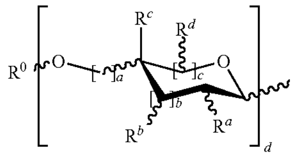

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

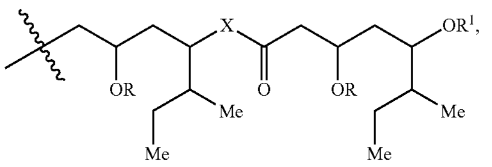

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

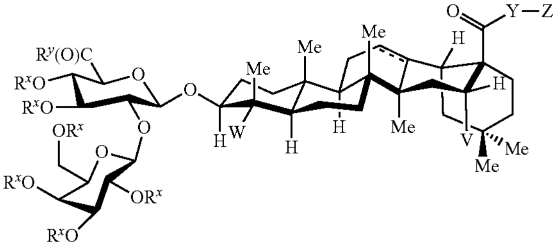

or a pharmaceutically acceptable salt thereof, wherein $\overline{\underline{---}}$ is a single or double bond;

W is ME, —CHO, or

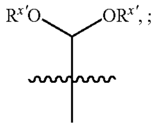

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

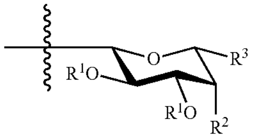

or

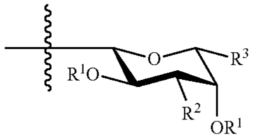

wherein each occurrence of $R^1$ is $R^x$ or a carbohydrate domain having the structure:

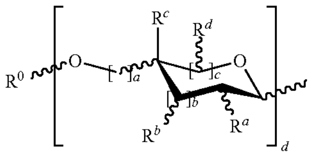

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur;

4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

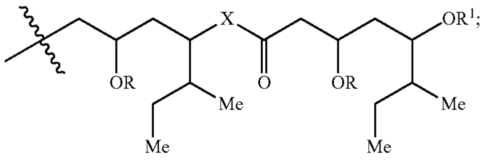

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur; each occurrence of $R^x$ is independently hydrogen or an oxygen protecting group selected from the group consisting of alkyl ethers, benzyl ethers, silyl ethers, acetals, ketals, esters, carbamates, and carbonates;

$R^Y$ is —OH, —OR, or a carboxyl protecting group selected from the group consisting of ester, amides, and hydrazides;

$R^s$ is

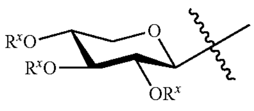

or

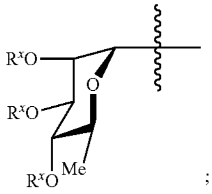

;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

It will be appreciated by one of ordinary skill in the art that the compounds of the present application include, but are not necessarily limited to, those compounds encompassed in the genus set forth herein. The compounds encompassed by this application include at least all of the compounds disclosed in the entire specification as a whole, including all individual species within each genus.

In another aspect, the present invention provides novel semi-synthetic methods for synthesizing QS-7, QS-21, and related analogs, the method comprising coupling a triterpene compound with a compound comprising a saccharide to form a compound of Formula II. In some embodiments, the method comprises the steps of:

(a) providing a compound of Formula III:

(III)

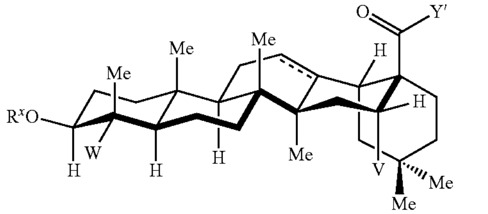

wherein:

$\overline{\underline{---}}$ is a single or double bond;

Y' is hydrogen, halogen, alkyl, aryl, OR, $OR^y$, OH, $NR_2$, $NR_3^+$, NHR, $NH_2$, SR, or NROR;

W is Me, —CHO, —$CH_2OR^x$, —$C(O)R^y$, or

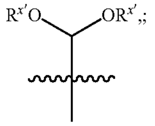

V is hydrogen or —$OR^x$;

$R^y$ is —OH, or a carboxyl protecting group selected from the group consisting of ester, amides, and hydrazides;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of Formula III under suitable conditions with a compound of Formula V:

LG-Z (V)

wherein:

Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

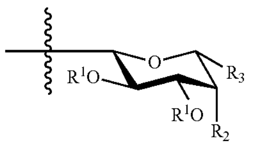

or

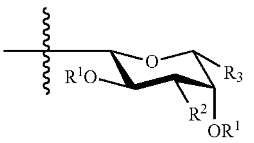

wherein:

each occurrence of $R^1$ is $R^x$ or a carbohydrate domain having the structure:

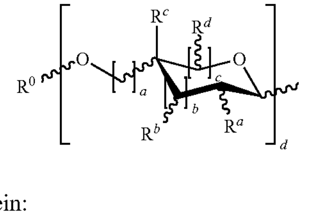

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

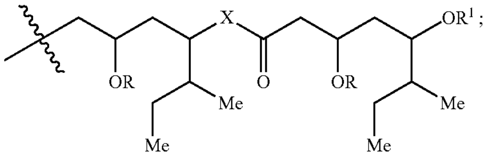

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^{1'}$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

$R^{1'}$ is $R^x$ or a carbohydrate domain having the structure:

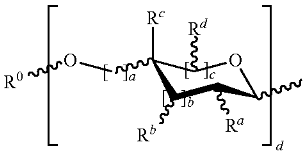

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

each occurrence of $R^x$ is as defined for compounds of Formula III; and

LG is a suitable leaving group selected from the group consisting of halogen, imidate, alkoxy, sulphonyloxy, optionally substituted alkylsulphonyl, optionally substituted alkenylsulfonyl, optionally substituted arylsulfonyl, and diazonium moieties;

(c) to give a compound of formula I as described herein.

In some embodiments, the method comprises the steps of:

(a) Providing a compound of Formula IV:

(IV)

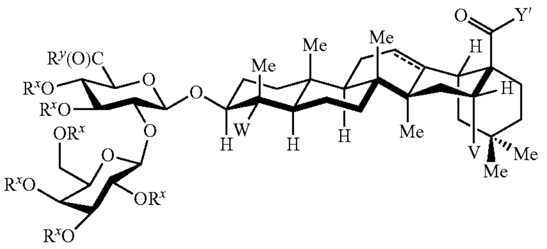

wherein:

⎓ is a single or double bond;

Y' is hydrogen, halogen, alkyl, aryl, OR, $OR^y$, OH, $NR_2$, $NR_3^+$, NHR, $NH_2$, SR, or NROR;

W is Me, —CHO, —$CH_2OR^x$, —$C(O)R^y$, or

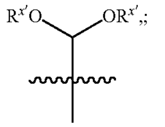

V is hydrogen or —$OR^x$;

$R^y$ is —OH, or a carboxyl protecting group selected from the group consisting of ester, amides, and hydrazides;

$R^s$ is

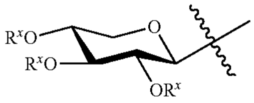

or

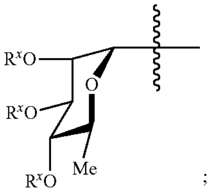

;

each occurrence of $R^{x'}$ is independently an optionally substituted group selected from 6-10-membered aryl, C1-6 aliphatic, or $C_{1-6}$ heteroaliphatic having 1-2 heteroatoms independently selected from the group consisting of nitrogen, oxygen, and sulfur; or: two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of Formula IV under suitable conditions with a compound of formula V:

LG-Z (V)

wherein:

Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

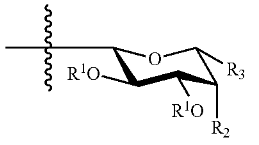

or

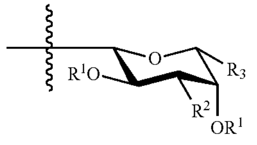

wherein:

each occurrence of R1 is Rx or a carbohydrate domain having the structure:

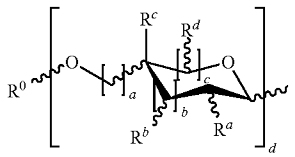

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

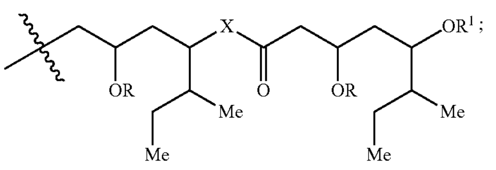

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^{1'}$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

$R^{1'}$ is $R^x$ or a carbohydrate domain having the structure:

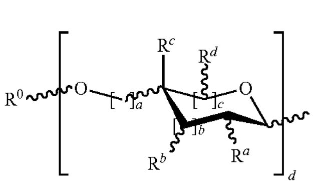

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

each occurrence of $R^x$ is as defined for compounds of formula IV; and

LG is a suitable leaving group selected from the group consisting of halogen, imidate, alkoxy, sulphonyloxy, optionally substituted alkylsulphonyl, optionally substituted alkenylsulfonyl, optionally substituted arylsulfonyl, and diazonium moieties;

(c) to give a compound of Formula II as described herein.

According to another aspect of the present subject matter, the compounds disclosed in this application have been shown to be useful as adjuvants. In another aspect, the present application provides a method for preparing compounds according to the embodiments of this application. In another aspect, the present invention provides a method of potentiating an immune response to an antigen, comprising administering to a subject a provided vaccine in an effective amount to potentiate the immune response of said subject to said antigen.

In another aspect, the present invention provides methods of vaccinating a subject, comprising administering a provided vaccine to said subject. In some embodiments, the subject is human. In some embodiments, the vaccine is administered as an injectable.

In another aspect, the invention provides pharmaceutical compositions comprising compounds of the invention and pharmaceutically acceptable excipients. In certain embodiments, the pharmaceutical composition is a vaccine comprising an antigen and an inventive adjuvant.

In another aspect, the invention provides kits comprising pharmaceutical compositions of inventive compounds. In some embodiments, the kits comprise prescribing information. In some embodiments, such kits include the combination of an inventive adjuvant compound and another immunotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of immunotherapy. In certain embodiments, the kit includes a sufficient quantity of a pharmaceutical composition to immunize a subject against an antigen long term.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent $C_{1-12}$ (or $C_{1-26}$, $C_{1-16}$, $C_{1-8}$) or saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —(CH2)n-, wherein n is a positive integer, preferably from 1 to 30, from 1 to 28, from 1 to 26, from 1 to 24, from 1 to 22, from 1 to 20, from 1 to 18, from 1 to 16, from 1 to 14, from 1 to 12, from 1 to 10, from 1 to 8, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, phenyl, biphenyl, naphthyl, anthracyl and the like, which may bear one or more substituents. Also, included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14n electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration by injection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically-acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and N+($C_{1-4}$alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Representative organic amines useful for the formation of base addition salts include ethylamine, diethylamine, ethylenediamine, ethanolamine, diethanolamine, piperazine and the like. (See, for example, Berge et al., supra).

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both α- and β-linked embodiments, and mixtures thereof, are contemplated by the present invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)-amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N',N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R$; $—(CH_2)_{0-4}OR$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$, which may be substituted with $R^\circ$; $—CH{=}CHPh$, which may be substituted with $R^\circ$; $—(CH_2)_{0-40}$ $(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR$, $—SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)\ NR^\circ_2$; $—P(O)_2R^\circ$; $—OP(O)R^\circ_2$; $—OP(O)R^\circ_2$; $—OP(O)(OR^\circ)_2$; $SiR^\circ_3$; $—(C_{1-4}$ straight or branched)alkylene)$O—N(R^\circ)_2$; or $—(C_{1-4}$ straight or branched)alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\Delta$, -(halo$R^\Delta$), $—(CH_2)_{0-2}OH$, $—(CH_2)_{0-2}OR^\Delta$, $—(CH_2)_{0-2}CH(OR^\Delta)_2$; $—O$(halo$R^\Delta$), $—CN$, $—N_3$, $—(CH_2)_{0-2}C(O)R^\Delta$, $—(CH_2)_{0-2}C(O)OH$, $—(CH_2)_{0-2}C(O)OR^\Delta$, $—(CH_2)_{0-2}SR^\Delta$, $—(CH_2)_{0-2}SH$, $—(CH_2)_{0-2}NH_2$, $—(CH_2)_{0-2}NHR^\Delta$, $—(CH_2)_{0-2}NR^\Delta_2$, $—NO_2$, $—SiR^\Delta_3$, $—OSiR^\Delta_3$, $—C(O)\ SR^\Delta$, $—(C_{1-4}$ straight or branched alkylene)$C(O)OR^\Delta$, or —SSR. wherein each $R^\Delta$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, $═NNR^+_2$, ═NNHC(O)R*, ═NNHC(O)OR*, $═NNHS(O)_2R^*$, ═NR*, ═NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^\Delta$, -(halo$R^\Delta$), —OH, $—OR^\Delta$, $—O$(halo$R^\Delta$), —CN, —C(O)OH, $—C(O)OR^\Delta$, $—NH_2$, $—NHR^\Delta$, $—NR_2$, or $—NO_2$, wherein each $R^\Delta$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of $R^\dagger$ are independently halogen, $—R^\Delta$, -(halo$R^\Delta$), —OH, $—OR^\Delta$, $—O$(halo$R^\Delta$), —CN, —C(O)OH, $—C(O)OR^\Delta$, $—NH_2$, $—NHR^\Delta$, $—NR^\Delta_2$, or $—NO_2$, wherein each $R^\Delta$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "enriched" as used herein refers to a mixture having an increased proportion of one or more species. In some embodiments, the mixture is "enriched" following a process that increases the proportion of one or more desired species in the mixture. In some embodiments, the desired species comprise(s) greater than 10% of the mixture. In some embodiments, the desired species comprise(s) greater than 25% of the mixture. In some embodiments, the desired species comprise(s) greater than 40% of the mixture. In some embodiments, the desired species comprise(s) greater than 60% of the mixture. In some embodiments, the desired species comprise(s) greater than 75% of the mixture. In some embodiments, the desired species comprise(s) greater than 85% of the mixture. In some embodiments, the desired species comprise(s) greater than 90% of the mixture. In some embodiments, the desired species comprise(s) greater than 95% of the mixture. Such proportions can be measured any number of ways, for example, as a molar ratio, volume to volume, or weight to weight.

The term "pure" refers to compounds that are substantially free of compounds of related non-target structure or chemical precursors (when chemically synthesized). This quality may be measured or expressed as "purity." In some embodiments, a target compound has less than about 30%, 20%, 10%, 5%, 2%, 1%, 0.5%, and 0.1% of non-target structures or chemical precursors. In certain embodiments, a pure compound of present invention is only one prosapogenin compound (i.e., separation of target prosapogenin from other prosapogenins).

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

Further objects, features, and advantages of the present application will become apparent form the detailed which is set forth below when considered together with the figures of drawing.

DETAILED DESCRIPTION OF CERTAIN EMBODIMENTS

Figure 1:
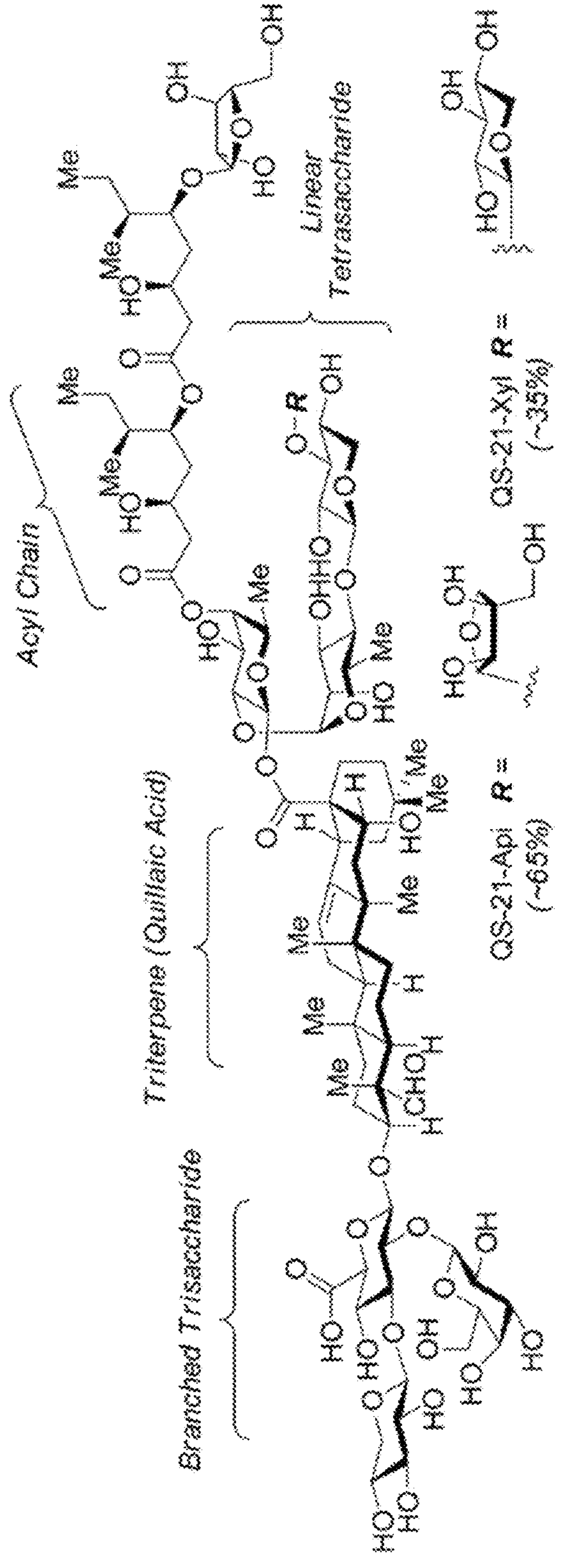
FIG. 1 depicts the chemical structure of QS-21-Api and QS-21-Xyl. Percentages correspond to the natural abundance of each isomer in isolated extracts of QS-21.

The clinical success of anticancer, antiviral and antimicrobial vaccines critically depends on the identification of, and access to, novel potent adjuvants with attenuated toxicity. In this context, specific fractions from extracts of the bark of *Quillaja saponaria* (QS) have proven to be exceedingly powerful adjuvants in immunotherapy. The QS-21 fraction (Kensil, C. R.; Patel, U.; Lennick, M.; Marciani, D. J. Immunol. 1991, 146, 431-437), comprising isomeric forms of a complex triterpene glycoside saponin (Soltysik, S.; Wu, J. Y.; Recchia, J.; Wheeler, D. A.; Newman, M. J.; Coughlin, R. T.; Kensil, C. R. Vaccine 1995, 13, 1403-1410; Kensil, C. R. Crit. Rev. Ther. Drug Carrier Syst. 1996, 13, 1-55), had previously been considered the most promising immuno-potentiator (Kim, S. K.; Ragupathi, G.; Musselli, C.; Choi, S. J.; Park, Y. S.; Livingston, P. O. Vaccine 2000, 18, 597-603) in several antitumor (melanoma, breast, small cell lung cancer, prostate) (Livingston, P. O.; Ragupathi, G. Hum. Vaccines 2006, 2, 137-143) and infectious-disease (HIV, malaria) vaccine therapies (Sasaki, S.; Sumino, K.; Hamajima, K.; Fukushima, J.; Ishii, N.; Kawamoto, S.; Mohri, H.; Kensil, C. R.; Okuda, K. J. Virol. 1998, 72, 4931-4939; Evans, T. G., et al. Vaccine 2001, 19, 2080-2091; Kashala, O., et al. Vaccine 2002, 20, 2263-2277; Carcaboso, A. M.; Hernandez, R. M.; Igartua, M.; Rosas, J. E.; Patarroyo, M. E.; Pedraz, J. L. Vaccine 2004, 22, 1423-1432).

However, the tolerated dose of QS-21 in cancer patients typically does not exceed 100-150 μg, above which significant local erythema and systemic flu-like symptoms arise. QS-21's inherent instability can lead to toxicities associated with its breakdown. It is also known that QS-21 is hemolytic, and this hemolytic activity had previously been hypothesized that at least some of QS-21's adjuvant activity was related to its hemolytic properties. Some of the various shortcomings of QS-21 have been partially addressed by formulation with emulsions (AS02 by GlaxoSmithKline (GSK) or liposomes (AS01, GSK)), however, these solutions are suboptimal and there remains a strong need for improved adjuvants that exhibit good adjuvant properties while maintaining a high degree of tolerability and/or reduced side-effects.

Now, surprisingly, the inventors of the present subject matter have found that compounds of the present application, which are in some embodiments synthetic analogues of QS-21 and other QS extraction fractions such as QS-7, possess significant stand-alone adjuvant activity as well as a high degree of tolerability and/or reduced side-effects. These new adjuvant compounds are more cost-effective to produce than natural QS-21, more stable, more efficacious, and less toxic for use in prophylactic and therapeutic vaccination programs. Some embodiments have no detectable toxicity in pharmacology/toxicology studies in mice at doses close to the likely 1000 mcg human dose. Some embodiments are surprisingly completely nonhemolytic while still retaining their adjuvant properties. This is surprising in part because it was initially thought that both QS-21 toxicity and potency were related to hemolysis and other cellular toxicity associated with QS-21. Some embodiments of the present application exhibit greater stability and less hemolytic activity by replacing the unstable ester linkage of the acyl chain in QS-21 with a very stable amide linkage, resulting in adjuvant active analogs of QS-21. Some embodiments also retain adjuvant activity despite having a simplified structure as compared to QS-21, resulting in higher synthetic yields and significantly reduced synthetic steps and cost of manufacture in comparison to synthetic QS-21.

The present application also provides efficient semi-synthetic methods of synthesizing the compounds of the present application, thereby significantly reducing the number of synthetic steps required to access this potent class of adjuvants.

The application also includes pharmaceutical compositions comprising the compounds of the present application together with an immunologically effective amount of an antigen associated with a bacterium or virus. Bacterium or viruses included in the subject matter of this application consist of those associated with Hepatitis B, pneumococcus, diphtheria, tetanus, pertussis, or Lyme disease including the closely related spirochetes of the genus *Borrelia* such as, *B. burgdorferi, B. garinii, B. afzelli*, and *B. japonica.*

The application also includes methods of vaccinating a human patient comprising administering an immunologically effective amount of a pharmaceutical compositions or of the compounds of the present application. The application also includes methods for increasing the immune response to a vaccine comprising administering an immunologically effective amount of a pharmaceutical compositions or of the compounds of the present application.

Compounds

Compounds of this invention include those described generally above, and are further illustrated by the classes, subclasses, and species disclosed herein. In some embodiments, provided compounds are analogs of naturally occurring triterpene glycoside saponins and intermediates thereto. For purposes of this invention, the chemical elements are identified in accordance with the Periodic Table of the Elements, CAS version, Handbook of Chemistry and Physics, 75th Ed. Additionally, general principles of organic chemistry are described in Organic Chemistry, Thomas Sorrell, University Science Books, Sausalito: 1999, and March's Advanced Organic Chemistry, 5th Ed., Ed.: Smith, M. B. and March, J., John Wiley & Sons, New York: 2001, the entire contents of which are hereby incorporated by reference.

Description of Exemplary Compounds

In some embodiments, provided compounds are analogs of *Quillaja saponins*. In some embodiments, provided compounds are prosapogenins. In certain embodiments, provided compounds are analogs of QS-7 and QS-21 and possess potent adjuvant activity.

In one aspect, the present application provides compounds of Formula I:

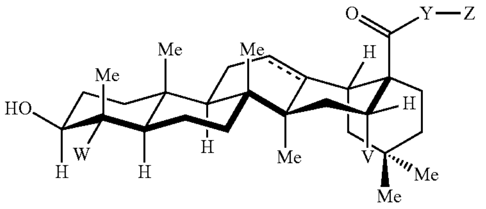

(I)

or a pharmaceutically acceptable salt thereof, wherein

⎓ is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

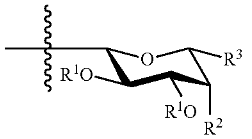

or

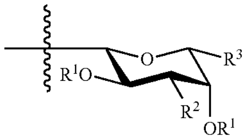

wherein each occurrence of $R^1$ is $R^x$ or a carbohydrate domain having the structure:

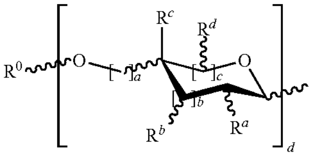

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

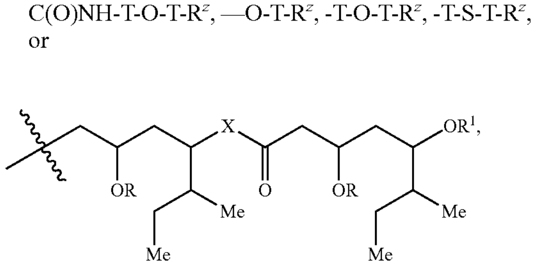

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

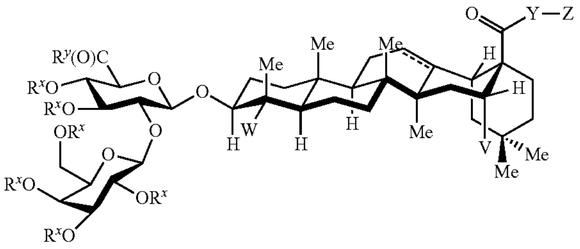

or a pharmaceutically acceptable salt thereof, wherein $\overline{\overline{---}}$ is a single or double bond;

W is ME, —CHO, or

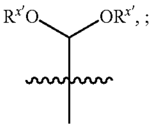

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

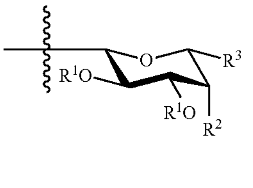

or

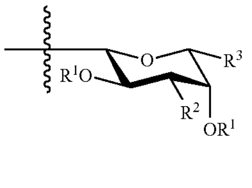

wherein each occurrence of $R^1$ is $R^x$ or a carbohydrate domain having the structure:

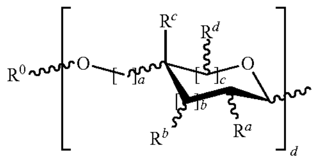

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

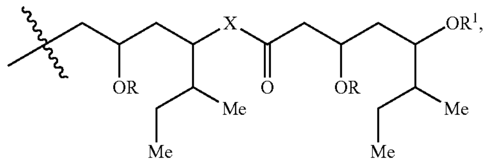

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^Y$ is —OH, —OR, or a carboxyl protecting group selected from the group consisting of ester, amides, and hydrazides;

$R^s$ is

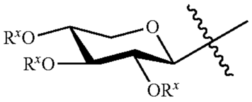

; or

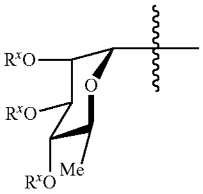

;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula I:

(I)

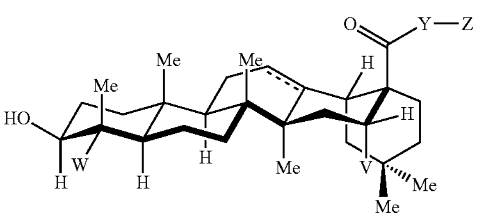

or a pharmaceutically acceptable salt thereof, wherein

⎓ is a single or double bond;
W is —CHO;
V is —OH;
Y is —O—;
wherein Z is a carbohydrate domain having the structure:

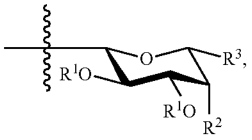

wherein:

$R^1$ is independently H or

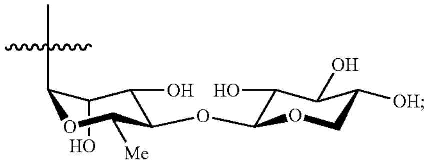

$R^2$ is $NHR^4$;
$R^3$ is $CH_2OH$; and
$R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

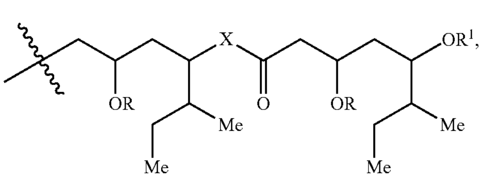

wherein:

X is —O—, —NR—, or $T-R^z$;
T is a covalent bond or a bivalent $C_{1-26}$ saturated or unsaturated, straight or branched, aliphatic or heteroaliphatic chain; and
$R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur.

It will be appreciated by one of ordinary skill in the art that the compounds of the present application include but are not necessarily limited to those compounds encompassed in the genus definitions set forth as part of the present section. The compounds encompassed by this application include at least all of the compounds disclosed in the entire specification as a whole, including all individual species within each genus.

In certain embodiments, V is $OR^x$. In certain embodiments V is OH. In certain embodiments, V is H.

In certain embodiments, Y is —O—. In certain embodiments, Y is —NH—. In certain embodiments, Y is —NR—. In certain embodiments, Y is $CH_2$.

In certain embodiments, Z is hydrogen. In certain embodiments, Z is a cyclic or acyclic, optionally substituted moiety. In certain embodiments, Z is an acyl. In certain embodiments, Z is an aliphatic. In certain embodiments, Z is a heteroaliphatic. In certain embodiments, Z is aryl. In certain embodiments Z is arylalkyl. In certain embodiments, Z is heteroacyl. In certain embodiments, Z is heteroaryl. In certain embodiments, Z is a carbohydrate domain having the structure:

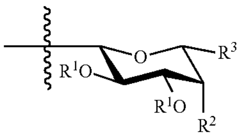

or

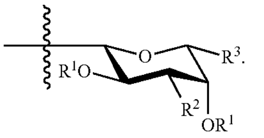

In some embodiments Z is a carbohydrate domain having the structure:

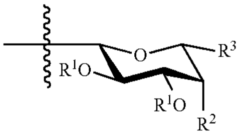

wherein:

$R^1$ is independently H or

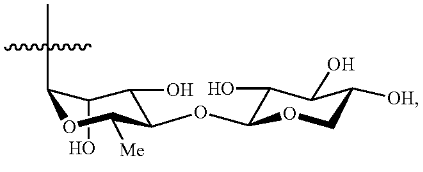

$R^2$ is $NHR^4$,
$R^3$ is $CH_2OH$, and
$R^4$ is selected from:

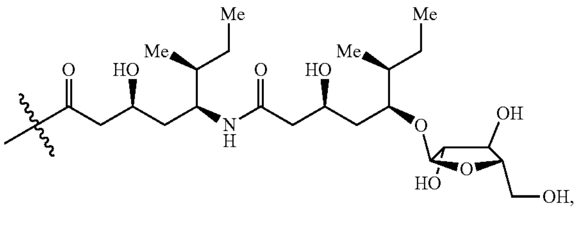

-continued

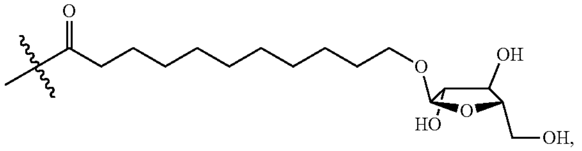

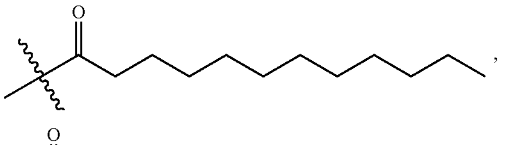

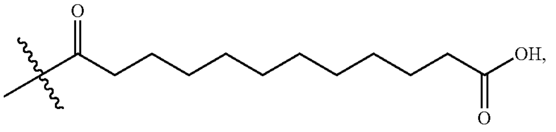

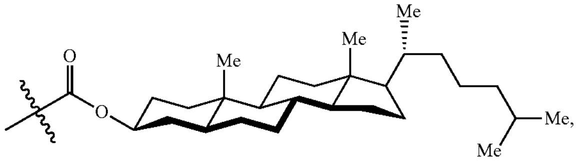

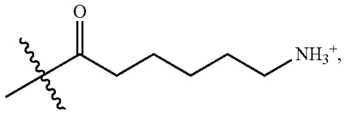

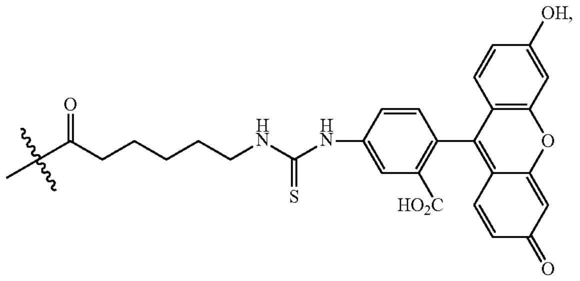

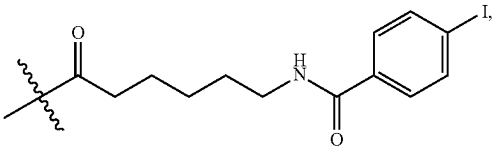

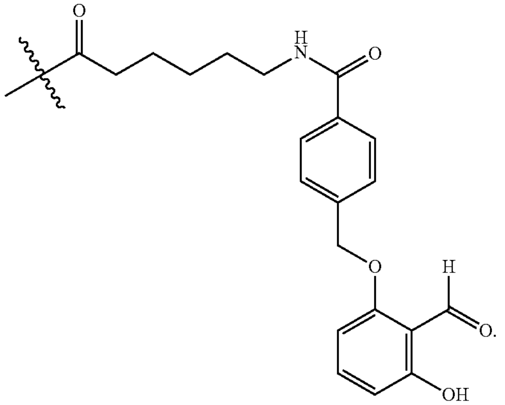

In some embodiments, $R^1$ is $R^x$. In other embodiments, $R^1$ a carbohydrate domain having the structure:

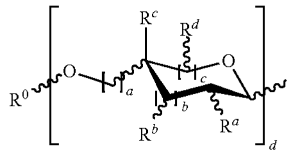

In some aspects, each occurrence of a, b, and c is independently 0, 1, or 2. In some embodiments, d is an integer from 1-5. In some embodiments, each d bracketed structure may be the same. In some embodiments, each d bracketed structure may be different. In some embodiments, the d bracketed structure represents a furanose or a pyranose moiety. In some embodiments, and the sum of b and c is 1 or 2.

In some embodiments, $R^0$ is hydrogen. In some embodiments, $R^0$ is an oxygen protecting group selected from the group. In some embodiments, $R^0$ is an alkyl ether. In some embodiments, $R^0$ is a benzyl ether. In some embodiments, $R^0$ is a silyl ether. In some embodiments, $R^0$ is an acetal. In some embodiments, $R^0$ is ketal. In some embodiments, $R^0$ is an ester. In some embodiments, $R^0$ is a carbamate. In some embodiments, $R^0$ is a carbonate. In some embodiments, $R^0$ is an optionally substituted moiety. In some embodiments, $R^0$ is an acyl. In some embodiments, $R^0$ is a $C_{1-10}$ aliphatic. In some embodiments, $R^0$ is a $C_{1-6}$ heteroaliphatic. In some embodiments, $R^0$ is a 6-10-membered aryl. In some embodiments, $R^0$ is a arylalkyl. In some embodiments, $R^0$ is a 5-10 membered heteroaryl having 1-4 heteroatoms independently selected from nitrogen, oxygen, or sulfur. In some embodiments, $R^0$ is a 4-7 membered heterocyclyl having 1-2 heteroatoms independently selected from the group consisting of nitrogen, oxygen, and sulfur.

In some embodiments, $R^a$ is hydrogen. In some embodiments, $R^a$ is a halogen. In some embodiments, $R^a$ is OH. In some embodiments, $R^a$ is OR. In some embodiments, $R^a$ is $OR^x$. In some embodiments, $R^a$ is $NR_2$. In some embodiments, $R^a$ is NHCOR. In some embodiments, $R^a$ an acyl. In some embodiments, $R^a$ is $C_{1-10}$ aliphatic. In some embodiments, $R^a$ is $C_{1-6}$ heteroaliphatic. In some embodiments, $R^a$ is 6-10-membered aryl. In some embodiments, $R^a$ is arylalkyl. In some embodiments, $R^a$ is 5-10-membered heteroaryl having 1-4 heteroatoms independently selected from nitrogen, oxygen, sulfur. In some embodiments, $R^a$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^c$ is hydrogen. In some embodiments, $R^c$ is a halogen. In some embodiments, $R^c$ is OH. In some embodiments, $R^c$ is OR. In some embodiments, $R^c$ is $OR^x$. In some embodiments, $R^c$ is $NR_2$. In some embodiments, $R^c$ is NHCOR. In some embodiments, $R^c$ an acyl. In some embodiments, $R^c$ is $C_{1-10}$ aliphatic. In some embodiments, $R^c$ is $C_{1-6}$ heteroaliphatic. In some embodiments, $R^c$ is 6-10-membered aryl. In some embodiments, $R^c$ is arylalkyl. In some embodiments, $R^c$ is 5-10-membered heteroaryl having 1-4 heteroatoms independently selected from nitrogen, oxygen, sulfur. In some embodiments, $R^c$ is 4-7-membered heterocyclyl having 1-2 heteroatoms independently selected from the group consisting of nitrogen, oxygen, and sulfur.

In some embodiments, $R^d$ is hydrogen. In some embodiments, $R^d$ is a halogen. In some embodiments, $R^d$ is OH. In some embodiments, $R^d$ is OR. In some embodiments, $R^d$ is $OR^x$. In some embodiments, $R^d$ is $NR_2$. In some embodiments, $R^d$ is NHCOR. In some embodiments, $R^d$ an acyl. In some embodiments, $R^d$ is $C_{1-10}$ aliphatic. In some embodiments, $R^d$ is $C_{1-6}$ heteroaliphatic. In some embodiments, $R^d$ is 6-10-membered aryl. In some embodiments, $R^d$ is arylalkyl. In some embodiments, $R^d$ is 5-10-membered heteroaryl having 1-4 heteroatoms independently selected from nitrogen, oxygen, sulfur. In some embodiments, $R^d$ is 4-7-membered heterocyclyl having 1-2 heteroatoms independently selected from the group consisting of nitrogen, oxygen, and sulfur.

In some embodiments, $R^2$ is hydrogen. In some embodiments, $R^2$ is a halogen. In some embodiments, $R^2$ is OH. In some embodiments, $R^2$ is OR. In some embodiments, $R^2$ is $OC(O)R^4$. In some embodiments, $R^2$ is $OC(O)OR^4$. In some embodiments, $R^2$ is $OC(O)NHR^4$. In some embodiments, $R^2$ is $OC(O)NRR^4$. In some embodiments, $R^2$ is $OC(O)SR^4$. In some embodiments, $R^2$ is $NHC(O)R^4$. In some embodiments, $R^2$ is $NRC(O)R^4$. In some embodiments, $R^2$ is $NHC(O)OR^4$. In some embodiments, $R^2$ is $NHC(O)NHR^4$. In some embodiments, $R^2$ is $NHC(O)NRR^4$. In some embodiments, $R^2$ is $NHR^4$. In some embodiments, $R^2$ is $N(R^4)_2$. In some embodiments, $R^2$ is $NHR^4$. In some embodiments, $R^2$ is $NRR^4$. In some embodiments, $R^2$ is $N_3$. In some embodiments, $R^2$ is $C_{1-10}$ aliphatic. In some embodiments, $R^2$ is $C_{1-6}$ heteroaliphatic. In some embodiments, $R^2$ is 6-10-membered aryl. In some embodiments, $R^2$ is arylalkyl. In some embodiments, $R^2$ is 5-10 membered heteroaryl having 1-4 heteroatoms independently selected from the group consisting of nitrogen, oxygen, and sulfur. In some embodiments, $R^2$ is 4-7-membered heterocyclyl having 1-2 heteroatoms independently selected from the group consisting of nitrogen, oxygen, and sulfur.

In some embodiments, $R^3$ is hydrogen. In some embodiments, $R^3$ is a halogen. In some embodiments, $R^3$ is $CH_2OR^1$. In some embodiments, $R^3$ is an acyl. In some embodiments, $R^3$ is $C_{1-10}$ aliphatic. In some embodiments, $R^3$ is $C_{1-6}$ heteroaliphatic. In some embodiments, $R^3$ is 6-10-membered aryl. In some embodiments, $R^3$ is arylalkyl. In some embodiments, $R^3$ is 5-10-membered heteroaryl having 1-4 heteroatoms independently selected from the group consisting of nitrogen, oxygen, and sulfur. In some embodiments, $R^3$ is 4-7-membered heterocyclyl having 1-2 heteroatoms independently selected from the group consisting of nitrogen, oxygen, and sulfur.

In some embodiments, $R^4$ is $-T-R^z$. In some embodiments, $R^4$ is $—C(O)-T-R^z$. In some embodiments, $R^4$ is $—NH-T-R^z$. In some embodiments, $R^4$ is $—O-T-R^z$. In some embodiments, $R^4$ is $—S-T-R^z$. In some embodiments, $R^4$ is $—C(O)NH-T-R^z$. In some embodiments, $R^4$ is $C(O)O-T-R^z$. In some embodiments, $R^4$ is $C(O)S-T-R^z$. In some embodiments, $R^4$ is $C(O)NH-T-O-T-R^z$. In some embodiments, $R^4$ is $—O-T-R^z$. In some embodiments, $R^4$ is $-T-O-T-R^z$. In some embodiments, $R^4$ is $-T-S-T-R^z$. In some embodiments, $R^4$ is

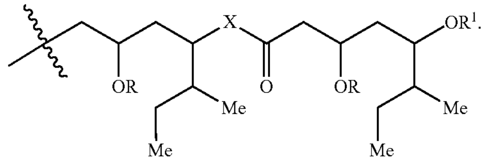

In some embodiments, X is —O—. In some embodiments, X is —NR—. In some embodiments, X is $T-R^z$.

In some embodiments, T is a covalent bond or a bivalent $C_{1-26}$ saturated or unsaturated, straight or branched, aliphatic or heteroaliphatic chain.

In some embodiments, $R^z$ is hydrogen. In some embodiments, $R^z$ is a halogen. In some embodiments, $R^z$ is —OR. In some embodiments, $R^z$ is $—OR^x$. In some embodiments, $R^z$ is $—OR^1$. In some embodiments, $R^z$ is $—OR^{1'}$. In some embodiments, $R^z$ is —SR. In some embodiments, $R^z$ is $NR_2$. In some embodiments, $R^z$ is —C(O)OR. In some embodiments, $R^z$ is —C(O)R. In some embodiments, $R^z$ is —NHC(O)R. In some embodiments, $R^z$ is —NHC(O)OR. In some embodiments, $R^z$ is NC(O)OR. In some embodiments, $R^z$ is an acyl. In some embodiments, $R^z$ is arylalkyl. In some embodiments, $R^z$ is heteroarylalkyl. In some embodiments, $R^z$ is $C_{1-6}$ aliphatic. In some embodiments, $R^z$ is 6-10-membered aryl. In some embodiments, $R^z$ is 5-10-membered heteroaryl having 1-4 heteroatoms independently selected from nitrogen, oxygen, or sulfur. In some embodiments, $R^z$ is 4-7-membered heterocyclyl having 1-2 heteroatoms independently selected from the group consisting of nitrogen, oxygen, and sulfur.

In some embodiments, $R^x$ is hydrogen. In some embodiments, $R^x$ is an oxygen protecting group. In some embodiments, $R^x$ is an alkyl ethers. In some embodiments, $R^x$ is a benzyl ether. In some embodiments, $R^x$ is silyl ether. In some embodiments, $R^x$ is an acetal. In some embodiments, $R^x$ is ketal. In some embodiments, $R^x$ is ester. In some embodiments, $R^x$ is carbamate. In some embodiments, $R^x$ is carbonate.

In some embodiments, $R^y$ is —OH. In some embodiments, $R^y$ is —OR. In some embodiments, $R^y$ is a carboxyl protecting group. In some embodiments, $R^y$ is an ester. In some embodiments, $R^y$ is an amide. In some embodiments, $R^y$ is a hydrazide.

In some embodiments, $R^s$ is

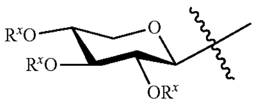

or

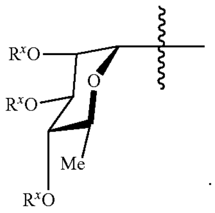

.

In some embodiments, $R^{x'}$ is optionally substituted 6-10-membered aryl. In some embodiments, $R^{x'}$ is optionally substituted $C_{1-6}$ aliphatic. In some embodiments, $R^{x'}$ is optionally substituted or $C_{1-6}$ heteroaliphatic having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, R is hydrogen. In some embodiments, R is an acyl. In some embodiments, R is arylalkyl. In some embodiments, R is 6-10-membered aryl. In some embodiments, R is $C_{1-6}$ aliphatic. In some embodiments, R is $C_{1-6}$ heteroaliphatic having 1-2 heteroatoms independently selected from the group consisting of nitrogen, oxygen, and sulfur. In some embodiments, two R on the same nitrogen atom are taken with the nitrogen atom to form a 4-7-membered heterocyclic ring having 1-2 heteroatoms independently selected from the group consisting of nitrogen, oxygen, and sulfur.

In some embodiments, $R^{1'}$ has the same embodiments as $R^1$. Exemplary compounds of Formula I are set forth in Table 1 below:

TABLE 1

EXEMPLARY COMPOUNDS OF FORMULA I

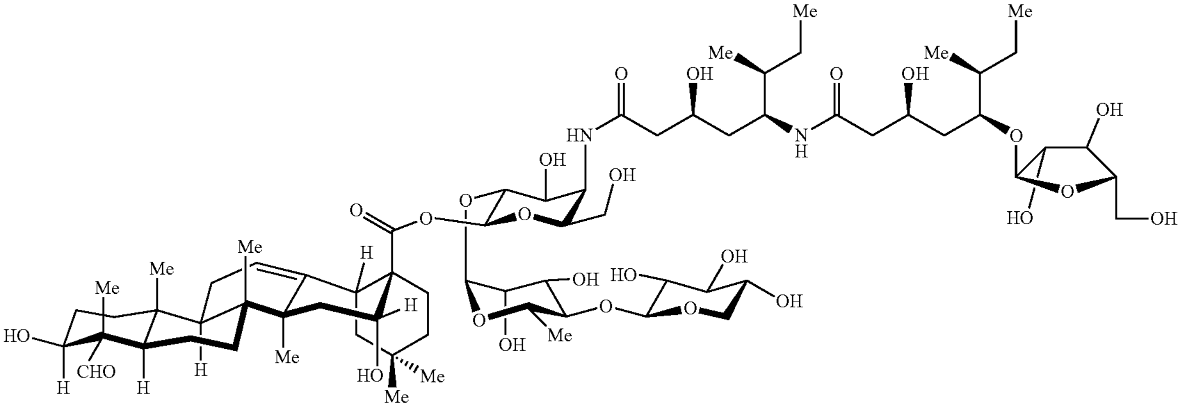

I-1

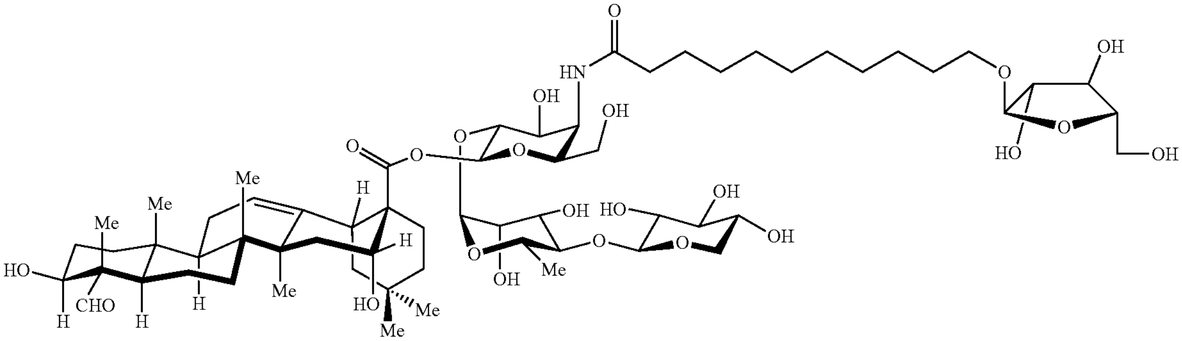

I-2

TABLE 1-continued
| EXEMPLARY COMPOUNDS OF FORMULA I |
| --- |
| 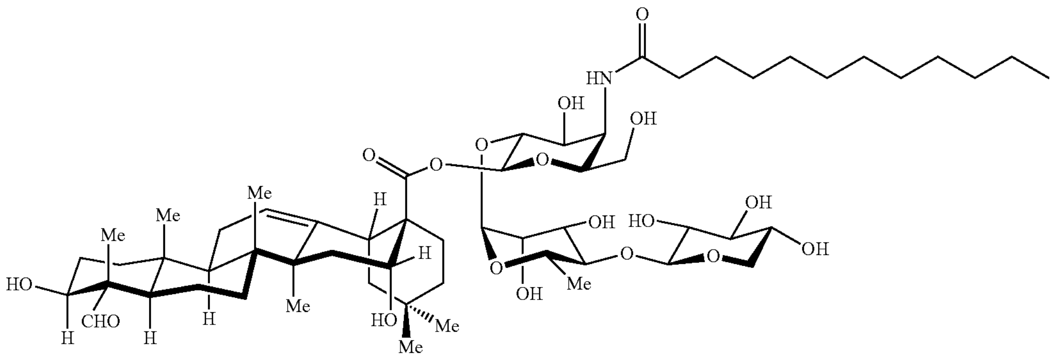 |
| I-3 |
| 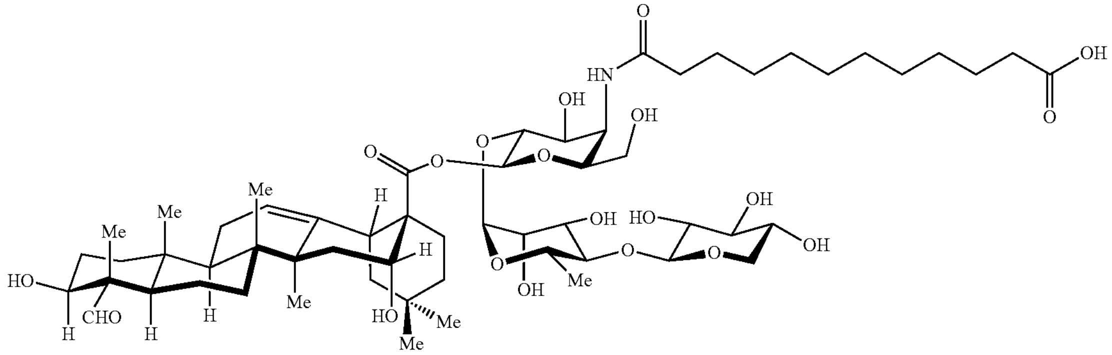 |
| I-4 |
| 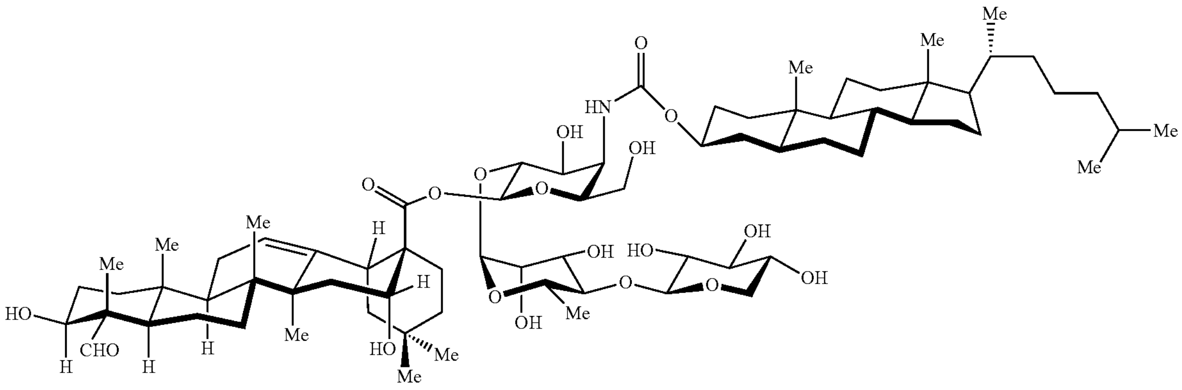 |
| I-5 |
| 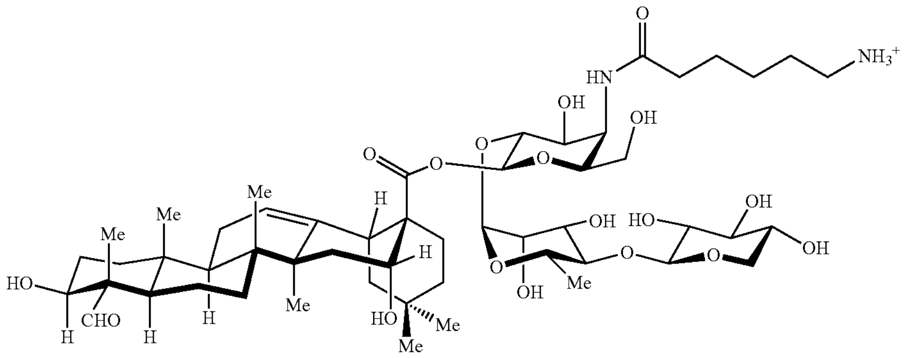 |
| I-6 |

TABLE 1-continued

EXEMPLARY COMPOUNDS OF FORMULA I

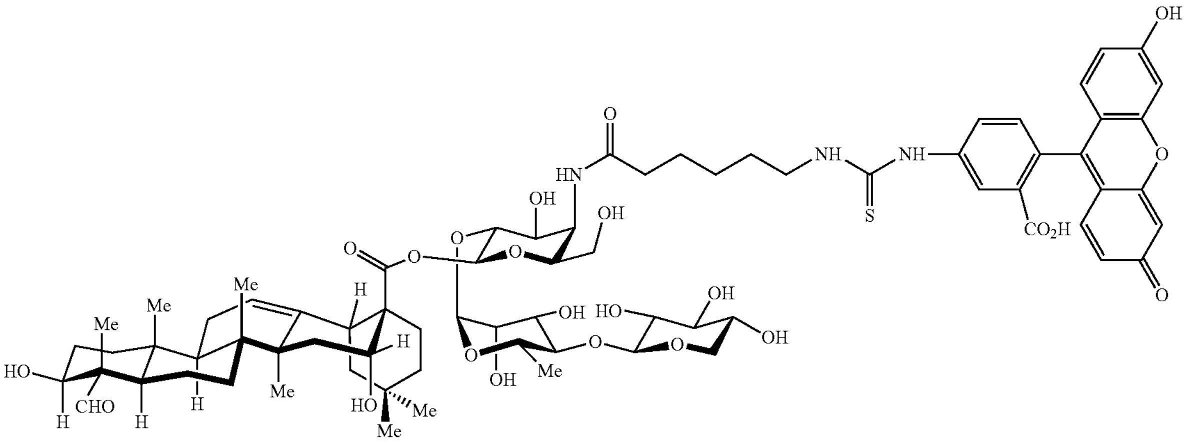

I-7

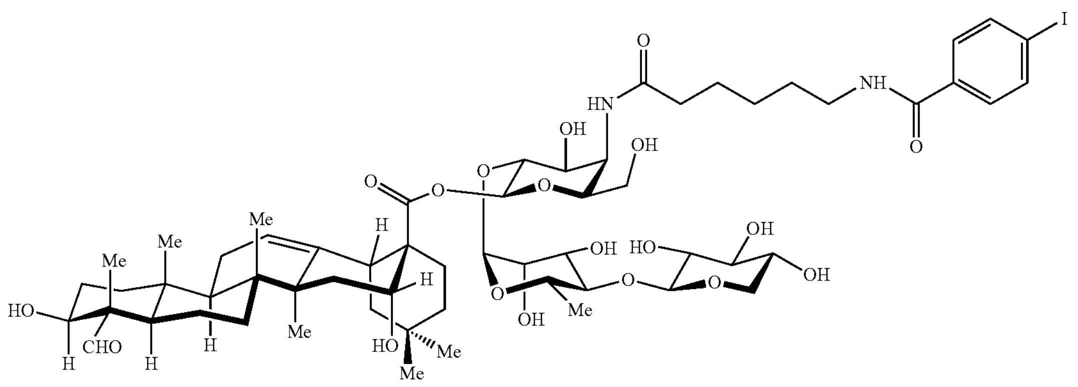

I-8

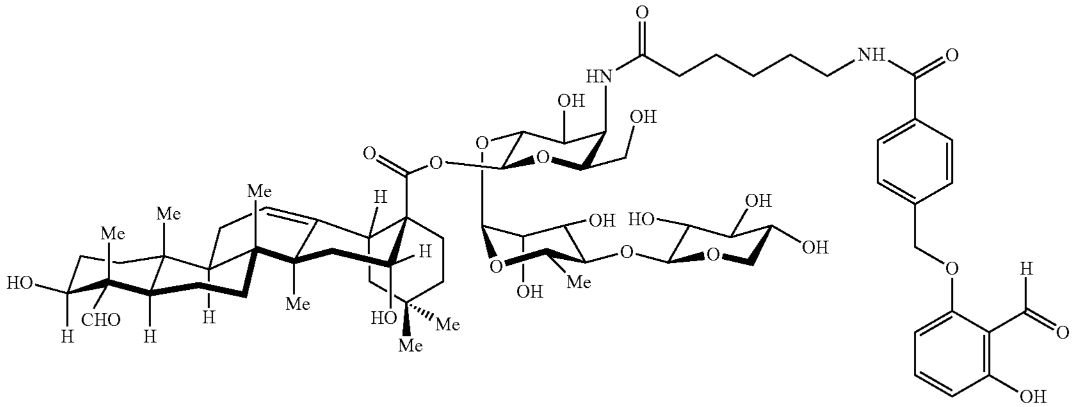

I-9

It will be appreciated that it is not an object of the present subject matter to claim compounds disclosed in the prior art that are the result of isolation or degradation studies on naturally occurring prosapogenins or *saponins.*

Synthesis of Compounds

As described in U.S. Ser. No. 12/420,803, issued as U.S. Pat. No. 8,283,456 (and its parent/child U.S. applications and publications), the synthesis of QS-21 and at least some of its analogues can be carried out in part by obtaining semi-purified abstract from *Quillaja saponaria* (commercially available as Quil-A, Accurate Chemical and Scientific Corporation, Westbury, NY) comprising a mixture of at least 50 distinct saponin species (van Setten, D. C.; Vandewerken, G.; Zomer, G.; Kersten, G. F. A. *Rapid Commun. Mass Spectrom.* 1995, 9, 660-666). Many of said saponin species include a triterpene-trisaccharide substructure as found in immunologically-active *Quillaja saponins* such as QS-21 and QS-7. Exposing these saponin species to base hydrolysis affords a mixture enriched with prosapogenins A, B, and C (shown below).

A

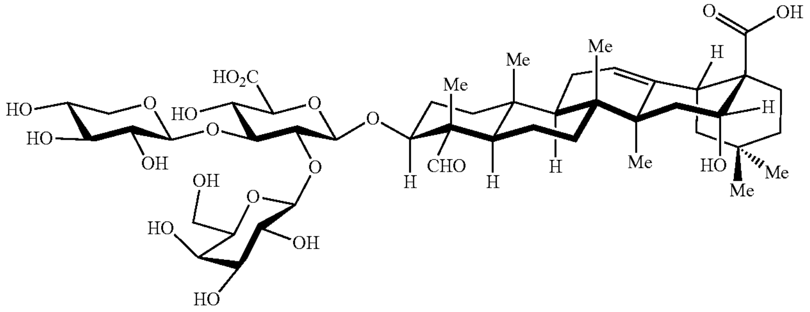

B

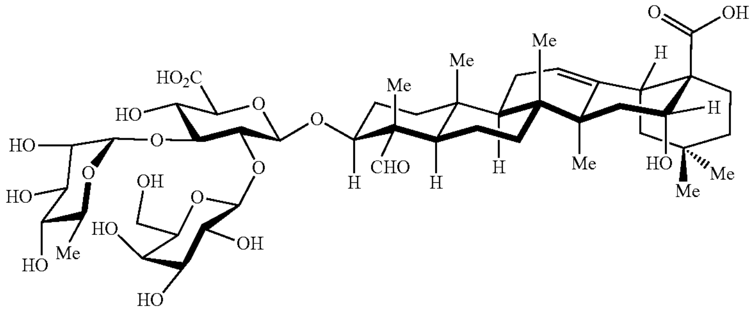

C

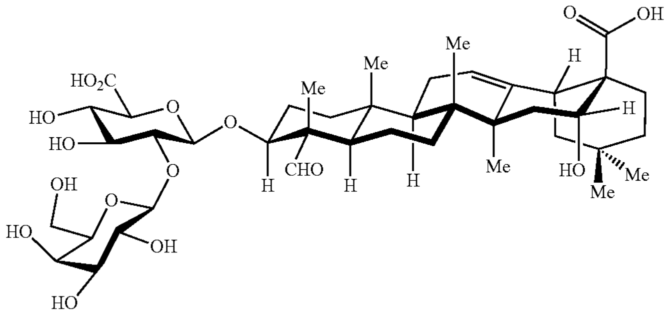

U.S. Ser. No. 12/420,803, issued as U.S. Pat. No. 8,283,456 (and its parent/child U.S. applications and publications) presents a strategy that allows for the facile separation of derivatized prosapogenins A, B, and C via silica gel chromatography. It will be appreciated that some embodiments of the present application may be synthesized in part using the methods described in U.S. Ser. No. 12/420,803, issued as U.S. Pat. No. 8,283,456 (and its parent/child U.S. applications and publications), particularly the methods relating to facile separation of derivatized prosapogenins A, B, and C. In one aspect, separated derivatized prosapogenins A, B, and/or C may then be used to synthesize QS-21 or analogs thereof using the methods described herein.

In one embodiment, the present application provides semi-synthetic methods for synthesizing QS-7, QS-21, and related analogs, the method comprising coupling a triterpene compound with a compound comprising a saccharide to form a compound of Formula I or of Formula II. In some embodiments, the method comprises the steps of:

(a) Providing a compound of Formula III:

(III)

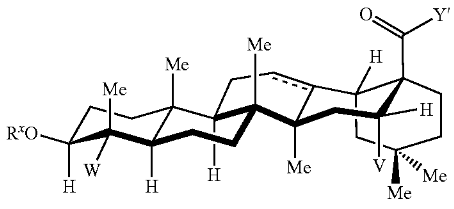

wherein:

$\overset{-}{=}$ is a single or double bond;

Y' is hydrogen, halogen, alkyl, aryl, OR, $OR^y$, OH, $NR_2$, $NR_3^+$, NHR, $NH_2$, SR, or NROR;

W is Me, —CHO, —$CH_2OR^x$, —$C(O)R^y$, or

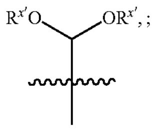

V is hydrogen or —$OR^x$;

$R^y$ is —OH, or a carboxyl protecting group selected from the group consisting of ester, amides, and hydrazides;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of Formula III under suitable conditions with a compound of formula V:

LG-Z (V)

wherein:

Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

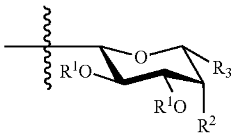

or

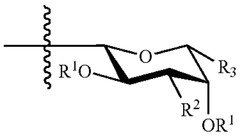

wherein:

each occurrence of R1 is Rx or a carbohydrate domain having the structure:

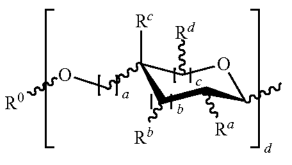

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

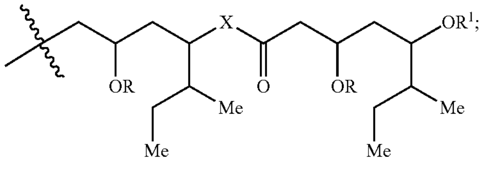

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is as defined for compounds of formula III; and

LG is a suitable leaving group selected from the group consisting of halogen, imidate, alkoxy, sulphonyloxy, optionally substituted alkylsulphonyl, optionally substituted alkenylsulfonyl, optionally substituted arylsulfonyl, and diazonium moieties;

(c) to give a compound of Formula I as described herein.

In some embodiments, the method comprises the steps of:

(a) Providing a compound of Formula IV:

(IV)

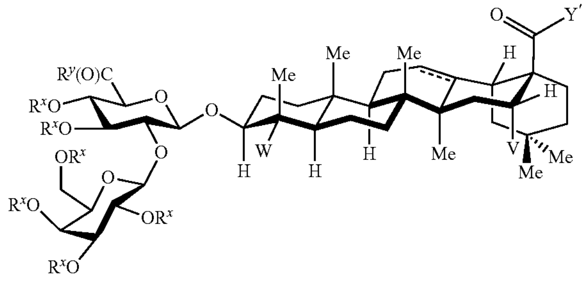

wherein

---- is a single or double bond;

Y' is hydrogen, halogen, alkyl, aryl, OR, $OR^y$, OH, $NR_2$, $NR_3^+$, NHR, $NH_2$, SR, or NROR;

W is Me, —CHO, —$CH_2OR^x$, —$C(O)R^y$, or

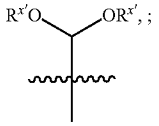

V is hydrogen or —$OR^x$;

$R^y$ is —OH, or a carboxyl protecting group selected from the group consisting of ester, amides, and hydrazides;

$R^s$ is

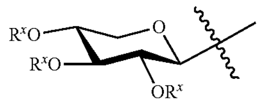

or

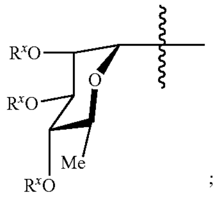

;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of Formula IV under suitable conditions with a compound of formula V:

LG-Z (V)

wherein:

Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

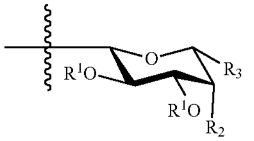

or

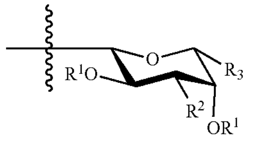

wherein:

each occurrence of R1 is Rx or a carbohydrate domain having the structure:

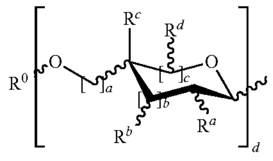

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)$ 2, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

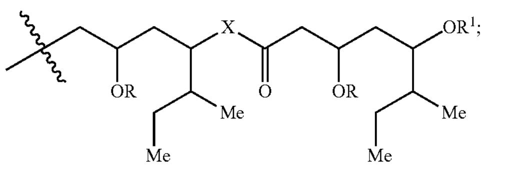

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is as defined for compounds of formula IV; and

LG is a suitable leaving group selected from the group consisting of halogen, imidate, alkoxy, sulphonyloxy, optionally substituted alkylsulphonyl, optionally substituted alkenylsulfonyl, optionally substituted arylsulfonyl, and diazonium moieties;

(c) to give a compound of formula II as described herein.

In another aspect, the present application provides a synthesis method comprising:

(a) providing a compound of Formula III:

(III)

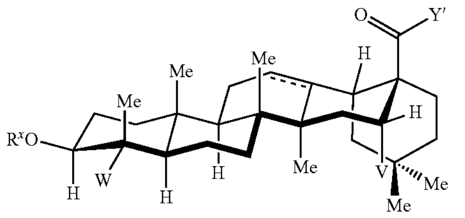

wherein:

$\overset{-}{\text{---}}$ is a single or double bond;

Y' is hydrogen, halogen, alkyl, aryl, OR, $OR^y$, OH, $NR_2$, $NR_3^+$, NHR, $NH_2$, SR, or NROR;

W —CHO;

V —$OR^x$;

$R^x$ is independently hydrogen or an oxygen protecting group selected from the group consisting of alkyl ethers, benzyl ethers, silyl ethers, acetals, ketals, esters, carbamates, and carbonates;

(b) treating said compound of Formula III under suitable conditions with a compound of formula V:

LG-Z (V)

wherein:

Z is a carbohydrate domain having the structure:

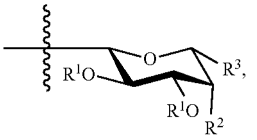

wherein:

$R^1$ is independently H or

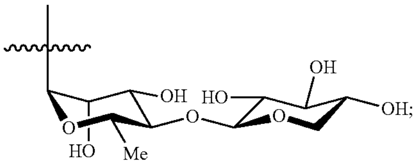

$R^2$ is $NHR^4$;

$R^3$ is $CH_2OH$; and $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

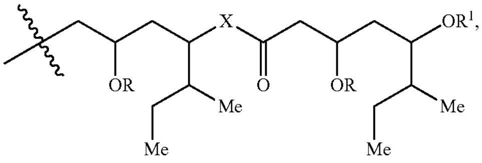

wherein:

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

(c) to give a compound of Formula I as described herein.

In another aspect, the present application provides a method of synthesizing a compound of Formula I, or an intermediate thereof, comprising the following steps:

(a) providing a compound of Formula III:

(III)

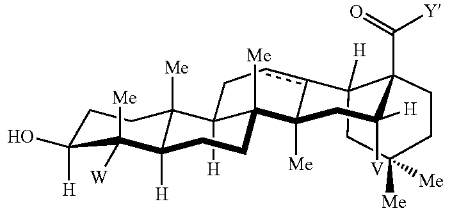

wherein:

⎓ is a single or double bond;

Y' is hydrogen, halogen, alkyl, aryl, OR, $OR^y$, OH, $NR_2$, $NR_3^+$, NHR, $NH_2$, SR, or NROR;

W —CHO;

V —OH;

wherein one or more substituents of the compound of Formula III are optionally protected;

(b) reacting the compound of Formula III with a compound of Formula X:

(X)

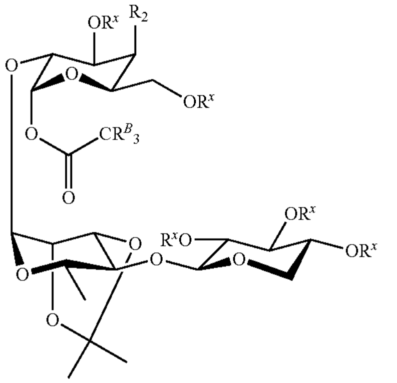

wherein:

RH is a halogen;

$R^2$ is hydrogen, $N_3$, $NH_2$, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

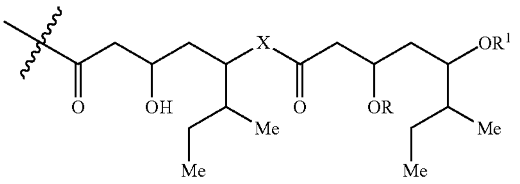

wherein:

X is —O—, —NR—, or T-$R^z$;

T is a covalent bond or a bivalent $C_{1-26}$ saturated or unsaturated, straight or branched, aliphatic or heteroaliphatic chain;

$R^z$ is hydrogen, halogen, —OR, —$OR^x$, —$OR^{1'}$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

$R^x$ is independently hydrogen or an oxygen protecting group selected from the group consisting of alkyl ethers, benzyl ethers, silyl ethers, acetals, ketals, esters, carbamates, and carbonates; and R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur;

$R^{1'}$ is $R^x$ or a carbohydrate domain having the structure:

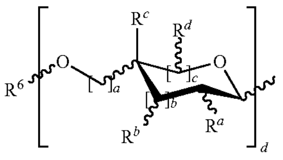

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur.

In one embodiment, the compound of Formula X is:

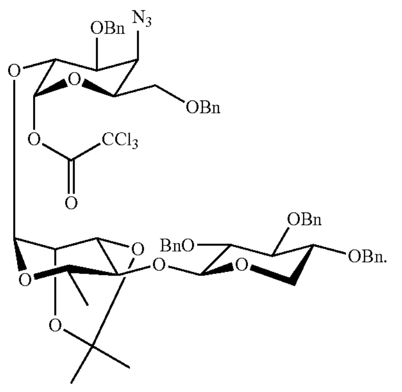

In one embodiment, the method includes reacting the product of step (b) or a further downstream product with $R^4$—OH. In one embodiment, the method includes reacting the product of step (b) or a compound obtained after modifying the product of step (b) with $R^4$—OH. In one embodiment, the method includes reacting the product of step (b) or a compound obtained after modifying the product of step (b) with $R^4$—OH. In one embodiment, the method includes reacting the product of step (b) or an intermediate with $R^4$—OH. In one embodiment, $R^4$—OH is HO—C(O)—$(CH_2)_{10}$—C(O)—$OR^x$. In one embodiment, $R^x$ is H. In one embodiment, $R^x$ is Bn.

In another aspect, the present application provides a method of synthesizing a compound of Formula I, or an intermediate thereof, comprising at least one of the following steps:

(a)

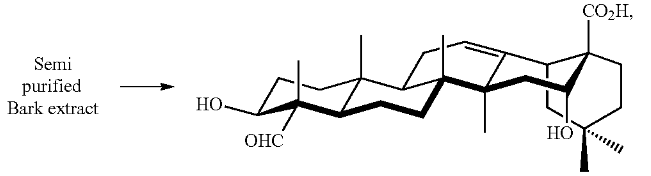

(b)

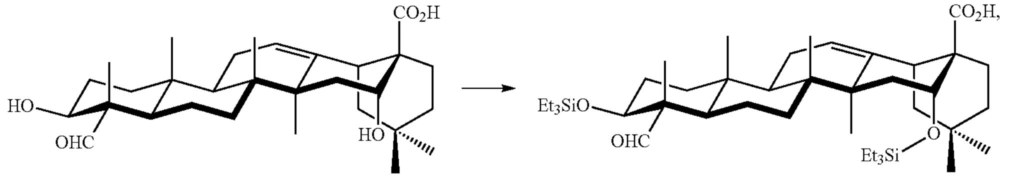

(c)

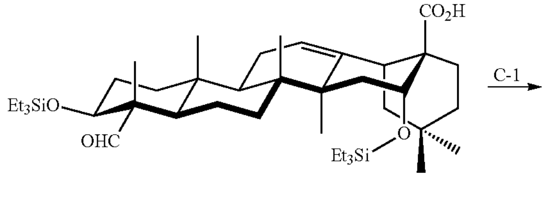

-continued
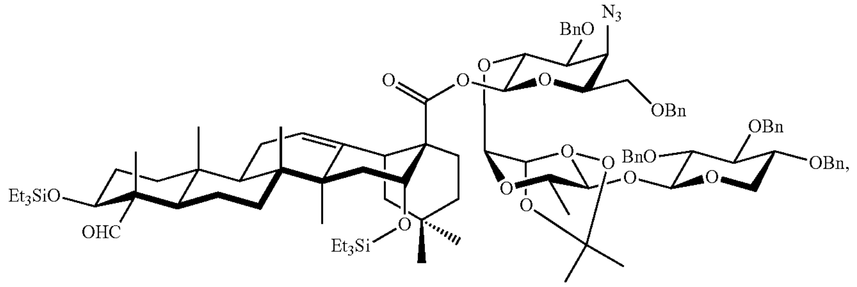
wherein C-1 is:
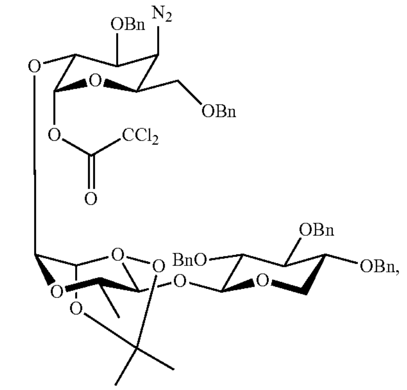
(d)
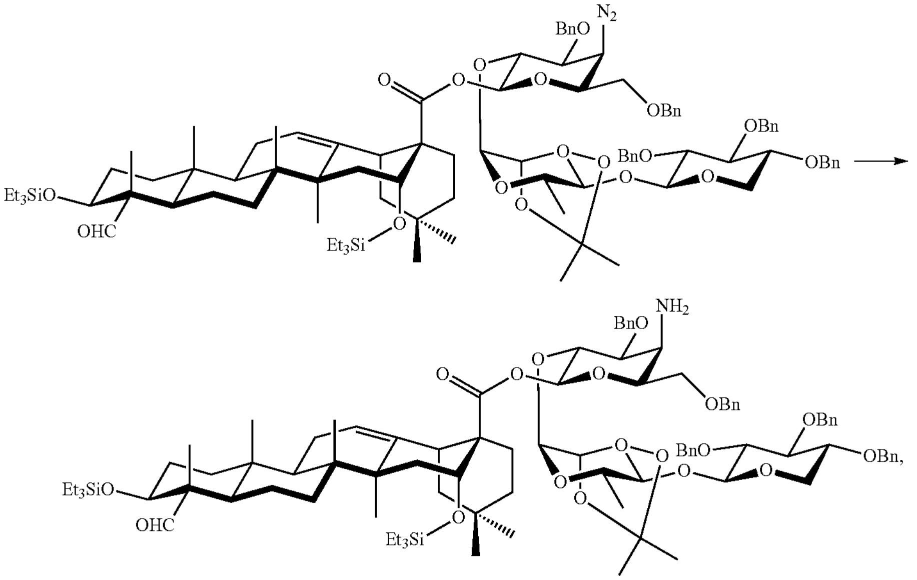
(e)
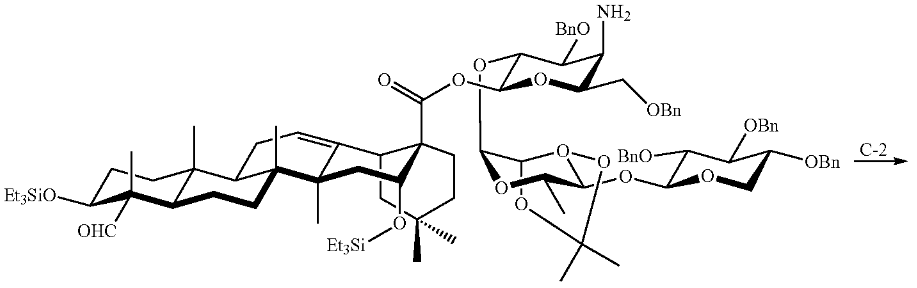

-continued
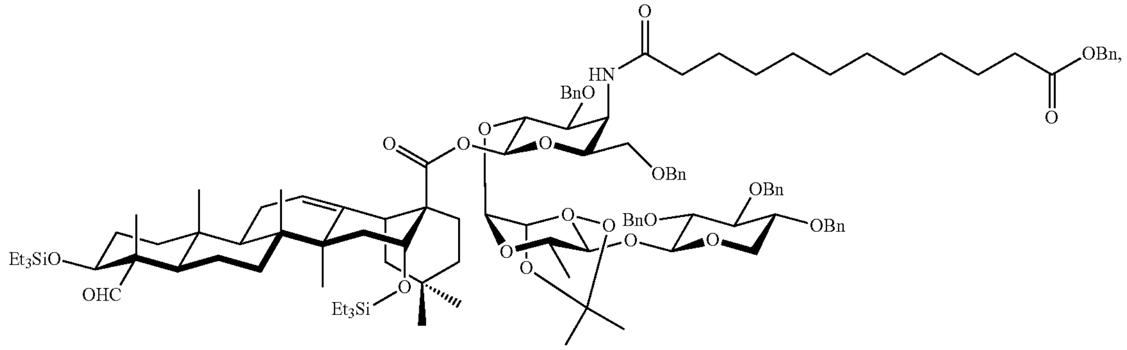
wherein C-2 is $OH—C(O)—(CH_2)_{10}—C(O)—OBn$,
(f)
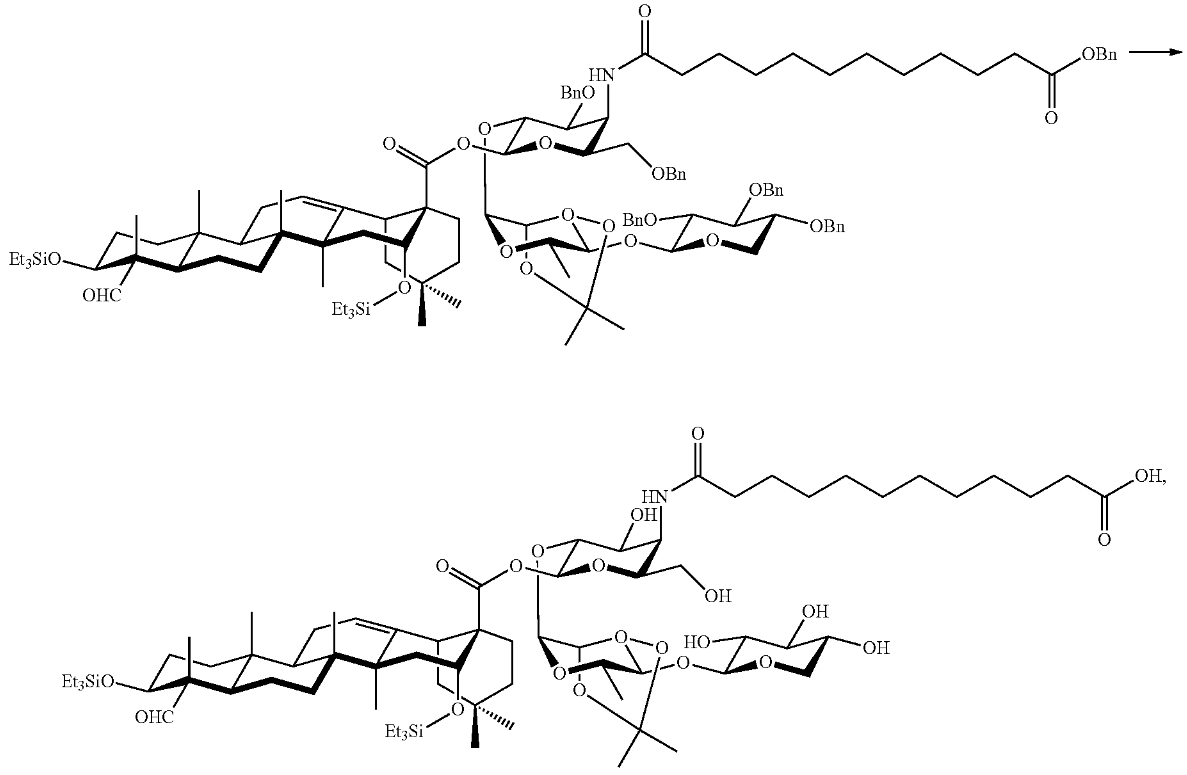
(g)
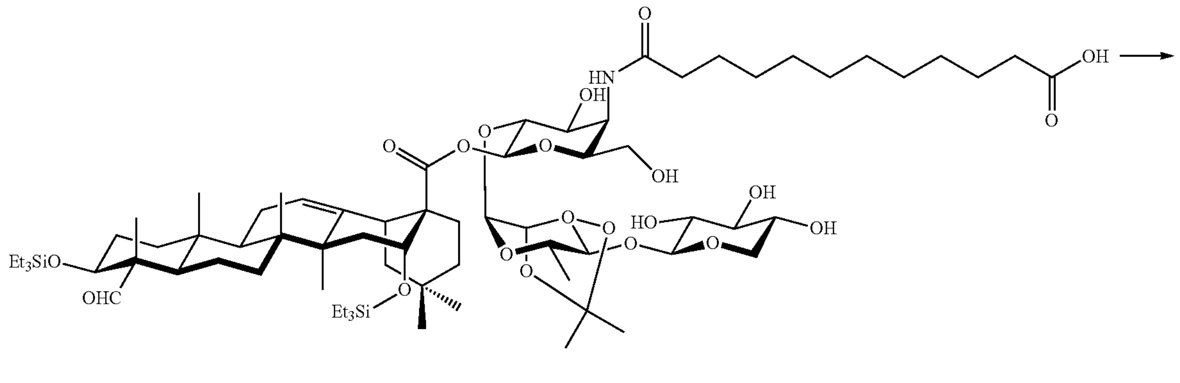

-continued

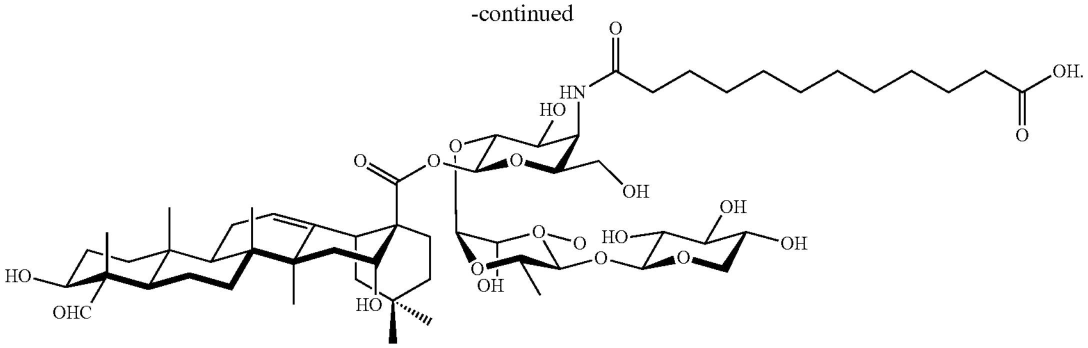

Figure 6:
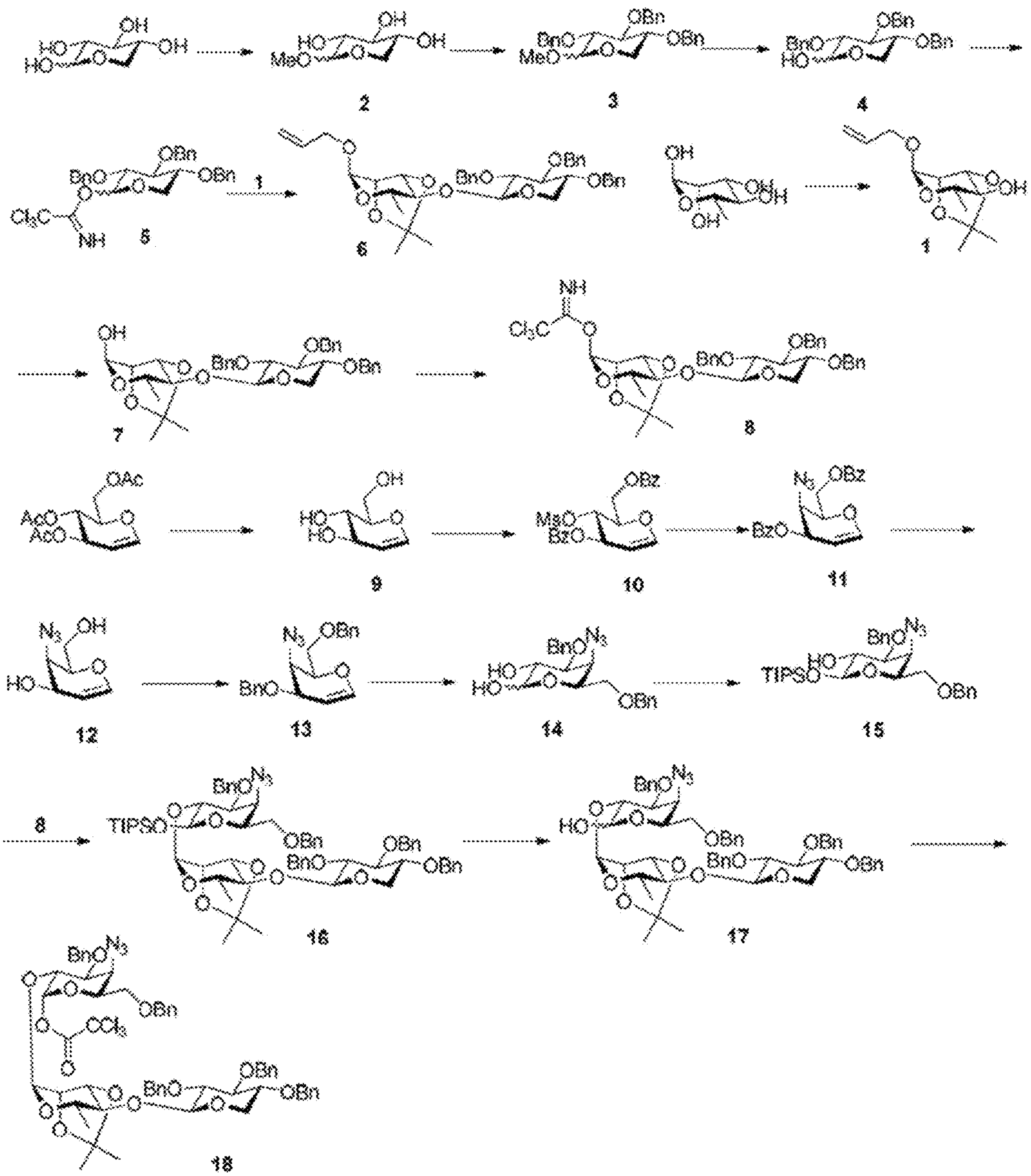
FIG. 6 depicts one synthetic route to obtain an intermediate used in the total synthesis of Compound I-4 (TiterQuil-1-0-5-5/TQL-1055).
Figure 7:
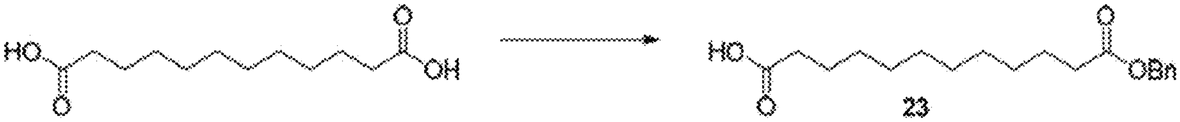
FIG. 7 depicts one synthetic route to obtain an intermediate used in the total synthesis of Compound I-4 (TiterQuil-1-0-5-5/TQL-1055).
Figure 8:
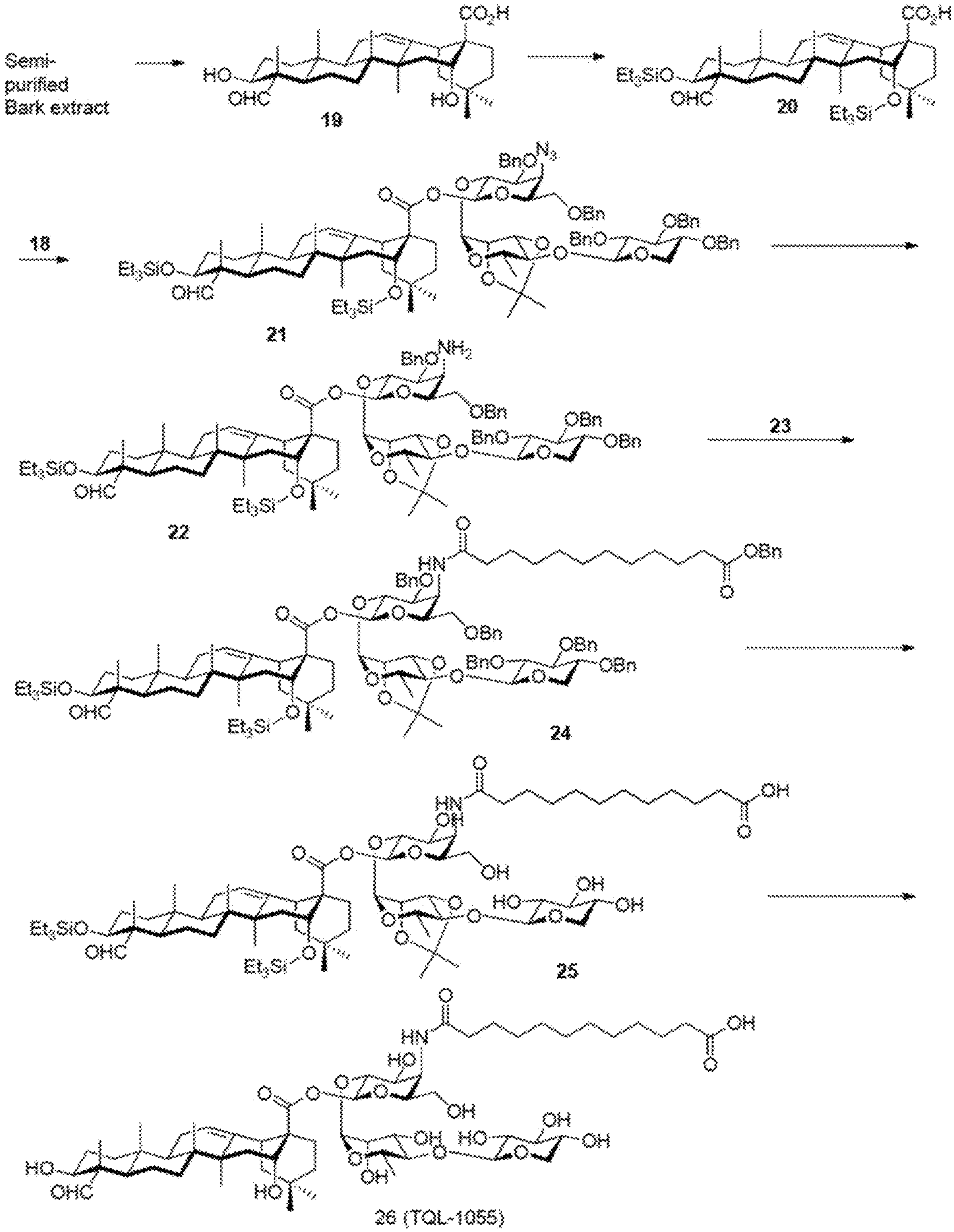
FIG. 8 depicts the total synthesis to obtain Compound I-4 (TiterQuil-1-0-5-5/TQL-1055). In this figure, "Semi-purified Bark extract" is the semi-purified abstract from Quillaja *saponaria* (commercially available as Quil-A, Accurate Chemical and Scientific Corporation, Westbury, NY).

In another aspect, the present application discloses a synthesis route for Compound I-4 (TQL-1055/TiterQuil-1-0-5-5), as shown, for example, in FIG. 6-8. It will be understood by one of ordinary skill in the art that the synthesis of Compound I-4 and its intermediates described in these figures may be modified or adapted according to the knowledge of one of ordinary skill in the art to obtain other molecules. It will be understood by one of ordinary skill in the art that the synthesis of Compound I-4 and its intermediates described in these figures may be modified or adapted according to the knowledge of one of ordinary skill in the art to alter the route to Compound I-4 (TQL-1055/TiterQuil-1-0-5-5).

In another aspect of the subject matter, synthesis of QS-21, QS-7, and/or analogs of these compounds may be undertaken by using one or more of the methods disclosed in the examples, including examples 1-10, described in this application. Although the synthesis of several compounds is disclosed in these examples, one of ordinary skill in the art will appreciate that these methods may be modified or adapted according to the knowledge of one of ordinary skill in the art to obtain other molecules.

In another aspect, the present application also includes methods for obtaining the compounds according the present application comprising providing a compound according to the application and a second substance, and subsequently purifying the compound of the application by removing at least a portion of the second substance.

Adjuvants

Most protein. and glycoprotein antigens are poorly immunogenic or non-immunogenic when administered alone. Strong adaptive immune responses to such antigens often requires the use of adjuvants. Immune adjuvants are substances that, when administered to a subject, increase the immune response to an antigen or enhance certain activities of cells from the immune system. An adjuvant may also allow the use of a lower dose of antigen t achieve a useful immune response in a subject.

Common adjuvants include alum, Freund's adjuvant (an oil-in-water emulsion with dead mycobacteria), Freund's adjuvant with MDP (an oil-in-water emulsion with muramyl dipeptide, MDP, a constituent of mycobacteria), alum plus *Bordetella* pertussis (aluminum hydroxide gel with killed *B. pertussis*. Such adjuvants are thought to act by delaying the release or antigens and enhancing uptake by macrophages. Immune stimulatory complexes (ISCOMs) are open cage-like complexes typically with a diameter of about 40 nm that are built up by cholesterol, lipid, immunogen, and saponin such as Quil-A (a *Quillaja* saponin extract). ISCOMs deliver antigen to the cytosol, and nave been demonstrated to promote antibody response and induction of T helper cell as well as cytotoxic T lymphocyte responses in a variety or experimental animal models.

Natural saponin adjuvant QS-21 is far more potent than currently used adjuvants, like alum. QS-2 s superiority over more than 20 other adjuvants tested in preclinical models and over 7 other adjuvants used in the clinic has been demonstrated. Thus, QS-21 has been widely used despite its three major liabilities: dose limiting toxicity, poor stability, and the limited availability of quality product.

Use of QS-21 as an adjuvant has been associated with notable adverse biological effects. In humans, QS-21 has displayed both local and systemic toxicity. Maximum doses for cancer patients are 100-150 μg and for healthy patients are typically 50 μg (an immunology suboptimal dose). As a result, clinical success of non-cancer vaccines depends upon the identification of novel, potent adjuvants that are more tolerable.

The present application encompasses the recognition that synthetic access to and structural modification of QS-21 and related *Quillaja saponins* may afford compounds with high adjuvant potency and low toxicity, as well as having more stability and being more cost effective.

Vaccines

Compositions in this application are useful as vaccines to induce active immunity towards antigens in subjects. Any animal that may experience the beneficial effects of the compositions of the present application is within the scope of subjects that may be treated. In some embodiments, the subjects are mammals. In some embodiments, the subjects are humans.

The vaccines of the present application may be used to confer resistance to infection by either passive or active immunization. When the vaccines of the present application are used to confer resistance through active immunization, a vaccine of the present application is administered to an animal to elicit a protective immune response which either prevents or attenuates a proliferative or infectious disease. When the vaccines of the present application are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present application thus concerns and provides a means for preventing or attenuating a proliferative disease resulting f rom organisms which have antigens that are recognized and bound by antisera produced in response to the immunogenic antigens included in vaccines of the present application. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine (s) are provided in advance of any symptoms of proliferative disease. The prophylactic administration of the vaccine(s) serves to prevent or attenuate any subsequent presentation of the disease. When provided therapeutically, the vaccine (s) is provided upon or after the detection of symptoms which indicate that an animal may be infected with a pathogen. The therapeutic administration of the vaccine(s) serves to attenuate any actual disease presentation. Thus, the vaccines may be provided either prior to the onset of disease proliferation (so as to prevent or attenuate an anticipated infection) or after the initiation of an actual proliferation.

Thus, in one aspect the resent application provides vaccines comprising an antigen associated with Hepatitis B, pneumococcus, diphtheria, tetanus, pertussis, or Lyme disease including the closely related spirochetes of the genus *Borrelia* such as, *B. burgdorferi, B. garinii, B. afzelii*, and *B. japonica.*

One of ordinary skill in the art will appreciate that vaccines may optionally include a pharmaceutically acceptable excipient or carrier. Thus, according to another aspect, provided vaccines may comprise one or more antigens that are optionally conjugated to a pharmaceutically acceptable excipient or carrier. In some embodiments, said one or more antigens are conjugated covalently to a pharmaceutically acceptable excipient. in other embodiments, said one or more antigens are non-covalently associated with a pharmaceutically acceptable excipient.

As described above, adjuvants may be used to increase the immune response to an antigen. According to the present application, provided vaccines may be used to invoke an immune response when administered to a subject. In certain embodiments, an immune response to an antigen may be potentiated by administering to a subject a provided vaccine in an effective amount to potentiate the immune response of said subject to said antigen.

Formulations

The compounds of the present application may be combined with a pharmaceutically acceptable excipient to form a pharmaceutical composition. In certain embodiments, formulations of the present application include injectable formulations. In certain embodiment, e pharmaceutical composition includes a pharmaceutically acceptable amount of a compound of the present application. In certain embodiments, the compounds of the application and an antigen form an active ingredient. In certain embodiments, the compound of the present application alone forms an active ingredient. The amount of active ingredient(s) which can be combined with a carrier material to produce a single dosage form will vary depending upon the host being treated, and the particular mode of administration. The amount of active ingredient (s) that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%, or from about 1% to 99%, preferably from 10% to 90%, 20% to 80%, 30% to 70%, 40% to 60%, 45% to 55%, tor about 50%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Non-limiting examples of pharmaceutically-acceptable antioxidants include: water soluble antioxidants, such as ascorbic acid, cysteine hydrochoride, sodium bisulfate, sodium metabisulfite, sodium sulfite and the like; oil-soluble antioxidants, such as ascorbyl palmitate, butylated hydroxyanisole (BA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Non-limiting examples of suitable aqueous and nonaqueous carriers, which may be employed in the pharmaceutical compositions of the present application include water, alcohols (including but not limited to methanol, ethanol, butanol, etc.), polyols (including but not limited to glycerol, propylene glycol, polyethylene glycol, etc.), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain additives such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. it may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a formulation, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form.

Regardless of the route of administration selected, the compounds of the present application, which may be used in a suitable hydrated form, and/or the pharmaceutical compositions of the present application, are formulated into pharmaceutically-acceptable dosage forms by conventional methods known to those of skill in the art.

Actual dosage levels of the active ingredients in the pharmaceutical compositions of the present application may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present application employed, or the ester, salt or amide thereof, the route of administration, the time of administration, the rate of excretion or metabolism of the particular compound being employed, the duration of the treatment, other drugs, compounds and/or material s used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the present application employed in the pharmaceutical composition at levels lower than that required to achieve the desired therapeutic effect and then gradually increasing the dosage until the desired effect is achieved.

In some embodiments, a compound or pharmaceutical composition of the present application is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the present application repeatedly over the life of the subject. Preferred chronic treatments involve regular administrations, for example one or more times a day, one or more times a week, or one or more times a month. In general, a suitable dose, such as a daily dose of a compound of the present application, will be that amount of the compound that is the lowest dose effective to produce a therapeutic effect. Such an effective dose will generally depend upon the factors described above.

Generally, doses of the compounds of the present application for a patient, when used for the indicated effects, will range from about 0.0001 to about 100 mg per kc of body weight per day. Preferably the daily dosage will range from 0.001 to 50 mc of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds of the present application are administered as pharmaceutical compositions or vaccines. In certain embodiments, it is contemplated that the amount of adjuvant compound administered will be 1-2000 µg. In certain embodiments, it is contemplated that the amount of adjuvant compound administered will be 1-1000 µg. In certain embodiments, it is contemplated that the amount of adjuvant compound administered will be 1-500 µg. In certain embodiments, it is contemplated that the amount of adjuvant compound administered will be 1-250 µg. in certain embodiments, it is contemplated that the amount of adjuvant compound administered will be 100-1000 µg. In certain embodiments, it is contemplated that the amount of adjuvant Compound administered will be 100-500 µg. In certain embodiments, it is contemplated that the amount of adjuvant compound administered will be 100-200 µg. In certain embodiments, it is contemplated that the amount of adjuvant Compound administered will be 250-500 µg. in certain embodiments, it is contemplated that the amount of adjuvant impound administered will be 10-1000 µg. in certain embodiments, it is contemplated that the amount of adjuvant compound administered will be 500-1000 µg. In certain embodiments, it is contemplated that the amount of adjuvant compound administered will be 50-250 µg. In certain embodiments, it is contemplated that the amount of adjuvant compound administered will be 50-500 µg.

In some embodiments, provided adjuvant compounds of the present application are administered as pharmaceutical compositions or vaccines. In certain embodiments, it is contemplated that the amount of adjuvant compound administered will be 1-2000 mg. In certain embodiments, it is contemplated that the amount of adjuvant compound administered will be 1-1000 mg. In certain embodiments, it is contemplated that the amount of adjuvant compound administered will be 1-500 mg. In certain embodiments, it is contemplated that the amount of adjuvant compound administered will be 1-250 mg. in certain embodiments, it is contemplated that the amount of adjuvant compound administered will be 100-1000 mg. In certain embodiments, it is contemplated that the amount of adjuvant compound administered will be 100-500 mg. In certain embodiments, it is contemplated that the amount of adjuvant compound administered will be 100-200 mc. In certain embodiments, it is contemplated that the amount of adjuvant compound administered will be 250-500 mc. In certain embodiments, it is contemplated that the amount of adjuvant compound administered will be 10-1000 mc. in certain embodiments, it is contemplated that the amount of adjuvant compound administered will be 500-1000 mg. in certain embodiments, it is contemplated that the amount of adjuvant compound administered will be 50-250 m. In certain embodiments, it is contemplated that the amount of adjuvant compound administered will be 50-500 mg. in certain embodiments, it is contemplated that the amount of adjuvant compound administered will be 0.01-215.4 mg.

In certain embodiments, it is contemplated that the amount of adjuvant administered will be 1000-5000 µg/kg. In certain embodiments, it is contemplated that the amount of adjuvant administered will be 1000-4000 µg/kg. In certain embodiments, it is contemplated that the amount of adjuvant administered will be 1000-3000 µg/kg. In certain embodiments, it is contemplated that the amount of adjuvant administered will be 1000-2000 µg/kg. In certain embodiments, it is contemplated that the amount of adjuvant administered will be 2000-5000 µg/kg. In certain embodiments, it is contemplated that the amount of adjuvant administered will be 2000-4000 µg/kg. In certain embodiments, it is contemplated that the amount of adjuvant administered will be 2000-3000 µg/kg. In certain embodiments, it is contemplated that the amount of adjuvant administered will be 3000-5000 µg/kg. In certain embodiments, it is contemplated that the amount of adjuvant administered will be 3000-4000 µg/kg. In certain embodiments, it is contemplated that the amount of adjuvant administered will be 4000-5000 µg/kg. In certain embodiments, it is contemplated that the amount of adjuvant administered will be 1-500 µg/kg. In certain embodiments, it is contemplated that the amount of adjuvant administered will be 500-1000 µg/kg. In certain embodiments, it is contemplated that the amount of adjuvant administered will be 1000-1500 µg/kg. In certain embodiments, it is contemplated that the amount of adjuvant administered will be 1 mg/kg. In certain embodiments, it is contemplated that the amount of adjuvant administered will be 2 mg/kg. In certain embodiments, it is contemplated that the amount of adjuvant administered will be 3 mg/kg. In certain embodiments, it is contemplated that the amount of adjuvant administered will be 4 mg/kg. In certain embodiments, it is contemplated that the amount of adjuvant administered will be 5 mg/kg. In certain embodiments, it is contemplated that the amount of adjuvant administered will be 0.0029-5 mg/kg. In certain embodiments, the amount of adjuvant administered in females is less than the amount of adjuvant administered in males. In certain embodiments, the amount of adjuvant administered to infants is less than the amount of adjuvant administered to adults. In certain embodiments, the amount of adjuvant administered to pediatric recipients is less than the amount of adjuvant administered to adults. In certain embodiments, the amount of adjuvant administered to immunocompromised recipients is more than the amount of adjuvant administered to healthy recipients. In certain embodiments, the amount of adjuvant administered to elderly recipients is more than the amount of adjuvant administered to non-elderly recipients.

If desired, the effective dose of the active compound may be administered as two, three, four, five, six or more sub-doses administered separately at appropriate intervals throughout the day, optionally, in unit dosage forms.

While it is possible for a compound of the present application to be administered alone, in certain embodiment the compound is administered as a pharmaceutical formulation or composition as described above.

The compounds according to the present application may be formulated for administration in any convenient way for use in human or veterinary medicine, by analogy with other pharmaceuticals.

The present application provides kits comprising pharmaceutical formulations or compositions of a compound of the present application. In certain embodiments, such kits include the combination of a compound of formulae I and/or II and an antigen. The agents may be packaged separately or together. The kit optionality includes instructions for prescribing the medication. In certain embodiments, the kit includes multiple doses of each agent. The kit may include sufficient quantities of each component to treat one or more subject for a week, two weeks, three weeks, four weeks, or multiple months. The kit mar include a full cycle of immunotherapy. In some embodiments, the kit includes a vaccine comprising one or more bacterial or viral-associated antigens, and one or more provided compounds.

EXAMPLES

The numbering associated with compounds in the Examples 1-9 is not meant to correspond with other formula or compound numbering appearing throughout the remainder of the application, including the Figures, the claims, or Example 10.

Example 1: Isolation and Selective Protection of Quillaic Acid Triterpene

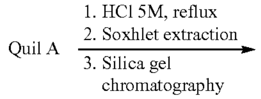

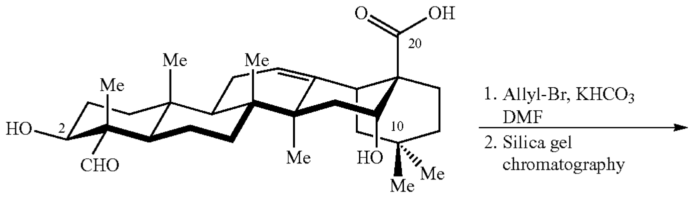

9
Quillaic Acid Triterpene

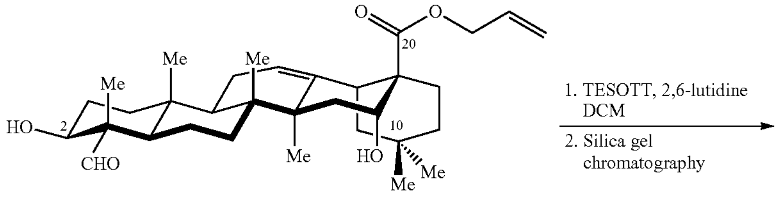

10
Quillaic Allyl Ester

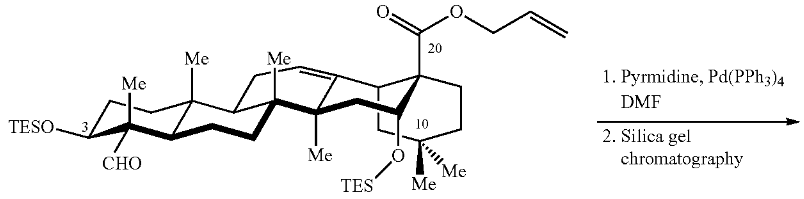

11
Protected
Quillaic Acid Triterpene

-continued

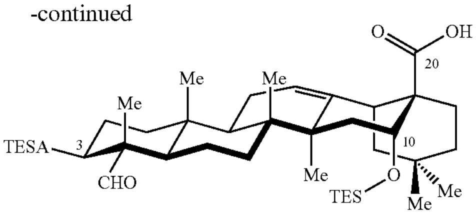

12
TES-protected
Quillaic Acid Triterpene

Part A: Isolation of Quillaic Acid Triterpene 9 from Quil-A.

1. In a 250-mL round-bottomed flask equipped with a reflux condenser, Quil A (5 g) is suspended in distilled water (25 mL)

and concentrated HCl (17 mL) is added.

2. The mixture is slowly heated to reflux for 7 h (Heating should be done slowly to avoid a foam-over when approaching reflux), then removed from heat, and filtered through filter paper. The dark brown solid is washed with hot (~65° C.) distilled water (2×50 mL), collected and dried under high vacuum overnight.

3. The dry solid is placed into a Soxhlet thimble and subjected to continuous extraction with diethyl ether (200 mL) for 24 h.

4. The ether solution is concentrated, the residue is dissolved in MeOH (20 mL), and activated charcoal (~5 g) is added. The mixture is filtered through celite, the solids are washed with MeOH (50 mL), and the solvent is removed by rotary evaporation.

5. The resulting residue is purified by silica gel chromatography (CHCl 3/MeOH, 30:1 to 20:1 to 10:1) to afford the quillaic acid triterpene 9 (~0.5 g, ~10% mass yield) (Quillaic acid triterpene product is ~80% pure. High purity is achieved after allylation reaction.).

Part B: Synthesis of Quillaic Acid Allyl Ester 10 by Allylation of C28 Carboxylic Acid of Quillaic Acid.

1. In a 50-mL round-bottomed flask, the quillaic acid triterpene 9 (100 mg, 0.20 mmol, 1.0 equiv.) is dissolved in DMF (5 mL) and the solution is cooled to 0° C.

2. Potassium bicarbonate (205 mg, 2.05 mmol, 10 equiv.) and allyl bromide (23 μL, 0.27 mmol, 1.3 equiv.) are added and the mixture is stirred and allowed to warm to room temperature (rt) overnight.

3. The reaction is diluted with water (25 mL) and extracted with hexanes/EtOAc (1:1) (3×15 mL). The organic extracts are combined, washed with brine (15 mL), dried over anhydrous $Na_2SO_4$, filtered, and concentrated.

4. Purification by silica gel chromatography (hexanes/EtOAc, 8:1 to 2:1) affords quillaic acid allyl ester 10 (77 mg, 71%) as a white solid.

Part C: Synthesis of Protected Quillaic Acid Triterpene 11 by Silylation of C3 and C16 Hydroxyl Groups of Quillaic Acid Alkyl Ester 10

1. In a 25-mL modified Schlenk flask, quillaic allyl ester 10 (77 mg, 0.15 mmol, 1.0 equiv.) is dissolved in DCM (5 mL) and the solution is cooled to 0° C. 2,6-Lutidine (0.17 mL, 1.46 mmol, 10 equiv.) is added, followed by TESOTf (0.17 mL, 0.73 mmol, 5.0 equiv.) via gas-tight syringe, and the mixture is stirred while the ice bath is allowed to melt.

2. The reaction progress is monitored by TLC using $CHCl_3$/MeOH (10:1) as eluent. If the reaction is not complete after 3 h, more TESOTf (33 μL, 0.15 mmol, 1.0 equiv.) is added and the mixture is stirred until the reaction is complete.

3. The reaction mixture is diluted with water (10 mL) and the aqueous phase is extracted with EtOAc (10 mL×3). The combined organic phases are dried (anhydrous $Na_2SO_4$), filtered, and concentrated.

4. Purification by silica gel chromatography (hexanes/acetone, 1:0 to 10:1) yields the TES-protected quillaic allyl ester 11 (93 mg, 84%) as a white solid.

Part D: Synthesis of TES-Protected Quillaic Acid Triterpene 12 by Deallylation of Protected Quillaic Acid 1. In a 10-mL round-bottomed flask, fully protected quillaic acid 11 (93 mg, 0.12 mmol, 1.0 equiv.) is dissolved in DCM (2 mL) and pyrrolidine (51 μL, 0.61 mmol, 5.0 equiv.) is added, followed by Pd(PPh3)4 (7.0 mg, 0.006 mmol, 0.05 equiv.).

2. The reaction mixture is stirred for 15 min, then directly subjected to purification by silica gel chromatography (hexanes/EtOAc, 2:1), to afford TES-protected quillaic acid 12 (88 mg, >99%) as a white solid.

Example 2: Synthesis of Truncated Linear Oligosaccharide Domain

Part A: Synthesis of Selectively Protected Monosaccharide Precursor 2,3,4-Tri-O-Benzyl-D-Xylose 15 from D-Xylose

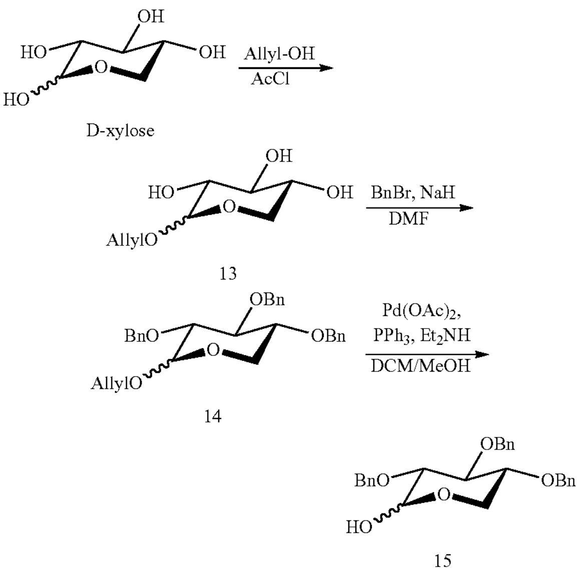

D-xylose

13

14

15

1. Step A: Synthesis of 1-O-allyl-D-xylose 13 by selective allylation of D-xylose. In a 500-mL round-bottomed flask, a solution of allyl alcohol (50 mL, 0.74 mol, 9.0 equiv.) and AcCl (12.7 mL, 0.17 mol, 2.1 equiv.) is cooled to −10° C., then solid D-xylose (12.3 g, 0.08 mol, 1.0 equiv.) is added.

2. Once all xylose has been added, the cooling bath is removed and the reaction mixture is stirred for 19 h at rt.

3. Solid $NaHCO_3$ (25 g) is added, the mixture is filtered through a pad of celite, and the volatile materials are removed by rotary evaporation.

4. The residue is passed through a plug of silica gel eluted with DCM/MeOH (9:1) and the eluate is concentrated to afford the anomeric allyl xylose 13 (11.5 g), which is used in the next step without further purification.

5. Step B: Synthesis of 1-O-allyl-2,3,4-tri-O-benzyl-D-xylose 14 by benzylation of 1-O-allyl-D-xylose 13. In a 500-mL round-bottomed flask, allyl xylose 13 (11.5 g, 60.5 mmol, 1.0 equiv.) is dissolved in DMF (200 mL), then the solution is cooled to 0° C. Sodium hydride (60% dispersion in oil, 15.7 g, 0.39 mol, 6.5 equiv.) (Caution: sodium hydride reacts violently with water) is added and the reaction mixture is stirred for 10 min.

6. Benzyl bromide (47 mL, 0.39 mol, 6.5 equiv.) is added dropwise at 0° C., and the resulting suspension is stirred at rt for 16 h.

7. The reaction mixture is cooled to 0° C. and quenched by slow addition of MeOH (150 mL) followed by water (600 mL). The mixture is extracted with hexanes/EtOAc (1:1) (3×250 mL) and the combined organic layers are washed with water (100 mL), brine (100 mL), dried with anhydrous $MgSO_4$, filtered, and concentrated.

8. Purification by silica gel chromatography (hexanes/EtOAc, 9:1) affords the fully protected xylose 14 (23 g, 83%).

9. Step C: Synthesis of selectively protected 2,3,4-tri-O-benzyl-D-xylose 15 by deallylation of 1-O-allyl-2,3,4-tri-O-benzyl-D-xylose 14. In a 100-mL round-bottomed flask covered in aluminum foil, $PPh_3$ (3.4 g, 13 mmol, 1.2 equiv.) and Pd(OAc) 2 (0.45 g, 2.2 mmol, 0.2 equiv.) are dissolved in DCM/MeOH (1:1) (20 mL), then $Et_2NH$ (15.8 mL, 0.15 mol, 14.0 equiv.) is added.

10. A solution of the fully protected xylose 14 (5.0 g, 10.9 mmol, 1.0 equiv.) in DCM (100 mL) is added by cannula transfer, and the reaction mixture is stirred at 30° C. for 18 h.

11. The solution is passed through a plug of silica gel eluted with hexanes/EtOAc (1:1) and the eluate is concentrated.

12. Purification by silica gel chromatography (hexanes/EtOAc, 8:2 to 7:3) affords 2,3,4,-tri-O-benzyl xylose 15 (4.1 g, 90%) as a mixture of anomers (α:β, 2:1).

Part B: Synthesis of Selectively Protected Monosaccharide Precursor 1-O-Allyl-2,3-O-isopropylidene-L-rhamnose 16 from L-Rhamnose

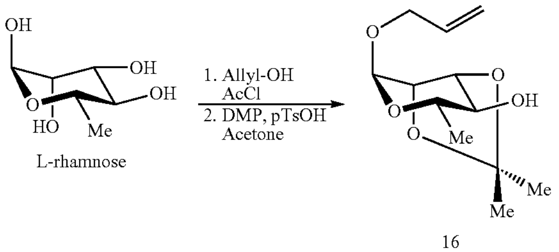

L-rhamnose

16

1. In a 250-mL round-bottomed flask, a solution of allyl alcohol (34 mL, 0.50 mol, 9.0 equiv.) and AcCl (8.1 mL, 0.12 mol, 2.1 equiv.) is cooled at −10° C., then L-rhamnose monohydrate (10 g, 0.055 mol, 1.0 equiv.) is added.

2. The mixture is stirred for 20 h at rt, neutralized with $Et_3N$, and concentrated.

3. The residue is dissolved in toluene and the solution is concentrated to remove allyl alcohol; this process is repeated two more times.

4. The residual syrup is dissolved in dry acetone (75 mL), and DMP (27 mL, 0.22 mol, 4.0 equiv.) and pTsOH monohydrate (95 mg, 0.5 mmol, 0.01 equiv.) are added.

5. The reaction mixture is stirred for 16 h at rt and Et 3 N is then added.

6. The reaction mixture is concentrated and purified by silica gel chromatography (hexanes/EtOAc, 8:2) to afford 1-O-allyl-2,3-O-isopropylidene-α-L-rhamnose (16) (8.9 g, 66%) as a colorless oil.

Part C: Synthesis of Selectively Protected Monosaccharide Precursor 4-Azido-4-Deoxy-3,6-Di-O-Benzyl-1-Otriisopropylsilyl-D-Galactose 21 from D-Glucal

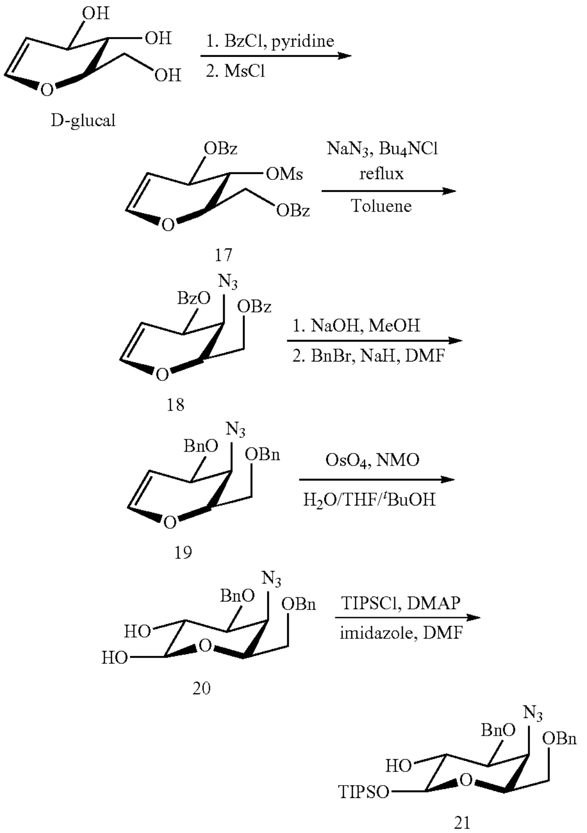

D-glucal

17

18

19

20

21

1. Step A: Synthesis of 3,6-di-O-benzoyl-4-O-mesyl-D-glucal 17 by selective protection of D-glucal. In a 500-mL round-bottomed flask, D-glucal (10.0 g, 67.1 mmol, 1.0 equiv.) is dissolved in pyridine (165 mL) and the solution is cooled to 0° C., then BzCl (17 mL, 0.15 mol, 2.2 equiv.) is added dropwise.

2. The reaction mixture is stirred at 0° C. for 1.5 h, then MsCl (10.3 mL, 0.13 mol, 2.0 equiv.) is added. The reaction mixture is stirred for 0.5 h while allowing the ice bath warm to rt, then quenched by slow addition of MeOH (20 mL) at 0° C. (Caution: exothermic reaction).

3. The mixture is concentrated and the residue is partitioned between EtOAc (200 mL) and water (200 mL). The organic layer is washed with water (100 mL), brine (100 mL), dried with anhydrous $MgSO_4$, filtered, and concentrated.

4. Purification by silica gel chromatography (hexanes/EtOAc, 8:2) affords 3,6-di-O-benzoyl-4-O-mesyl-D-glucal (17) (19.4 g, 67%) as a syrup.

5. Step B: Synthesis of 4-azido-4-deoxy-3,6-di-O-benzoyl-D-galactal 18 by azide substitution of mesylate 17. In a 250 mL round bottomed flask, the mesyl-glucal 17 (5.1 g, 11.8 mmol, 1.0 equiv.) is dissolved in toluene (55 mL), then sodium azide (Caution: sodium azide is a toxic, hazardous substance that should not be acidified to avoid poisonous, explosive hydrazoic acid ($HN_3$). The reaction should be carried out behind a blast shield due to risk of explosion of sodium azide when heated near its decomposition temperature (300° C.)) (2.8 g, 43.3 mmol, 3.7 equiv.) is added, followed by $Bu_4NCl$ (7.1 g, 25.6 mmol, 2.2 equiv.), and the flask is equipped with a reflux condenser.

6. The reaction mixture is heated to reflux (110° C.) for 20 h. The resulting brown suspension is washed with water (2×100 mL), dried with anhydrous $MgSO_4$, filtered, and concentrated to give an orange oil.

7. Purification by silica gel chromatography (hexanes/EtOAc, 19:1 to 8:2) provides 4-azido-4-deoxy-3,6-di-0-benzoyl-D-galactal (18) (2.9 g, 66%) as a light yellow oil.

8. Step C: Synthesis of 4-azido-4-deoxy-3,6-di-O-benzyl-D-galactal 19 by saponification and benzylation of dibenzoate 18. In 250-mL round-bottomed flask, the benzoyl-protected azidogalactal 18 (2.9 g, 8.1 mmol, 1.0 equiv.) is dissolved in MeOH (40 mL) and the solution is cooled to 0° C.

9. Sodium hydroxide (0.12 g, 2.9 mmol, 0.36 equiv.) is added and the reaction mixture is stirred for 14 h at rt.

10. The reaction mixture is concentrated to afford a sticky tan solid, then evaporated again from toluene (7 mL) to remove trace solvent.

11. DMF (40 mL) is added to the residue and the resulting brown suspension is cooled to 0° C. Sodium hydride (60% dispersion in mineral oil, 0.98 g, 24.4 mmol, 3.0 equiv.) (Caution: sodium hydride reacts violently with water) is added, followed by benzyl bromide (4.8 mL, 40.3 mmol, 5.0 equiv.), and the mixture is stirred at 0° C. for 3 h.

12. The resulting orange suspension is stirred for another 16 h at rt, and the reaction is quenched with MeOH (20 mL), diluted with DCM (100 mL), and washed with water (100 mL).

13. The aqueous layer is extracted with DCM (80 mL), and the combined organic layers are washed with water (100 mL), dried with anhydrous $MgSO_4$, filtered, and concentrated.

14. Purification by silica gel chromatography (hexanes/EtOAc, 9:1 to 4:1) affords 4-azido-4-deoxy-3,6-di-O-benzyl-D-galactal (19) (2.2 g, 78%) as a yellow oil.

15. Step D: Synthesis of 4-azido-4-deoxy-3,6-di-O-benzyl-D-galactose 20 by dihydroxylation of galactal 19. The benzyl-protected azidogalactal 19 (5.8 g, 16.5 mmol, 1.0 equiv.) is dissolved in a mixture of water/THF/tBuOH (1:3:7) (400 mL), then $OSO_4$ (2.5 wt % in tBuOH) (5.1 mL, 0.4 mmol, 0.025 equiv.) is added. NMO (50% in water) (10.2 mL, 44.5 mmol, 3.0 equiv.) is added in three portions (1.0 equiv. each) over 8 h.

16. The reaction mixture is stirred at rt overnight, then quenched with saturated aqueous $Na_2SO_3$ solution (30 mL) and EtOAc (200 mL).

17. After 5 min, the phases are separated and the aqueous layer is extracted with EtOAc (2×75 mL) and DCM (2×50 mL). The combined organic phases are dried over anhydrous sodium sulfate, filtered, and concentrated.

18. Purification by silica gel chromatography (hexanes/EtOAc,

4:1 to 1:1) affords 4-azido-4-deoxy-3,6-di-O-benzyl-D-galactose (20) (5.5 g, 88%) as a colorless oil.

19. Step E: Synthesis of 4-azido-4-deoxy-3,6-di-O-benzyl-1-O-triisopropylsilyl-D-galactose 21 by selective silylation of diol 20. In a 10-mL modified Schlenk flask, the galactose diol 20 (0.96 g, 2.5 mmol, 1.0 equiv.) is dissolved in DMF (2.5 mL), then imidazole (0.41 g, 6.0 mmol, 2.4 equiv.) and DMAP (29 mg, 0.24 mmol, 0.1 equiv.) are added.

20. TIPSCl (0.63 mL, 3.0 mmol, 1.2 equiv.) is added and the reaction mixture is stirred for 19 h at rt.

21. The yellow solution is concentrated and purified by silica gel chromatography (hexanes/EtOAc, 19:1 to 9:1) to afford 4-azido-4-deoxy-3,6-di-O-benzyl-1-O-triisopropylsilyl-D-galactose (21) (0.8 g, 59%) as a colorless oil.

Part D: Synthesis of Protected Xylose-Rhamnose Disaccharide Hemiacetal 23 ([2,3,4-Tri-O-Benzyl-β-D-Xylopyranosyl-(1→4)]2,3-Di-O-Isopropylidene-L-Rhamnopyranose) from Protected D-Xylose 15 and Protected L-Rhamnose 16

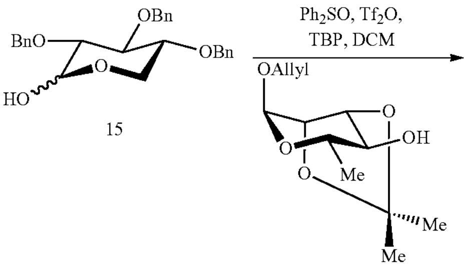

15

16

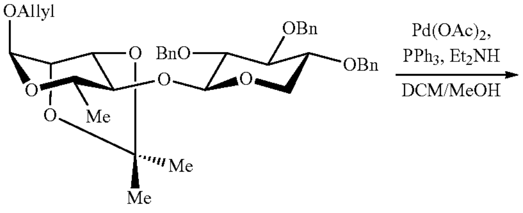

22

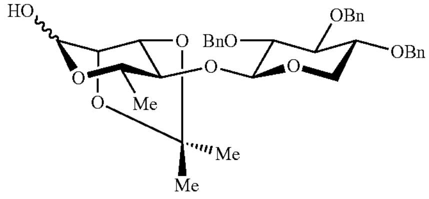

23

1. Step A: Dehydrative glycosylation of protected rhamnose 16 with protected xylose 15 (22): In a 25-mL modified Schlenk flask, azeotropically dried 2,3,4-tri-O-benzyl xylose (15)

(52 mg, 0.12 mmol, 1.7 equiv.), $Ph_2SO$ (69 mg, 0.34 mmol, 4.9 equiv.), and TBP (85 mg, 0.34 mmol, 4.9 equiv.) are dissolved in DCM (2 mL), injected via glass syringe.

2. The solution is cooled to −78° C., $Tf_2O$ (29 μL, 0.17 mmol, 2.4 equiv.) is added via gas-tight syringe, and the reaction mixture is stirred for 2 h at −78° C.

3. A precooled solution of protected rhamnose 16 (17 mg, 70 μmol, 1.0 equiv.) in toluene (1 mL) is then cannula transferred from a flame dried, 10-mL modified Schlenk flask, then additional toluene (1 mL) is added to rinse the source flask and transferred to the reaction flask.

4. The reaction mixture is stirred at −60° C. for 12 h, at −42° C. for 30 min, and finally at 0° C. for 2 min.

5. The reaction is quenched by addition of Et 3 N (0.1 mL) at −42° C., diluted with DCM (90 mL) and transferred to a separatory funnel. The organic layer is washed with saturated aqueous $NaHCO_3$ solution (30 mL) and the aqueous layer is extracted with DCM (2×80 mL). The organic phases are combined, dried over anhydrous $Na_2SO_4$, filtered, and concentrated to afford the crude product as a tan oil (160 mg).

6. Purification by silica gel chromatography (hexanes/EtOAc, 50:1 to 25:1) affords 0-allyl [2,3,4-tri-O-benzyl-β-D-xylopyranosyl-(1→4)]-2,3-O-isopropylidene-L-rhamnopyranoside (22) as a clear oil (32.1 mg, 71% yield).

7. Step B: Anomeric deallylation of protected xylose-rhamnose disaccharide (23): In a 5-mL pear-shaped Schlenk flask equipped with a triangular stir bar, $PPh_3$ (13 mg, 51 μmol, 1.2 equiv.) and $Pd(OAc)_2$ (2.4 mg, 11 μmol, 0.25 equiv.) are placed. A solution of DCM/MeOH (1:1) (0.2 mL) is added via syringe followed by $Et_2NH$ (62 μL, 0.6 mmol, 14.0 equiv.), which results in a change from a clear yellow-orange to a bright yellow solution.

8. Allyl-protected disaccharide 22 (29 mg, 43 μmol, 1.0 equiv.) dissolved in DCM (0.4 mL) is cannula transferred to the reaction Schlenk flask and the source flask is rinsed with additional DCM (0.2 mL) that is transferred to the reaction flask.

9. The solution is degassed by performing three freeze-thaw pump cycles (This degassing technique involves freezing the solvent under liquid nitrogen, evacuating the head-space for 4-5 min, and letting the solvent thaw under static vacuum, thereby allowing any gas bubbles trapped in the solvent to escape into the headspace of the flask. After the last cycle, the flask is refilled with Ar.) and then stirred at 30° C. for 18 h, at which point the turbid solution turns clear, dark yellow.

10. The reaction mixture is passed through a plug of silica gel eluted with hexanes/EtOAc (2:1, 50 mL) and the eluate is concentrated to afford the crude product as a bright yellow oil (29 mg).

11. Purification by silica gel chromatography (hexanes/EtOAc, 2:1) affords disaccharide hemiacetal (23) as an inseparable mixture of anomers (α:β, 9:1) as a clear oil (25.9 mg, >99%).

Step E: Synthesis of Protected Xylose-Rhamnose-Azidogalactose Trisaccharide Imidate 26 (O-Trichloroacetimidoyl {[2,3,4-tri-O-Benzyl-/3-D-xylopyranosyl-(1→4)]-2,3-Oisopropylidene-L-rhamnopyranosyl-(1→2)}-4-azido-4-deoxy-3,6-O-benzyl-β-D-galactopyranoside)

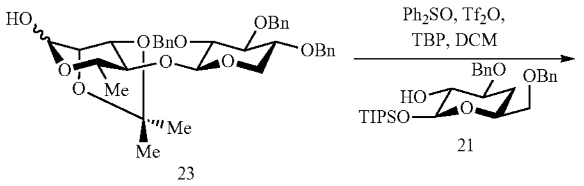

23

21

-continued

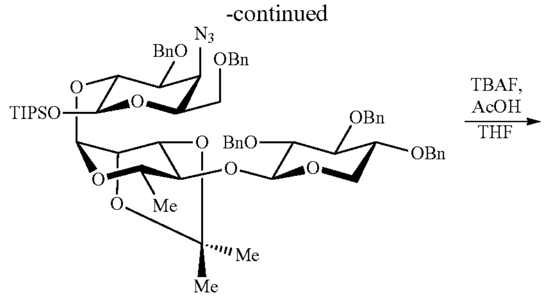

24

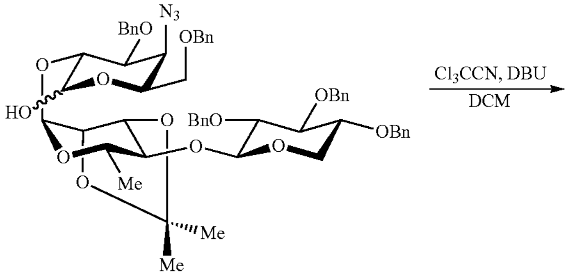

25

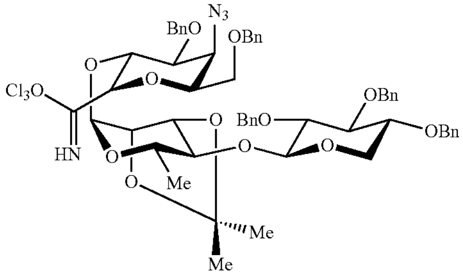

26

1. Step A: Synthesis of protected xylose-rhamnose-azidogalactose trisaccharide 24 by dehydrative glycosylation of protected 4-azido-4-deoxygalactose 21 with protected xylose-rhamnose disaccharide 23 (24): In a 25-mL modified Schlenk flask, $Ph_2SO$ (171 mg, 0.85 mmol, 3.2 equiv.) is dissolved in DCM (3.2 mL). To this clear, colorless solution, $Tf_2O$ (76 μL, 0.45 mmol, 1.7 equiv.) is injected via gas-tight syringe at −78° C. After 10 s, the solution turns pink, then purple, and quickly dissipates back to a clear, colorless solution.

2. A precooled solution of azeotropically dried disaccharide hemiacetal 23 (185 mg, 0.30 mmol, 1.1 equiv.) in DCM (1 mL) is added to the reaction mixture at −42° C. via cannula from a flame-dried, 5-mL pear-shaped Schlenk flask; then additional DCM (1 mL) is added to rinse the source flask and transferred to the reaction flask.

3. The reaction mixture is stirred at −42° C. for 15 min, then TBP (190 mg, 0.77 mmol, 3.0 equiv.) is added, and the mixture is further stirred at −42° C. for 1 h.

4. A precooled solution of protected 4-azido-4-deoxygalactose 21 (141 mg, 0.26 mmol, 1.0 equiv.) in DCM (1 mL) is added to the reaction mixture via cannula from a flame-dried, 5-mL pear-shaped Schlenk flask, at which point white fumes develop. Additional DCM (1 mL) is added to rinse the source flask and transferred to the reaction flask.

5. The reaction mixture is stirred at −42° C. for 16.5 h and at 0° C. for 1 h, then concentrated.

6. Purification by silica gel chromatography (hexanes/EtOAc, 99:1 to 50:1 to 6:1) gives a mixture of monosaccharide starting material (21) and trisaccharide product (24) as a yellow oil (460 mg). Additional purification of this mixture by silica gel chromatography (hexanes/EtOAc, 10:1 to 6:1) provides the protected trisaccharide 24 (231 mg, 79%) as a clear oil.

7. Step B: Synthesis of trisaccharide hemiacetal 25 by anomeric desilylation of protected xylose-rhamnose-azido-galactose trisaccharide 24. In a 250-mL modified Schlenk flask, the protected trisaccharide 24 (575 mg, 0.51 mmol, 1.0 equiv.) is dissolved in THF (50 mL) and the solution is cooled to 0° C.

8. A precooled (0° C.) solution of commercially available TBAF (1 M in THF) (0.76 mL, 0.76 mmol, 1.5 equiv.) and AcOH (35 μL, 0.61 mmol, 1.2 equiv.) in THF (50 mL) is added dropwise via cannula to the reaction flask over 50 min at 0° C.

9. The reaction mixture is stirred for an additional 5 min at 0° C., then quenched by addition of saturated aqueous $NaHCO_3$ solution (20 mL).

10. The contents are transferred to a separatory funnel, EtOAc (125 mL) and brine (50 mL) are added, and the organic phase is separated. The aqueous layer is extracted with EtOAc (2×200 mL) and the combined organic phases are dried over anhydrous magnesium sulfate, filtered, and concentrated.

11. The resulting oil is passed through a plug of silica gel eluted with EtOAc, and the eluate is concentrated to afford the trisaccharide hemiacetal 25 (402 mg, 82%) as a white foam, which is taken directly to the next step without further purification.

12. Step C: Synthesis of protected xylose-rhamnose-azidogalactose trisaccharide trichloroacetimidate 26 by activation of protected xylose-rhamnose-azidogalactose trisaccharide 25. In a 100-mL round-bottomed flask, the hemiacetal 25 (200 mg, 0.21 mmol, 1.0 equiv.) is dissolved in DCM (32 mL) and the solution is cooled to 0° C.

13. $Cl_3CCN$ (0.32 mL, 3.2 mmol, 1.6 equiv.) is added followed by DBU (0.1 mL, 0.67 mmol, 3.3 equiv.) and the reaction is allowed to warm to rt.

14. After stirring for 13.5 h, the mixture is concentrated to afford an oil.

15. Purification by silica gel chromatography (hexanes/EtOAc, 6:1 with 0.5 vol % $Et_3N$) (In absence of Et 3 N, prolonged chromatography on silica gel when purifying glycosyl trichloroacetimidates leads to progressive hydrolysis of the product.) affords the linear trisaccharide imidate 26 (230 mg, >99%) as a yellow foam.

Example 3: Modular, Convergent Assembly of Saponin Domain Fragments

Part A: Synthesis of Protected Aminogalactose Saponin

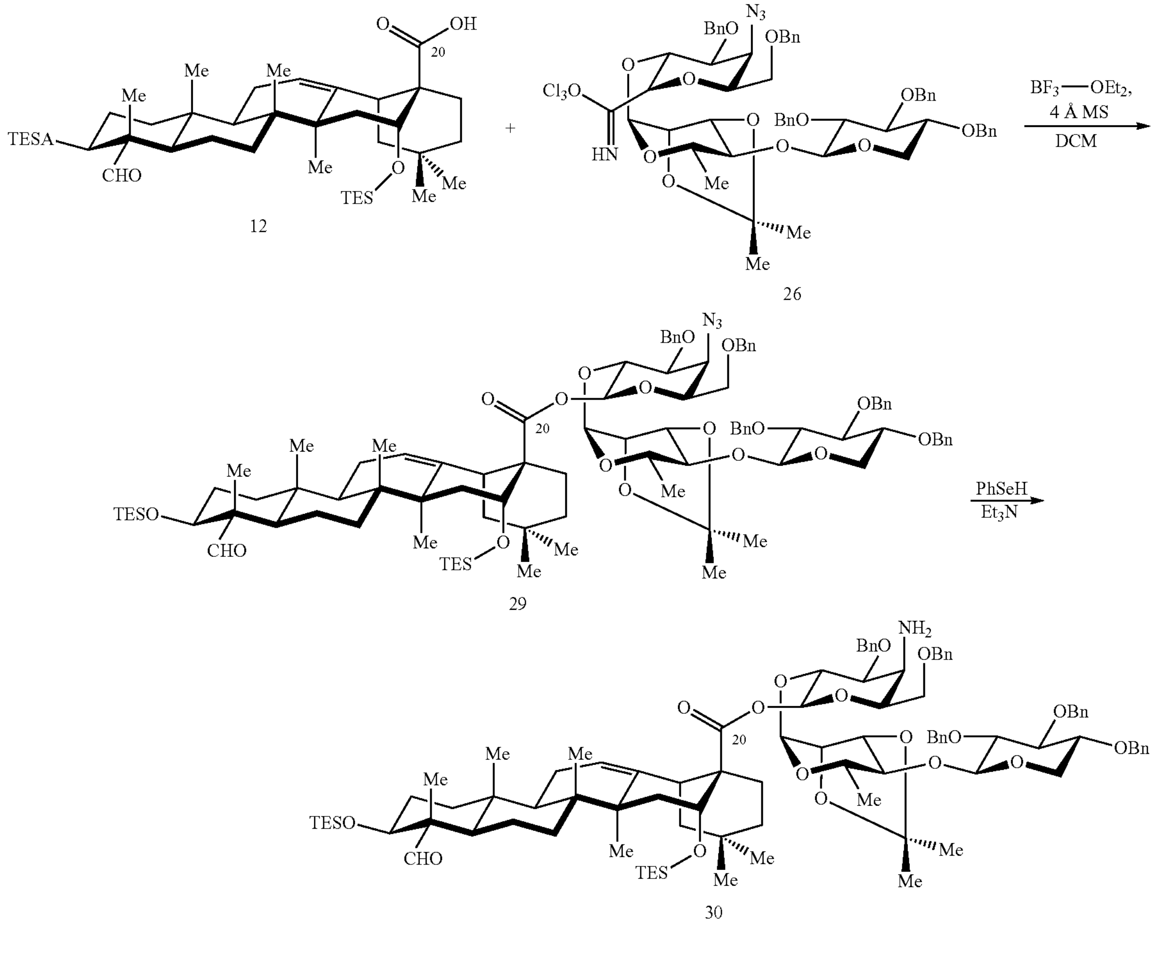

12

26

29

30

1. Step A Synthesis of protected azidogalactose saponin 29 by glycosylation of protected quillaic acid 12 with 5 protected xylose-rhamnose-azidogalactose linear trisaccharide 26. In a 25-mL modified Schienk flask, the selectively protected quillaic acid triterpene 12 (38 mg, 49 μmol, 1.05 equiv.) and the trisaccharide imidate 26 (52 mg, 47 μmol, 1.0 equiv.) are azeotroped from toluene (3×1 mL) under high vacuum, then dissolved in DCM (7 mL) and powdered 4 Å MS (80 mg) is added to the solution.

2. The mixture is stirred for 30 min at rt, then cooled to −42° C. Freshly distilled $BF_3OEt_2$ (1.2 μL, 9.0 μmol, 0.2 equiv.) is injected via gas-tight syringe and the reaction mixture is stirred for another 30 min at −42° C.

3. The reaction is quenched by addition of $Et_3N$ (0.2 mL) and the mixture is concentrated by rotary evaporation.

4. Purification by silica gel chromatography (benzene with 0.5 vol % $Et_3N$ to benzene/EtOAc, 97:3) affords the triterpene-linear trisaccharide conjugate 29 (56 mg, 72%) as a white solid.

5. Step B: Synthesis of protected aminogalactose saponin 30 by reduction of protected azidogalactose saponin 29. In a 50-mL modified Schlenk flask, PhSeSePh (187 mg, 0.6 mmol, 1.0 equiv.) is dissolved in THF (6 mL) and $H_3PO_2$ (50% in water) (0.72 mL, 6.6 mmol, 11 equiv.) is added via syringe.

6. The yellow solution is heated at 40° C. for 1 h until it turns colorless.

7. The reaction mixture is removed from the heat, diluted with benzene (6 mL) and distilled water (6 mL), and stirred vigorously for 5 min under Ar. The lower aqueous phase of the resulting biphasic suspension is removed by glass pipette and the remaining organic layer is dried over anhydrous sodium sulfate while stirring.

8. This freshly prepared solution of PhSeH (~1.1 mmol, 30 equiv.) is then cannula transferred under Ar to a 100-mL reaction Schlenk flask containing a solution of the azeotropically dried saponin azide 29 (62 mg, 37 μmol, 1.0 equiv.) in $Et_3N$ (28 mL). Upon addition, a white precipitate is formed and the solution becomes bright yellow.

9. The reaction mixture is stirred for 8 h at 38° C., then concentrated to afford a yellow-white solid.

10. Purification by silica gel chromatography (benzene/EtOAc, 90:10 to 85:15) affords the truncated saponin amine 30 (49 mg, 80%) as a glassy solid.

Part B: Synthesis of Protected Aminoacyl Saponin 32

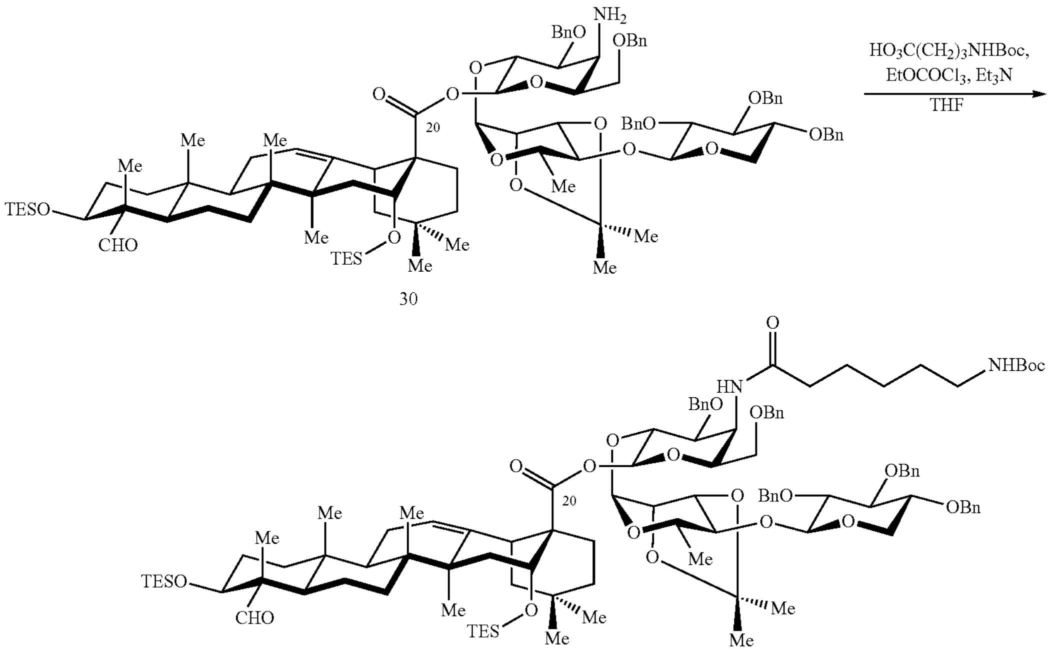

30

32

1. In a 10-mL pear-shaped Schlenk flask, 6-(Boc-amino) hexanoic acid (45.0 mg, 0.20 mmol, 11.5 equiv.) is dissolved in THF (2.5 mL), then $Et_3N$ (213 μL, 1.53 mmol, 90 equiv.) is added. To this clear, colorless solution at 0° C., EtOCOCl (16 μL, 0.17 mmol, 10 equiv.) is injected via gas-tight syringe.

2. The resulting turbid white mixture is stirred for 2.5 h at 0° C., and then cannula transferred at 0° C. into a 10-mL, Schlenk flask containing a neat film of azeotropically dried (3×1 mL toluene) saponin amine 30 (28 mg, 17.0 μmol, 1.0 equiv.).

3. The turbid white reaction mixture is stirred for 1.5 h at 0° C., then quenched with water (0.2 mL) to give a clear, colorless solution.

4. The mixture is diluted with saturated aqueous $NaHCO_3$ solution (30 mL) and the aqueous phase is extracted with DCM (3×25 mL). The combined organic layers are dried over anhydrous sodium sulfate, filtered, and concentrated (After quenching the reaction with water, the mixture can also be directly concentrated by rotary evaporation without the need for performing the described aqueous work-up).

5. Purification by silica gel chromatography (hexanes/EtOAc, 2:1 with 0.5 vol % Et 3 N) (Elution with 9:1 to 5:1 benzene/EtOAc (0.5 vol % Et 3 N) can also be used for the silica gel chromatography purification) affords the truncated, fully protected aminoacyl saponin 32 (28 mg, 88%) as a white glassy solid.

Example 4: Global Deprotection of Protected Aminoacylated Saponins

Part A: Synthesis of Aminoacyl Saponin 34 (Compound I-6) by Hydrogenolysis and Acid Hydrolysis of Protected Aminoacyl Saponin 32

3. The suspension is filtered through a 0.45 μm nylon syringe filter, washed with MeOH (3×30 mL) and concentrated. Successful debenzylation is assessed by the disappearance of aromatic resonances by $^1$HNMR in methanol-$d_4$.

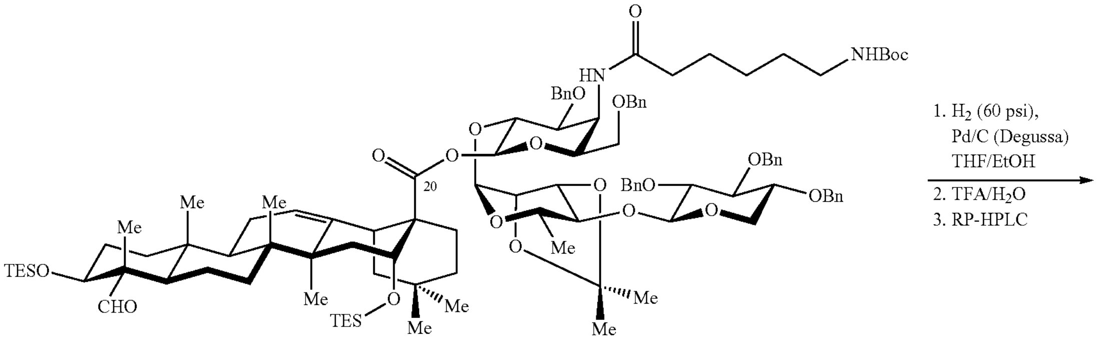

32

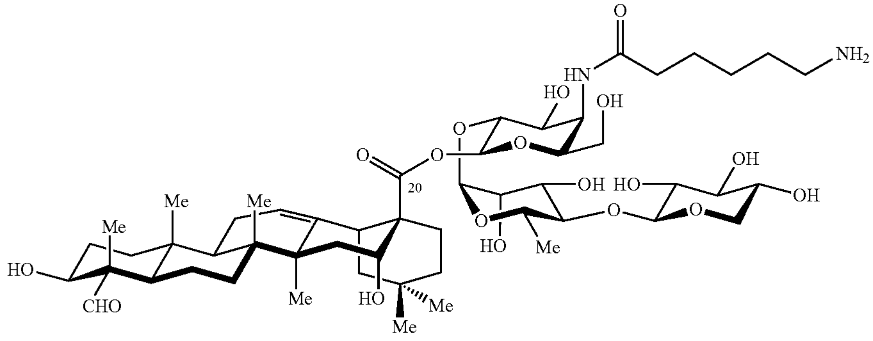

1. In a 50-mL round-bottomed flask, the fully protected truncated saponin 32 (68 mg, 36.6 μmol, 1.0 equiv.) is dissolved in THF/EtOH (1:1) (20 mL), then 10% (dry basis) Pd/C, wet Degussa type E101 NE/W (390 mg, 0.18 mmol, 5.0 equiv.) is added.

2. The reaction mixture is stirred under an atmosphere of $H_2$ (50 psi) for 24 h at rt using a high-pressure bomb reactor (In similar saponin triterpene variants lacking the branched trisaccharide domain, hydrogenolysis under hydrogen atmosphere at balloon pressure for 12 h is sufficient to provide the corresponding debenzylated products).

4. In a 25-mL round-bottomed flask, the resulting crude mixture is dissolved in a precooled (0° C.) solution of TFA/water (3:1) (8 mL).

5. The reaction mixture is stirred for 2 h at 0° C. and then concentrated under high vacuum at 0° C. to give a white solid residue.

6. This crude product is dissolved in water/MeCN (4:1) (20 mL) and purified by RP-HPLC using a linear gradient of 30→70% MeCN in water (0.05 vol % TFA) over 15 min. The fully deprotected, truncated saponin 34 elutes as a main, single peak and is obtained as a fluffy white solid (28 mg, 74%) after lyophilization.

Example 5: Late Stage Acylation of Acyl Chain Domain Amine to Form Fully Elaborated Saponin 4 (Compound I-8)

Step A: Synthesis of Fully Elaborated Saponin 4, (Compound I-8), Lacking the Branched Trisaccharide Domain, by Selective 4-Iodobenzoylation of Free Amine in Aminoacyl Saponin 34

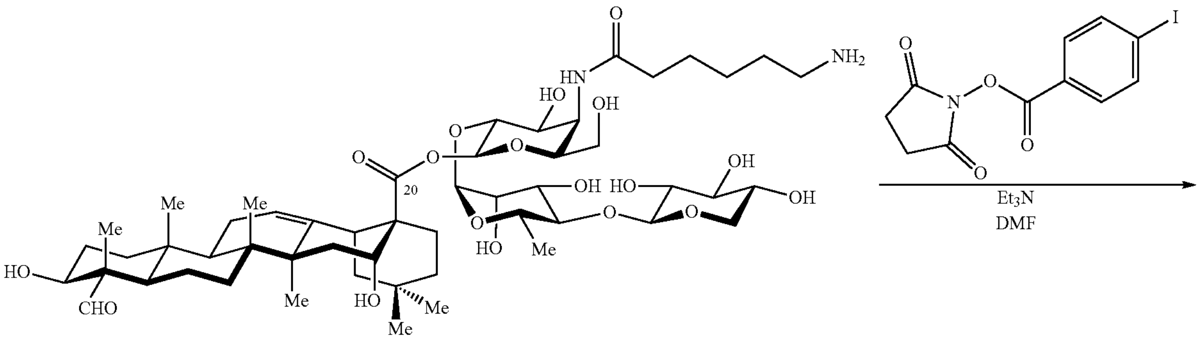

34

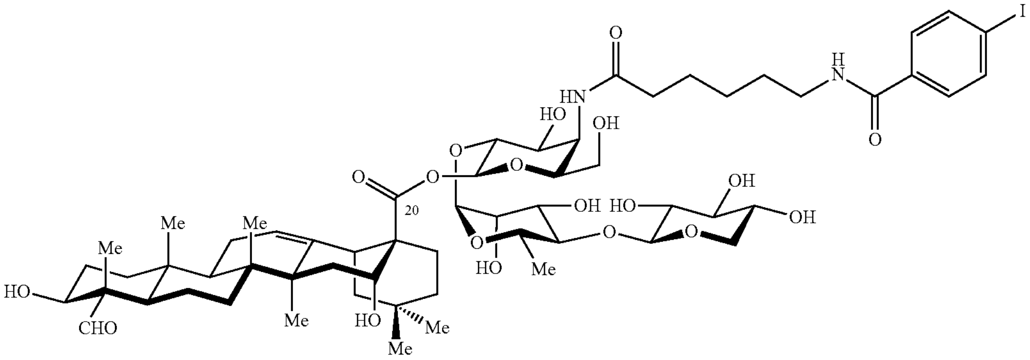

4

1. In a 5-mL pear-shaped flask equipped with a rubber septum fitted with an Ar inlet needle, amine-terminating truncated saponin 34 (2.1 mg, 2.0 μmol, 1.0 equiv.) is dissolved in DMF (0.4 mL). $Et_3N$ (11 μL, 0.08 mmol, 40 equiv.) is injected followed by dropwise addition of a solution of N-succinimidyl 4-iodobenzoate (4.0 mg, 10 μmol, 5.8 equiv.) in DMF (0.2 mL) under Ar via gas-tight syringe.

2. The reaction mixture is stirred for 2 h at rt, then diluted with 30% MeCN/water (2.3 mL), and directly purified by RPHPLC using a linear gradient of 30-70% MeCN in water (0.05 vol % TFA) over 15 min.

3. The fully elaborated, truncated saponin 4 (Compound I-8) (1.7 mg, 67%) is obtained as a white powder after lyophilization.

Example 6: Isolation and Selective Protection of Branched Trisaccharide-Triterpene Prosapogenin

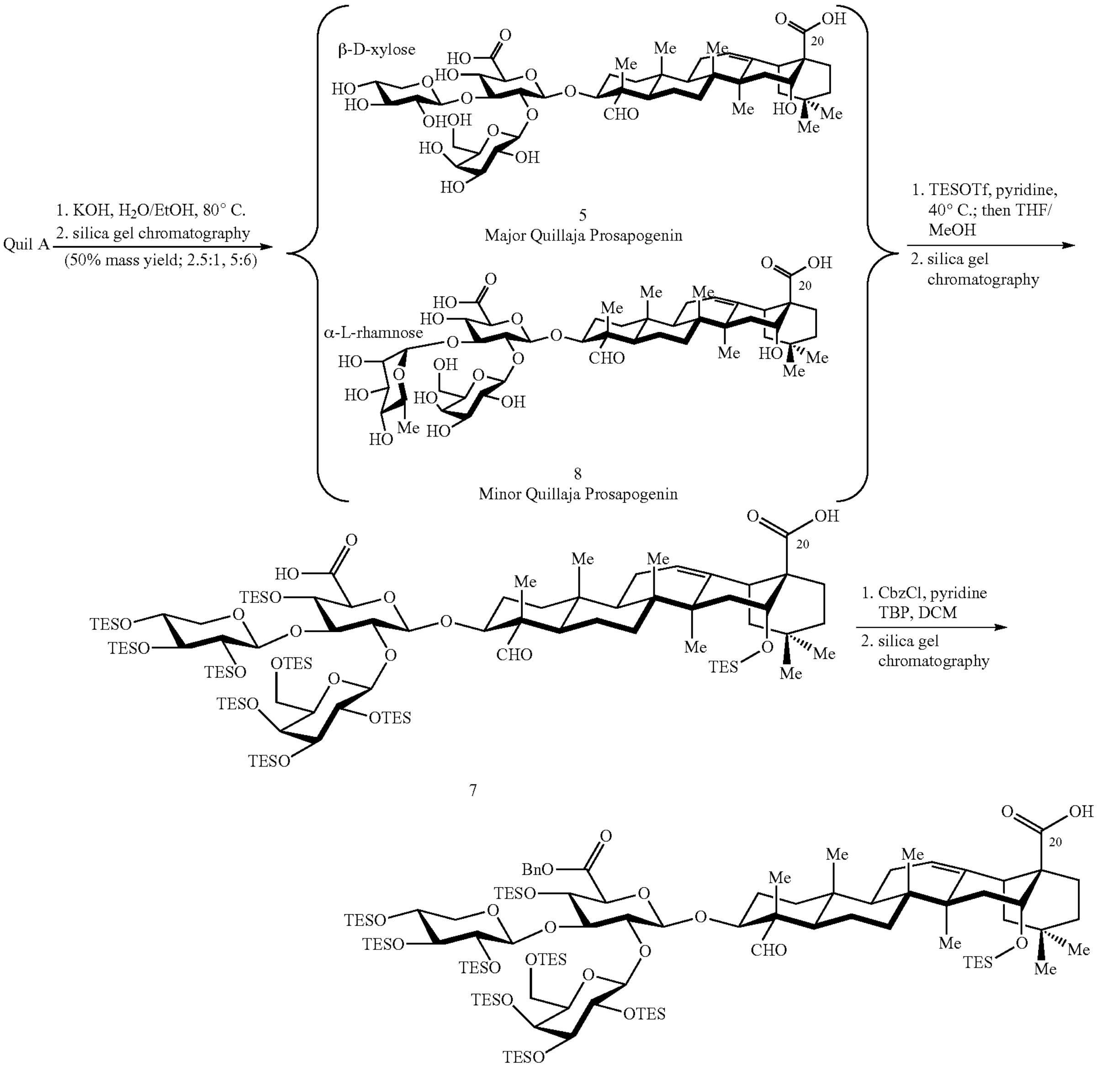

5
Major Quillaja Prosapogenin

8
Minor Quillaja Prosapogenin

7

8
Protected Quillaja Prosapogenin

Part A: Isolation of branched trisaccharide-triterpene prosapogenins from Quil A.

1. In a 250-mL round-bottomed flask equipped with a reflux condenser, Quil A (1.15 g) and potassium hydroxide (0.97 g, 17 mmol) are suspended in EtOH/water (1:1) (50 mL), then the mixture is heated to 80° C. for 7 h.

2. The reaction is cooled to 0° C., neutralized with 1.0 N HCl, and concentrated to approximately one-half volume (care must be taken to avoid excessive foaming and bumping; water bath should be kept at 35° C. and pressure decreased slowly).

3. The mixture is frozen and lyophilized, and the resulting dry solid is purified by silica gel chromatography ($CHCl_3$/MeOH/water/AcOH, 15:9:2:1). The major product corresponding to the main spot observed by TLC is isolated by concentrating the desired fractions.

4. The resulting solid is dried by azeotropic removal of solvents with toluene (2×20 mL) and lyophilized in MeCN/water (1:1) (3×15 mL) to provide a mixture of prosapogenins (5:6, 2.5:1) as a light tan foam (~0.55 g, 50% mass yield). These xylose- and rhamnose-containing prosapogenins 5 and 6, respectively, correspond to the two most abundant trisaccharide-triterpene fragments found in QS *saponins*, and are advanced to the next protection step without further purification.

Part B: Synthesis of Triethylsilyl (TES)-Protected Prosapogenin by Selective Protection of Prosapogenin Hydroxyl Groups 1. In a 25-mL modified Schlenk flask, the solid mixture of prosapogenins 5 and 6 (~0.55 g) is azeotroped from pyridine (5 mL), then additional pyridine (8 mL) is added, followed by TESOTf (2.0 mL, 8.8 mmol).

2. The reaction mixture is stirred for 2.75 days, then TESOTf (0.3 mL, 1.3 mmol) is added, followed by two further additions (0.1 mL each, 0.44 mmol each) 24 h and 48 h later, respectively (the last extra addition of TESOTf is situation-dependent and only required if the reaction is still incomplete after the first 4 days).

3. After a total of 5 days, the mixture is concentrated and passed through a short plug of silica gel eluted with hexanes/EtOAc (4:1 to 2:1). The eluate is concentrated, the resulting yellow oil is dissolved in MeOH/THF (1:1) (20 mL), and the solution is stirred for 3.5 days to remove the silyl esters by solvolysis.

4. The reaction mixture is concentrated and the resulting mixture of xylose- and rhamnose-containing $(TES)_9$-protected prosapogenin diacids is separated by silica gel chromatography (hexanes/EtOAc, 4:1 to 2:1) to afford purified xylose-containing protected prosapogenin 7 (~0.25 g, ~22% yield) as a white solid.

Part C: Synthesis of Protected *Quillaja* Prosapogenin 8 by Selective Esterification of Glucuronic Acid Carboxylic Acid in Protected Prosapogenin 7

1. In a 10-mL modified Schlenk flask, the prosapogenin diacid 7 (81 mg, 41 μmol, 1.0 equiv.) is dissolved in DCM (0.7 mL) and pyridine (30 μL, 0.37 mmol, 9.0 equiv.) and TBP (102 mg, 0.41 mmol, 10 equiv.) are added, followed by benzyl chloroformate (15 μL, 0.11 mmol, 2.6 equiv.).

2. The reaction is stirred for 6 h, additional benzyl chloroformate (3.0 μL, 21 μmol, 0.51 equiv.) is added (the extra addition of CbzCl after the first 6 h depends on the progress of the reaction in each particular case; when purifying by silica gel chromatography, elution with benzene/EtOAc (100:0 to 24:1) can also be considered) and the reaction is stirred for another 20 h.

3. The mixture is concentrated and purified by silica gel chromatography (hexanes/EtOAc, 20:1 to 7:1) to afford selectively glucuronate-protected prosapogenin 8 (58 mg, 68%) as a white solid.

Example 7: Modular, Convergent Assembly of Saponin Domain Fragments

Part A: Synthesis of Protected Aminogalactose Saponin 28

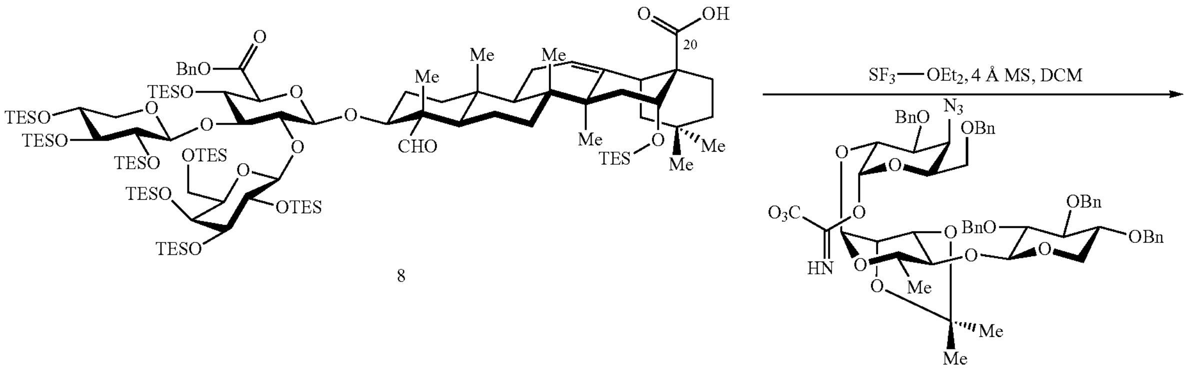

8

26

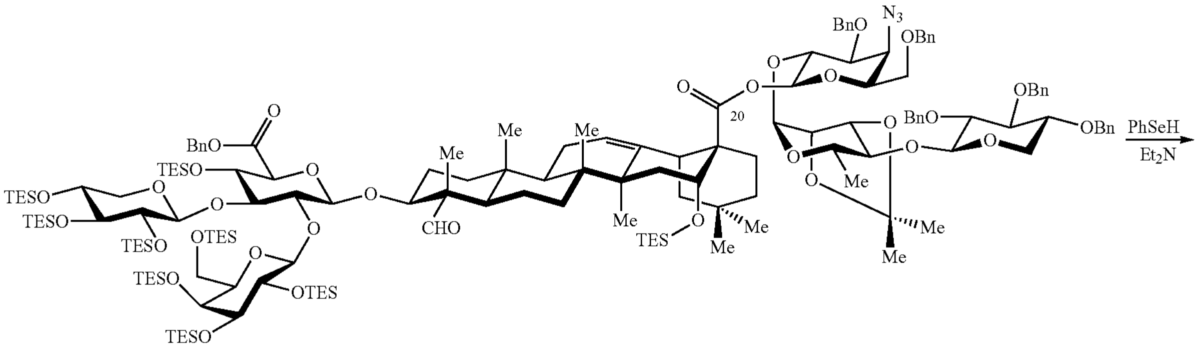

27

-continued

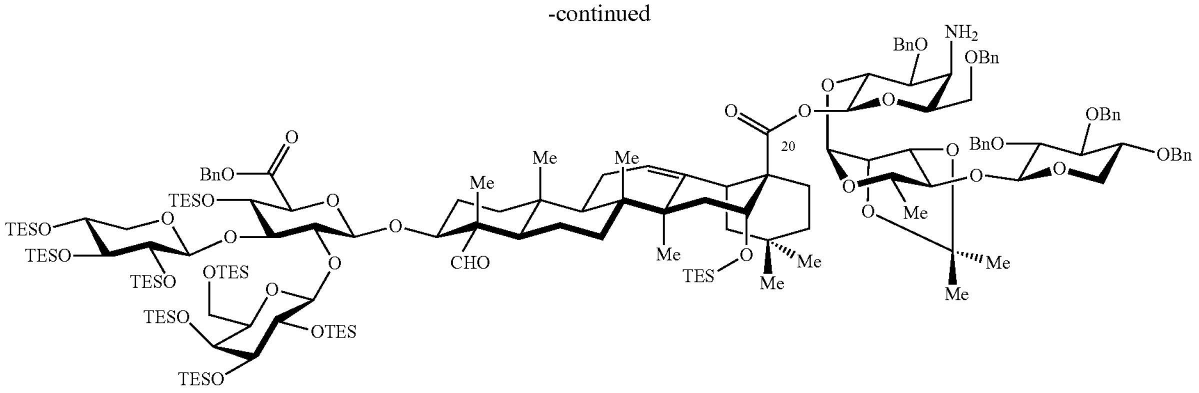

28

1. Step A: Synthesis of protected azidogalactose saponin 27 by glycosylation of branched trisaccharide-triterpene prosapogenin 8 with protected xylose-rhamnose-azidogalactose linear trisaccharide 26. In a 50-mL modified Schlenk flask, the selectively protected prosapogenin 8 (653 mg, 0.32 mmol, 1.5 equiv.) and the trisaccharide imidate 26 (230 mg, 0.21 mmol, 1.0 equiv.) are azeotropically dried from toluene (3×3 mL) under high vacuum, then dissolved in DCM (10 mL).

2. Powdered 4 Å MS (1 g) is added and the suspension is stirred for 2 h at rt. The opaque, white mixture is then cooled to −78° C. and freshly distilled $BF_3 \cdot OEt_2$ (15 μL, 0.23 mmol, 1.1 equiv.) is injected via gas-tight syringe.

3. The reaction mixture is stirred at −78° C. for 6 h, passed through a plug of silica gel, and the filtrate is concentrated.

4. Purification by silica gel chromatography (hexanes/EtOAc, 9:1 to 4:1) affords the prosapogenin-linear trisaccharide conjugate 27 (322 mg, 73%) as a glassy solid.

5. Step B: Synthesis of protected aminogalactose saponin 28 by reduction of protected azidogalactose saponin 27. In a 50-mL modified Schlenk flask, PhSeSePh (313 mg, 1.0 mmol, 1.0 equiv.) (Caution: selenium compounds are highly toxic and have an unpleasant odor. Phenylselenol itself is extremely noxious. The in-situ preparation of phenylselenol solution by reduction of diphenyldiselenide circumvents the need to handle phenylselenol directly, but manipulation of the selenide-containing solution that will be added to the reaction flask is necessary. Care should be taken when handling selenium reagents and all manipulations should be performed in a fumehood wearing protective gloves and safety glasses, including weighing of the diphenyldiselenide starting material. A bleach solution should be prepared in advance to treat all used glassware and possibly early column fractions as well, to oxidize any remaining trace selenides. Bleach solution should also be placed in the solvent trap of the rotary evaporator, which should be thoroughly cleaned after use and ideally contained within the fumehood.) is dissolved in THF (8 mL) and $H_3PO_2$ (50% in water) (1.2 mL, 11.0 mmol, 11 equiv.) is then added via syringe.

6. The yellow solution is heated at 40° C. for 1 h until it turns colorless.

7. The reaction mixture is removed from the heat, diluted with benzene (8 mL) and distilled water (8 mL), and stirred vigorously for 5 min under Ar. The lower aqueous phase of the resulting biphasic suspension is removed by syringe (or glass pipette) under positive pressure of Ar, and anhydrous sodium sulfate is added to the Schlenk flask to dry the remaining organic layer while stirring.

8. This freshly prepared solution of PhSeH (~1.9 mmol) is then added under Ar via cannula transfer to a 250-mL reaction Schlenk flask containing a solution of the azeotropically dried saponin azide 27 (322 mg, 0.11 mmol, 1.0 equiv.) in $Et_3N$ (50 mL). Upon addition, a white precipitate is formed and the solution turns bright yellow.

9. The reaction mixture is stirred for 3 h at 40° C., then concentrated to give a yellow-white solid.

10. Purification by silica gel chromatography (hexanes/EtOAc, 4:1 to EtOAc with 0.5 vol % $Et_3N$) affords the saponin amine 28 (256 mg, 87%) as a glassy solid (another alternative experimental procedure to perform this azide reduction step to give the corresponding saponin amine is the treatment of the starting material in $Et_3N$ with hydrogen sulfide (gas) as follows: An excess of hydrogen sulfide from a steel cylinder is bubbled via cannula (long steel needle) through an ice-cooled solution of the saponin azide (~45 mg, ~0.015 mmol, 1.0 equiv.) in pyridine/$Et_3N$ (3.5:1) (4.5 mL) for 2 min. Vent needle and cannula are removed from septum, which is sealed with Teflon tape and parafilm, and the reaction mixture is stirred overnight at rt. The dark green solution is then purged of excess hydrogen sulfide with a stream of nitrogen, and the resulting light-orange solution is concentrated by rotary evaporation. Purification of the residue by silica gel chromatography (hexanes/EtOAc, 1.0 vol % $Et_3N$) yields the desired saponin amine product (~40 mg, 80-90% yield)).

Part B: Synthesis of Protect Aminoacyl Saponin 31

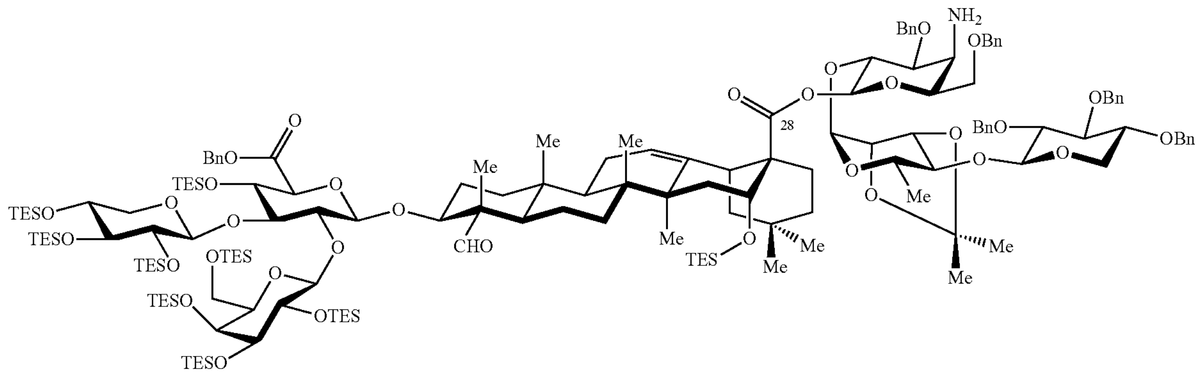

28

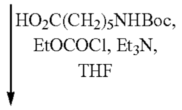

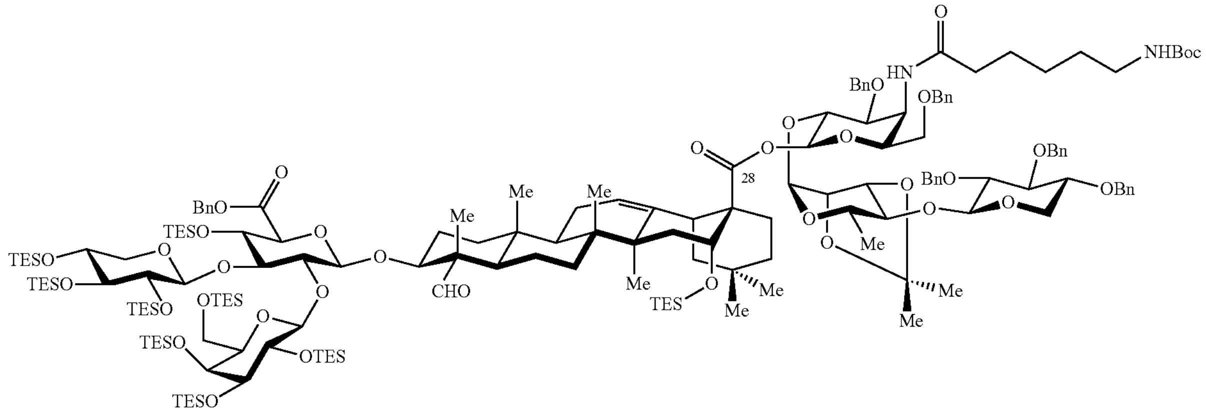

31

1. In a 5-mL pear-shaped Schlenk flask, commercially available 6-(Boc-amino)hexanoic acid ($HO_2C(CH_2)_5NH$-Boc) (19.9 mg, 86 μmol, 10 equiv.) is dissolved in THF (0.9 mL), then $Et_3N$ (0.11 mL, 0.77 mmol, 90 equiv.) is added. To this clear, colorless solution at 0° C., EtOCOCl (7.3 μL, 77 μmol, 9.0 equiv.) is injected via gas-tight syringe.

2. The turbid white mixture is stirred for 3 h at 0° C. The prosapogenin-linear trisaccharide saponin amine 28 (26 mg, 8.6 μmol, 1.0 equiv.) is then added, and the reaction is stirred for 1.5 h at rt.

3. Water (0.1 mL) is added to quench the reaction, at which point the solution turns from turbid white to clear yellow. After addition of more water (0.1 mL), the resulting immiscible mixture is concentrated.

4. Purification by silica gel chromatography (toluene/EtOAc, 20:1 to 11:1) affords the aminoacyl, branched trisaccharide-containing saponin 31 (22 mg, 81%) as a white glassy solid.

Example 8: Global Deprotection of Protected Aminoacylated Saponins

Part A: Synthesis of Aminoacyl Saponin 33 by Hydrogenolysis and Acid Hydrolysis of Protected Aminoacyl Saponin 31

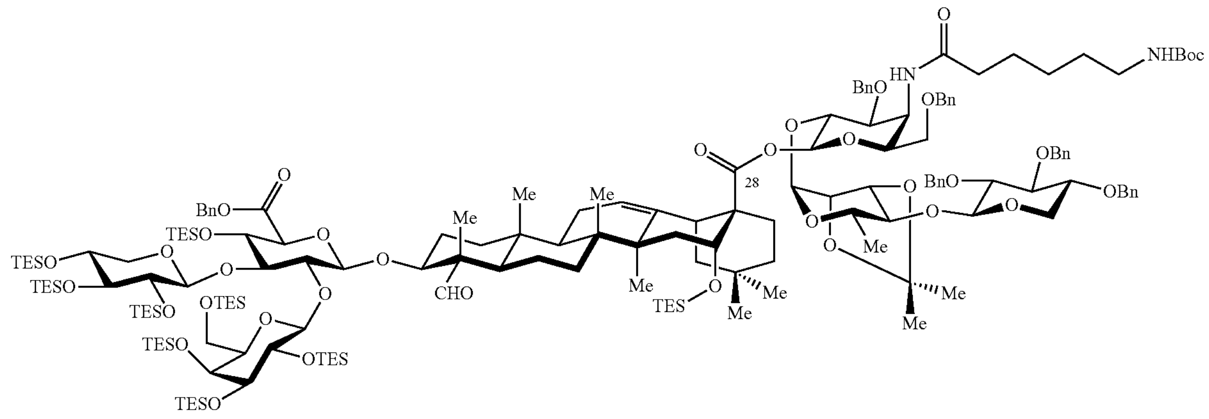

31

1. $H_2$ (50 psi), Pd/C (Degussa) THF/EtOH
2. TFA/$H_2O$
3. RP-HPLC

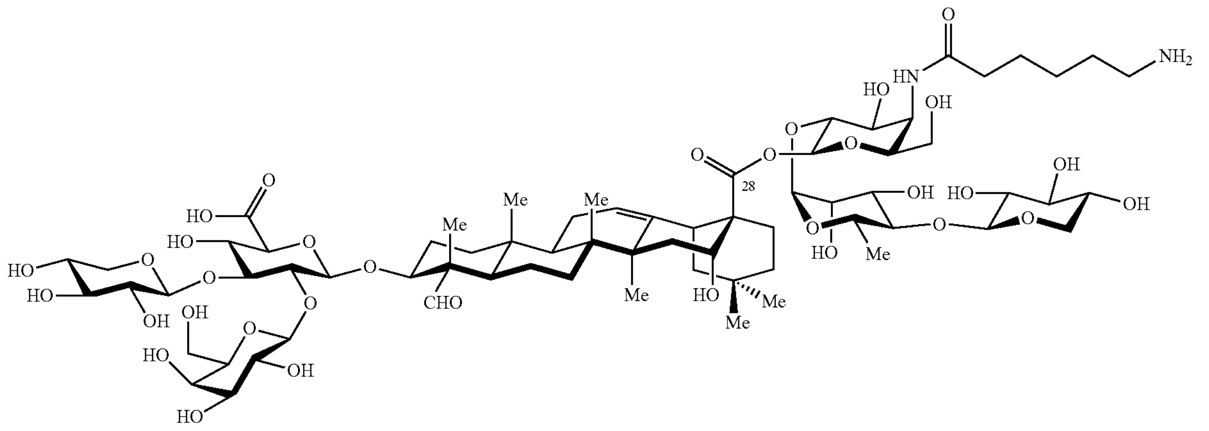

33

1. In a 100-mL round-bottomed flask, fully protected, branched trisaccharide-containing saponin 31 (240 mg, 75 μmol, 1.0 equiv.) is dissolved in THF/EtOH (1:1) (20 mL), then 10% (dry basis) Pd/C, wet, Degussa type E101 NE/W (140 mg, 66 μmol, 0.9 equiv.) is added (Caution: hydrogenolysis reactions pose a significant fire hazard. Caution should be taken when handling flammable palladium on carbon as well as hydrogen gas, which increases the risk of explosion.).

2. The reaction mixture is stirred under $H_2$ atmosphere (50 psi) for 24 h at rt using a high-pressure bomb reactor, and the suspension is filtered through a 0.45 μm nylon syringe filter.

3. The palladium is washed thoroughly with MeOH (3×100 mL) and the clear filtrate is concentrated. Successful debenzylation is assessed by disappearance of aromatic resonances by $^1$HNMR in methanol-$d_4$.

4. In a 50-mL round-bottomed flask, the resulting crude mixture of partially desilylated products is dissolved in a precooled (0° C.) solution of TFA/water (4:1) (10 mL).

5. The reaction mixture is stirred for 3 h at 0° C. and then concentrated under high vacuum at 0° C. to give a white solid residue (140 mg).

6. This crude product is dissolved in a solution of water/MeCN (4:1) and purified by RP-HPLC using a linear gradient of 20→35% MeCN in water (0.05 vol % TFA) over 10 min. The fraction containing the major, single peak is collected and lyophilized to dryness to afford the fully deprotected, free amine-containing saponin 33 (88 mg, 78%) as a fluffy white solid.

Example 9: Late-Stage Acylation of Acyl Chain Domain Amine to Form Fully Elaborated Saponin 3

Part A: Synthesis of Fully Elaborated Saponin 3 by Selective 4-Iodobenzoylation of Free Amine in Aminoacyl Saponin 33

HPLC using a linear gradient of 20-70% MeCN in water over 30 min.

4. The fraction corresponding to the peak containing the desired product, as assessed by mass spectrometry, is collected and lyophilized to dryness to afford the fully elaborated saponin 3(5.4 mg, 52%) as a white powder.

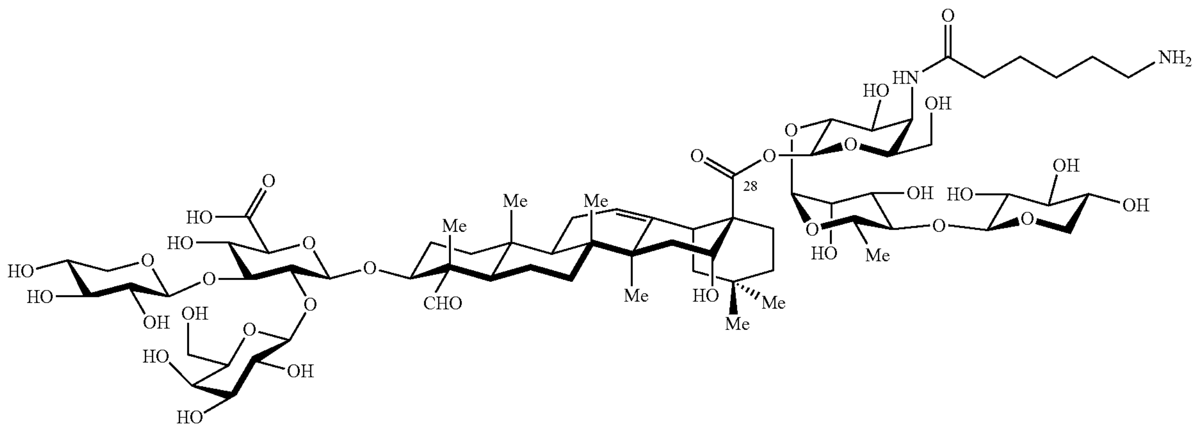

33

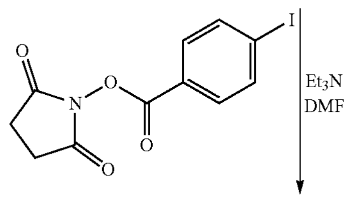

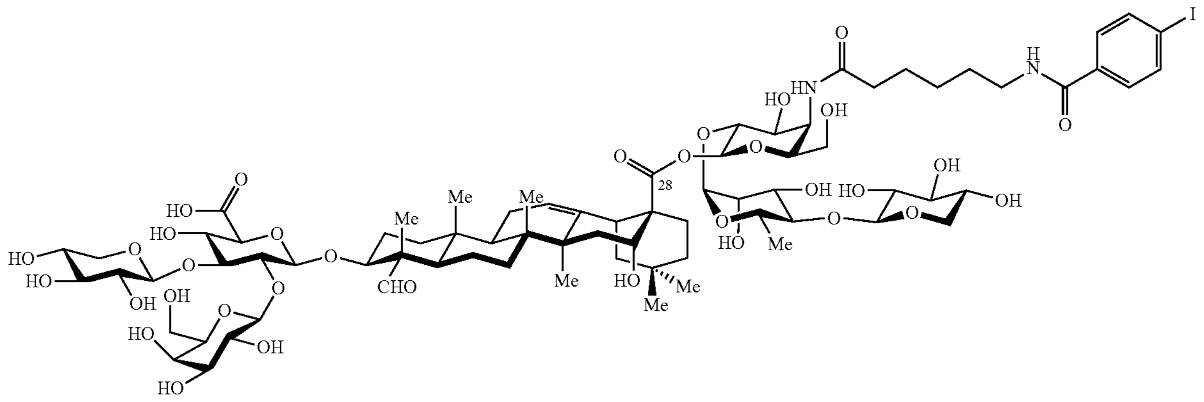

3

1. In a 10-mL round-bottomed flask equipped with a rubber septum fitted with an Ar inlet needle, amine-terminating saponin 33 (9.0 mg, 6.0 μmol, 1.0 equiv.) is dissolved in DMF (2.0 mL) and $Et_3N$ (50 μL, 0.36 mmol, 60 equiv.) is injected via gastight syringe.

2. The mixture is stirred for 50 min at rt and commercially available N-succinimidyl 4-iodobenzoate (20 mg, 60 μmol, 10 equiv.), dissolved in DMF (0.6 mL) under Ar, is then added dropwise via syringe from a 5-mL pear-shaped flask equipped with a rubber septum.

3. The reaction mixture is stirred for 1 h at rt, diluted with water/MeCN (4:1) (10 mL), and directly purified by RP-

Example 10: Total Synthesis of Compound I-4 (TQL-1055)

The total synthesis of Compound I-4 (TiterQuil-1-0-5-5/TQL-1055) is depicted in FIG. 6-8 of the present application. The numbering associated with the compounds in this example is not meant to correspond with other formula or compound numbering appearing throughout the remainder of the application, including other Figures, the claims, or Examples 1-9.

Figure 2:
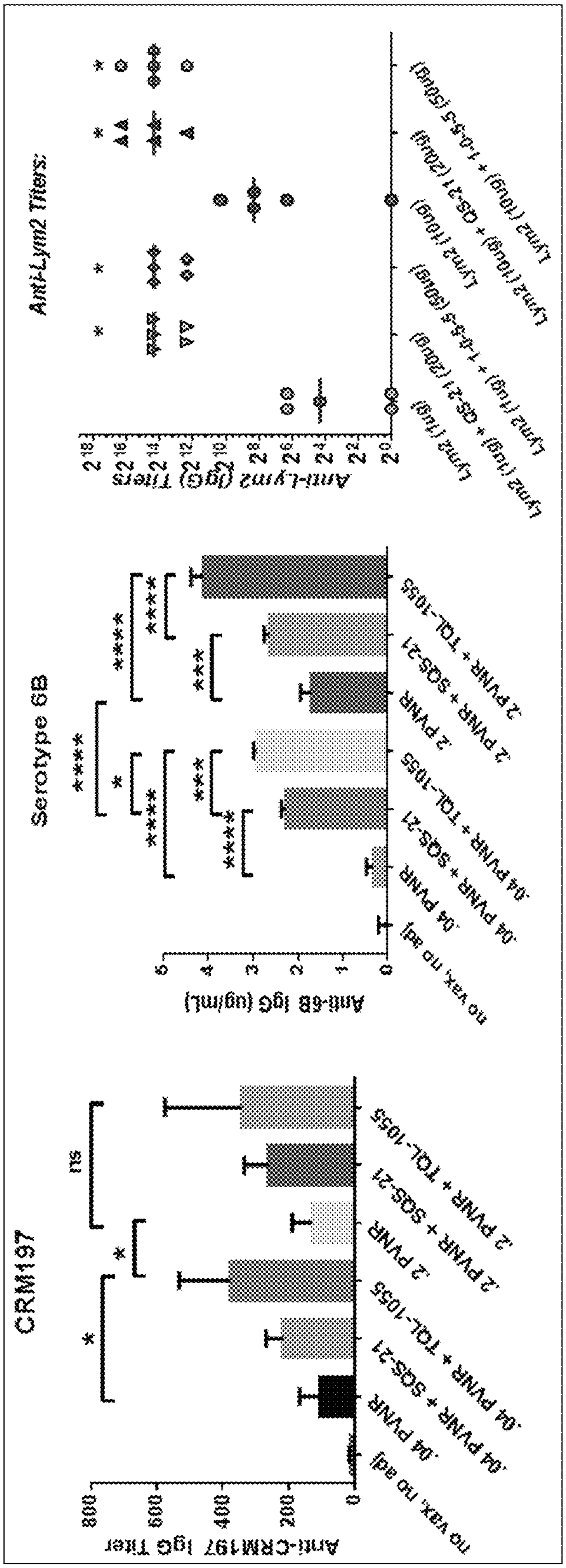
FIG. 2 depicts data showing the immunogenicity of high or low dose Prevnar-13 or of Lym2-CRM197 conjugate in combination with synthetic QS-21 (SQS-21) or Compound I-4 (TiterQuil-1-0-5-5/TQL-1055).

Example 11: Prevnar-13-CRM197 Conjugate Vaccine Adjuvanted with Synthetic Saponins The impact of synthetic QS-21 and TQL-1055 (Compound I-4) on antibody titers induced by the FDA approved human pneumococcal-CRM197 conjugate vaccine, Prevnar-13, was tested. Mice were immunized with Prevnar-13 in the presence or absence of synthetic saponin adjuvants at two different Prevnar dose levels (0.04 mcg and 0.2 mcg). Mice were immunized once at Day 0 and bled on Day 21 for serum analysis. FIG. 2 of the present application reports data obtained in this study, showing the immunogenicity of high or low dose Prevnar-13 or of Lym2-CRM197 conjugate in combination with synthetic QS-21 (SQS-21) or TQL-1055 (Compound I-4).

Figure 3:
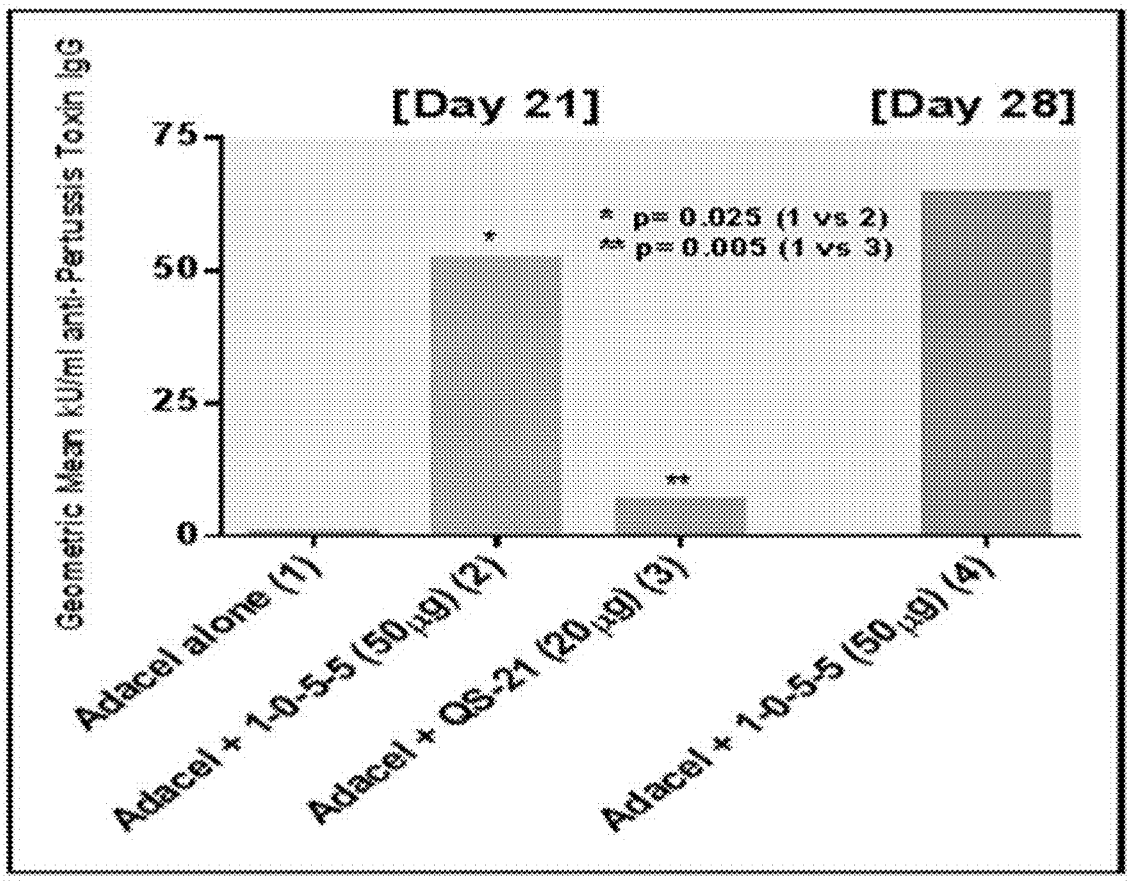
FIG. 3 depicts data showing immunogenicity of Adacel alone or in combination with Compound I-4 (TiterQuil-1-0-5-5/TQL-1055) or QS-21 (Pharm/tox study).

Example 11: Impact of TQL-1055 (Compound I-4) and QS-21 on Tdap Vaccine Adacel Immunogenicity Adacel doses containing 1, 0.3, and 0.1 mcg of pertussis toxin per mouse were administered subcutaneously (SC, with no immunological adjuvant), using 2 vaccinations 4 weeks apart, resulting in a mean of 1,618 mcg, 898 mcg, and 107 mcg respectively of anti-PT antibody per ml of serum drawn 2 weeks after the second vaccination. The 0.1 mcg dose was indistinguishable from unvaccinated controls (96 mcg/ml). A 0.5 mcg dose of Adacel was selected for a pharmacology/toxicology (pharm/tox) study. The serological results for this study are summarized in FIG. 3 of the present application. Antibody levels in the groups of 5 mice 2 weeks after the second SC immunization were augmented by 70 fold (726 to 52,344) with TiterQuil-1055 (TQL-1055/Compound I-4) (and further increased 2 weeks later) and 10 fold with QS-21 compared to immunization with Adacel alone. No weight loss was detected in the mice receiving 50 mcg of TiterQuil-1055 while the 20 mcg QS-21 injected mice lost 8-9% of their body weight.

Figure 4:
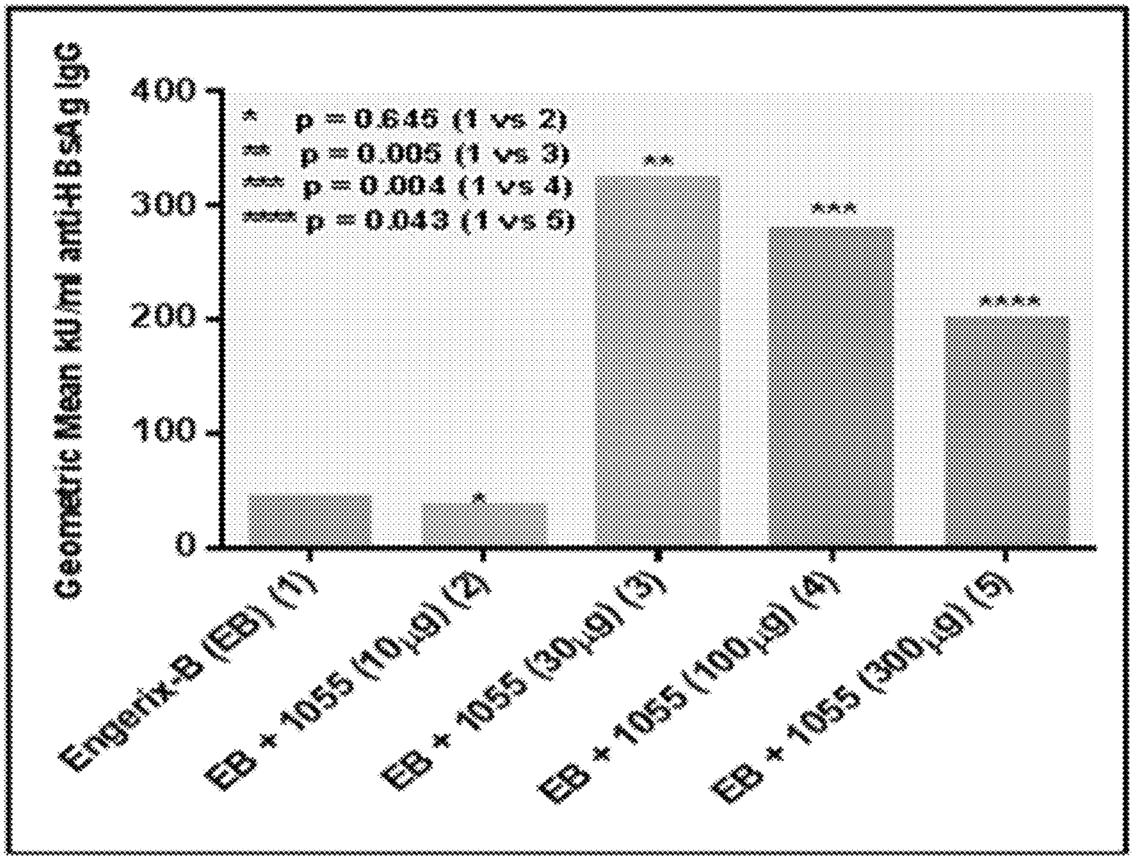
FIG. 4 depicts data showing immunogenicity of Engerix-B alone or in combination with 10, 30, 100 or 300 mcg of Compound I-4 (TiterQuil-1-0-5-5/TQL-1055).

Example 12: Impact of TiterQuil-1-0-5-5 and QS-21 on Hepatitis B Vaccine Engerix-B Immunogenicity Experiments were conducted with Engerix-B (HBV adult vaccine) in groups of 10 mice. Initially 3 mcg, 1 mcg, 0.3 mcg, 0.1 mcg, and 0.03 mcg Engerix-B doses per mouse were tested. Mean resulting anti-HBsAg antibody levels were 92,512 mcg/ml, 64,255 mcg/ml, 24,847 mcg/ml, 3,682 mcg/ml, and 910 mcg/ml respectively, with the 0.03 dose being indistinguishable from controls (821 mcg/ml). The 0.3 mcg dose of Engerix-B was selected for further studies and this dose was used mixed with various doses of TiterQuil-1055 (TQL-1055/Compound I-4). The resulting geometric mean antibody concentrations are summarized in FIG. 4 of the present application. While 10 mcg of TiterQuil-1055 appeared to have no serologic effect, mixture of 30 and 100 mcg TiterQuil-1055 with Engerix-B resulted in a >6 and 5-fold increase (respectively) in antibody levels compared to Engerix-B alone. Lack of antibody increase or decreasing responses at TiterQuil-1055 doses above 50 mcg per mouse has been a consistent finding. No weight loss was seen at the 30 mcg TiterQuil-1055 dose and only 4% and 5% at the 100 and 300 mcg doses.

Example 13: Results of a Pilot Pharmacology/Toxicology with Adacel QS-21 and TiterQuil-1055

A pharm/tox study was conducted in 7 groups of 5 mice: 1) PBS alone, 2) 50 mcg TiterQuil-1055, 3) 20 mcg QS-21, 4) Adacel 2.5 mcg pertussis toxin (⅕ the human dose), 5) Adacel+QS-21 (20 mcg QS-21), 6) Adacel+TiterQuil-1055 (50 mcg), 7) Adacel+TiterQuil-1055 (50 mcg). Mice were vaccinated SC on days 1 and 15, weighed daily, and bled and sacrificed on day 22, except for group 7 which was sacrificed on day 29. No changes in blood chemistry or hematology results were seen in any group. 7-9% weight loss was seen in all mice in groups 3 and 5 (in agreement with prior results of QS-21) and in no other mice. Histopathology of 33 different tissues was performed on all mice. Detected abnormalities were restricted to the liver. Moderate to severe hepatocellular cytoplasmic vacuolization was seen in all mice in groups 4-6 (completely attributable to the pertussis vaccine at this dose, groups 5 and 6 were no more severe than group 4) but no mice in groups 1 or 2. This abnormality was short lived and was no detected in group 7, which was sacrificed one week after groups 1-6. Mild vacuolar changes were seen in all mice in group 3 (QS-21 alone). No changes at all were seen in groups 1 and 2 (PBS and TiterQuil-1055).

Example 14: Stability and Hemolytic Activity of Compound I-4 (TQL-1055/TiterQuil-1-0-5-5)

Figure 5:
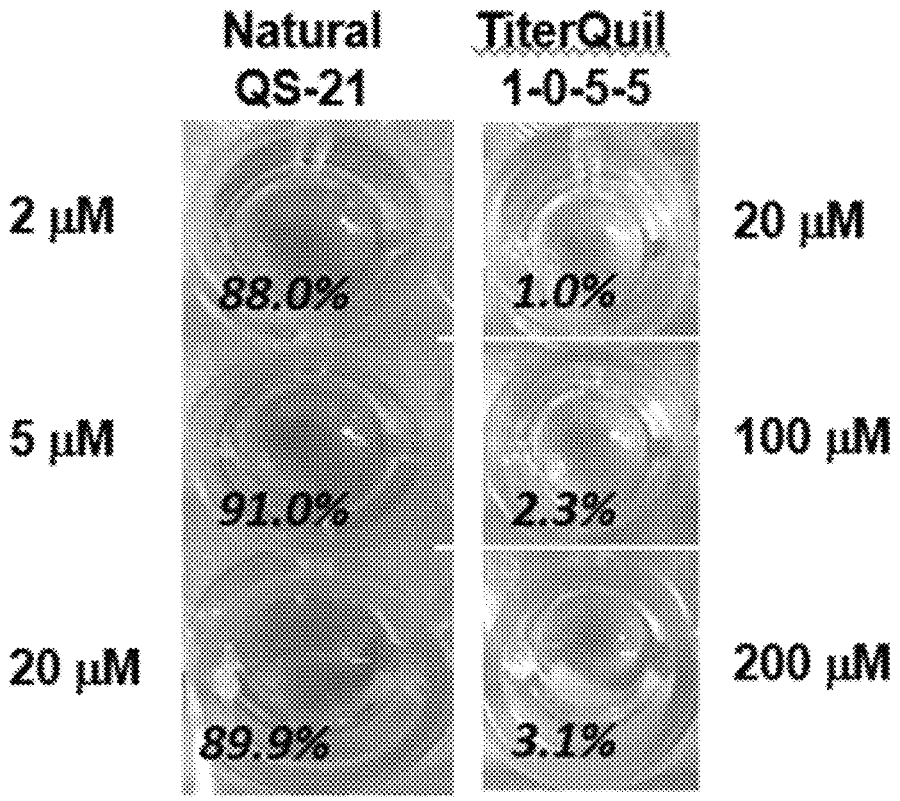
FIG. 5 depicts data showing the hemolytic activity of QS-21 at 2 uM, 5 uM and 20 uM, and Compound I-4 (TiterQuil-1-0-5-5/TQL-1055) at 20 uM, 100 uM and 200 uM. % Hemolytic activity reported as % of Triton-X100/SDS lysis control.

Natural and synthetic QS-21 (SQS-21 or SAPONEX®) and a variety of analogs were tested for hemolytic activity. This data clearly demonstrates that QS-21 is highly hemolytically active whereas several of the structural analogs, particularly Compound I-4 (TiterQuil-1-0-5-5/TQL-1055), demonstrated much lower or undetectable hemolytic activity in addition to increased stability. FIG. 5 depicts results a hemolytic assay performed with TiterQuil-1055. In a companion toxicity study three days after immunization, animals that received 20 mcg of QS-21 have lost 8-10% of their body mass on average, whereas PBS, TiterQuil-101 and TiterQuil-1055 recipients have gained 5% on average (normal weight gain in young mice). Without being bound by theory, hemolytic activity may be a direct result of degradation of QS-21 under physiologic conditions and TiterQuil-1055's lack of hemolytic activity may result from improved stability. After two weeks at 37° C., 20% of QS-21 degraded, whereas TiterQuil-1055 was still intact without detectable degradation.

The invention claimed is:

1. A method of conferring resistance to an infection through passive immunization, the method comprising administering to a host a pharmaceutical composition comprising a compound of the formula

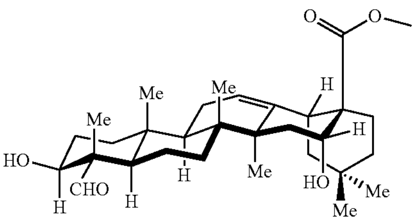

-continued

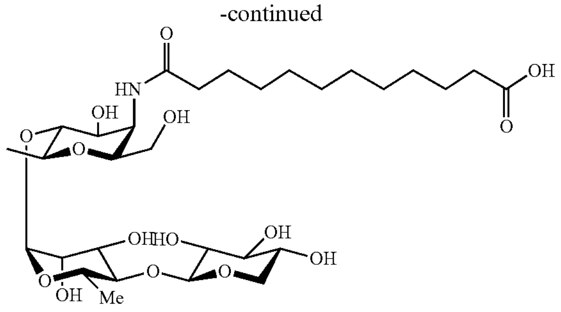

or a pharmaceutically acceptable salt thereof, recovering antisera from the host, and providing the antisera to a recipient.

2. The method according to claim 1, wherein the pharmaceutical composition comprises an antigen.

3. The method according to claim 2, wherein the antigen is an antigen associated with a bacteria or a virus.

4. The method according to claim 3, wherein the antigen is an antigen associated with a bacteria or a virus causing a disease selected from the group consisting of Hepatitis B, pneumococcus, diphtheria, tetanus, pertussis, or Lyme disease including the closely related spirochetes of the genus *Borrelia* such as, *B. burgdorferi, B. garinii, B. afzelli*, and *B. japonica.*

5. The method according to claim 4, wherein the antigen is associated with Hepatitis B virus.

6. The method according to claim 4, wherein the antigen is associated with pneumococcus bacterium.

7. The method according to claim 4, wherein the antigen is associated with *Corynebacterium diphtheria* bacterium.

8. The method according to claim 4, wherein the antigen is associated with *Clostridium* bacterium.

9. The method according to claim 4, wherein the antigen is associated with *Bordetella pertussis* bacterium.

10. The method according to claim 4, wherein the antigen is associated with a bacterium causing Lyme disease or a spirochete of the genus *Borrelia* selected from the group consisting of *B. burgdorferi, B. garinii, B. afzelli*, and *B. japonica.*

11. The method according to claim 1, wherein the antisera contains antibodies.

12. The method according to claim 11, wherein the antisera provided to the recipient includes said antibodies.

13. The method according to claim 2, wherein the antisera contains antibodies against the antigen.

14. The method according to claim 13, wherein the antisera provided to the recipient includes said antibodies against the antigen.

15. The method according to claim 1, wherein the recipient is suspected of having an infection.

16. The method according to claim 1, wherein the recipient is suspected of exposure to an organism that causes or carries an infection.

17. The method according to claim 1, wherein the antisera provided to the recipient results in total or partial attenuation of a symptom or condition of an infection.

* * * * *